US012729391B2

(12) United States Patent
Jenewein et al.

(10) Patent No.: US 12,729,391 B2
(45) Date of Patent: Sep. 8, 2026

(54) BACILLUS CELL WITH REDUCED LIPASE AND/OR ESTERASE SIDE ACTIVITIES

(71) Applicant: BASF SE, Ludwigshafen (DE)

(72) Inventors: Stefan Jenewein, Ludwigshafen (DE); Max Fabian Felle, Ludwigshafen (DE); Christopher Sauer, Ludwigshafen (DE); Paul Igor Costea, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 642 days.

(21) Appl. No.: 18/030,700

(22) PCT Filed: Oct. 6, 2021

(86) PCT No.: PCT/EP2021/077561
§ 371 (c)(1),
(2) Date: Apr. 6, 2023

(87) PCT Pub. No.: WO2022/074056
PCT Pub. Date: Apr. 14, 2022

(65) Prior Publication Data

US 2024/0060110 A1 Feb. 22, 2024

(30) Foreign Application Priority Data

Oct. 7, 2020 (EP) .................................... 20200558
Jul. 7, 2021 (EP) .................................... 21184275

(51) Int. Cl.
*C12P 21/02* (2006.01)
*C12N 9/16* (2006.01)
*C12N 9/20* (2006.01)

(52) U.S. Cl.
CPC ................ *C12P 21/02* (2013.01); *C12N 9/16* (2013.01); *C12N 9/20* (2013.01); *C12Y 301/01001* (2013.01); *C12Y 301/02002* (2013.01)

(58) Field of Classification Search
CPC .. C12P 21/02; C12N 9/16; C12N 9/20; C12N 9/18; C12Y 301/01001; C12Y 301/02002; C12Y 301/01003; C12R 2001/07; C12R 2001/10
See application file for complete search history.

(56) References Cited

U.S. PATENT DOCUMENTS

| | | | |
|---|---|---|---|
| 4,595,594 | A | 6/1986 | Lee et al. |
| 5,352,604 | A | 10/1994 | Wilson et al. |
| 2003/0158070 | A1 | 8/2003 | Estell |

FOREIGN PATENT DOCUMENTS

| | | | | |
|---|---|---|---|---|
| EP | 2287178 | A2 | 2/2011 | |
| WO | WO-98/07817 | A1 | 2/1998 | |
| WO | WO-99/03984 | A2 | 1/1999 | |
| WO | WO-2005/069762 | A2 | 8/2005 | |
| WO | WO-2006/000343 | A2 | 1/2006 | |
| WO | WO-2016184944 | A1 * | 11/2016 | ......... C11D 3/38627 |
| WO | WO-2019/016051 | A1 | 1/2019 | |
| WO | WO-2021/001397 | A1 | 1/2021 | |

OTHER PUBLICATIONS

European Search Report for EP Patent Application No. 20200558.3, Issued on Jul. 1, 2021, 4 pages.
Kuhn, "Gram-Positive Host Cells and Method of Producing Polypeptide", IPCOM000257933D, IP.Com Prior Art Database Technical Disclosure, IP.Com, XP013182688, Mar. 25, 2019, 79 pages.
International Application No. PCT/EP2021/077561, International Search Report and Written Opinion, mailed Apr. 4, 2022.

* cited by examiner

*Primary Examiner* — Paul J Holland
(74) *Attorney, Agent, or Firm* — ArentFox Schiff LLP

(57) ABSTRACT

The present invention provides a modified *Bacillus* cell for the production of a compound of interest, wherein the *Bacillus* cell comprises a genetic modification that leads to decreased production of enzymes with lipase and/or esterase activity. The use of compounds of interest produced with said improved *Bacillus* host cells reduces the formation of malodour and/or off-flavour when used for applications such as washing or cleaning or as feed or food additives.

13 Claims, No Drawings

Specification includes a Sequence Listing.

SEQUENCE LISTING

```
<160> NUMBER OF SEQ ID NOS: 84

<210> SEQ ID NO 1
<211> LENGTH: 190
<212> TYPE: PRT
<213> ORGANISM: Bacillus licheniformis
<220> FEATURE:
<223> OTHER INFORMATION: putative phosphatase (yhfR)

<400> SEQUENCE: 1

Met Thr Ala Ile Cys Leu Ile Arg His Gly Glu Thr Asp Trp Asn Ala
1               5                   10                  15

Leu Gly Lys Leu Gln Gly Arg Thr Asp Ile Pro Leu Asn Glu Thr Gly
            20                  25                  30
```

-continued

```
Lys Lys Gln Ala Lys Glu Thr Gly Ala Phe Leu Lys Gly Ser Asp Trp
        35                  40                  45

Asp Val Ile Ile Thr Ser Pro Leu Arg Arg Ala Lys Glu Thr Ala Glu
    50                  55                  60

Ile Ile Asn Gln Tyr Leu Gly Leu Glu Ile Ile Glu Met Glu Asp Phe
65                  70                  75                  80

Ile Glu Arg Asn Tyr Gly Asp Ala Glu Gly Met Pro Phe Glu Glu Arg
                85                  90                  95

Met Arg Leu Tyr Pro Asp Lys Glu Tyr Pro Asn Gln Glu Ser Lys Glu
            100                 105                 110

Ala Leu Ala Glu Arg Leu Met Ala Gly Val Gln Lys Val Ser Glu Arg
        115                 120                 125

Tyr Pro Asp Lys Lys Val Leu Ile Val Ala His Gly Ala Ala Ile His
    130                 135                 140

Ala Leu Leu Ser Lys Ile Ser Asn Gly Asp Ile Asn Leu Glu Asn Thr
145                 150                 155                 160

Lys Leu Val Asn Ala Cys Leu Ser Asn Ile Lys Phe His Glu Asn Lys
                165                 170                 175

Trp His Val Lys Asp Tyr Asn Leu Ser His His Leu Ser Asp
            180                 185                 190


<210> SEQ ID NO 2
<211> LENGTH: 255
<212> TYPE: PRT
<213> ORGANISM: Bacillus licheniformis
<220> FEATURE:
<223> OTHER INFORMATION: putative peptidase (yitV)

<400> SEQUENCE: 2

Met Ile Ile Ile Glu Lys Gln His Ile Ser Asn Ile Pro Leu Leu His
1               5                   10                  15

Ile Val Lys Glu Glu Lys Lys Glu Lys Ala Leu Pro Leu Val Phe Phe
            20                  25                  30

Ile His Gly Phe Thr Ser Ala Lys Glu His Asn Leu His Phe Ala Tyr
        35                  40                  45

Leu Leu Ala Glu Lys Gly Met Arg Val Ile Leu Pro Glu Ala Leu Tyr
    50                  55                  60

His Gly Glu Arg Asn Glu Gln Leu Thr Gln Glu Glu Leu Ala Pro Arg
65                  70                  75                  80

Phe Trp Glu Ile Val Thr Asn Glu Ile Lys Glu Leu Glu Val Leu Lys
                85                  90                  95

Asn His Phe Glu Arg Glu Asn Met Ile Glu Lys Gly Arg Ile Gly Ala
            100                 105                 110

Ala Gly Thr Ser Met Gly Gly Ile Val Thr Leu Gly Ala Leu Thr Gln
        115                 120                 125

Tyr Glu Trp Ile Thr Thr Ala Val Ser Leu Met Gly Ser Pro Ala Tyr
    130                 135                 140

Val Glu Phe Phe Asp Gln Gln Leu Ala Phe Met Arg Glu Lys Lys Ile
145                 150                 155                 160

Glu Leu Pro Ile Thr Glu Glu Gln Ile Asp Gln Gln Arg Glu Glu Leu
                165                 170                 175

Lys Arg Phe Asp Leu Ser Leu Gln Pro Asp Lys Leu Asn Met Arg Pro
            180                 185                 190

Leu Leu Phe Trp His Gly Lys Gln Asp Gly Thr Val Pro Phe Ala Leu
        195                 200                 205
```

```
Thr Arg Arg Phe Tyr Glu Ser Ile Ile Pro Leu Tyr Glu Ala Arg Pro
    210                 215                 220

Asp Leu Leu His Phe Ile Glu Asp Glu Arg Ala Gly His Lys Val Ser
225                 230                 235                 240

Arg Glu Gly Leu Leu Lys Thr Val Glu Trp Phe Asp Ala His Leu
                245                 250                 255


<210> SEQ ID NO 3
<211> LENGTH: 238
<212> TYPE: PRT
<213> ORGANISM: Bacillus licheniformis
<220> FEATURE:
<223> OTHER INFORMATION: rhamnogalacturonan acetylesterase (yesT)

<400> SEQUENCE: 3

Met Lys Arg Thr Asp Lys Lys Pro Lys Val Thr Val Tyr Leu Ala Gly
1               5                   10                  15

Asp Ser Thr Val Ala Asp Cys Pro Pro His Glu Ala Pro Met Ala Gly
            20                  25                  30

Trp Gly Gln Met Leu Pro Leu Phe Phe Ser Asp Glu Ala Ala Val Val
        35                  40                  45

Asn Met Ala Lys Gly Gly Ala Ser Ser Asn Ser Phe Ile Asp Glu Gly
    50                  55                  60

Arg Leu Asp Asp Ile Thr Glu Arg Leu Ala Pro Gly Asp Tyr Val Leu
65                  70                  75                  80

Ile Gln Phe Gly His Asn Asp Gln Lys Pro Tyr Gly Thr Asp Pro Tyr
                85                  90                  95

Thr Thr Tyr Gln Glu His Leu Val Arg Tyr Val Glu Ala Val Arg Glu
            100                 105                 110

Lys Gln Ala Thr Pro Val Leu Ile Thr Ser Ala Glu Arg Arg Arg Phe
        115                 120                 125

Asp Gln Asn Gly Lys Pro Ala Asp Thr Leu Gly Asp Phe Pro Lys Ala
    130                 135                 140

Met Lys Ala Leu Ala Asp Ser Phe Asp Val Pro Leu Ile Asp Leu Trp
145                 150                 155                 160

Ser Lys Thr Lys Ala Leu Tyr Glu Ser Leu Gly Ile Glu Gly Ser Lys
                165                 170                 175

Arg Leu Phe Val His Phe Gln Pro His Glu His Pro His Tyr Pro Asn
            180                 185                 190

Gly Ile Glu Asp Asn Thr His Phe Ser Glu Ala Gly Ala Arg Gln Val
        195                 200                 205

Ala Arg Leu Val Thr Glu Gly Ile Arg Glu Leu Gly Leu Pro Leu Ser
    210                 215                 220

Ala Tyr Leu Leu Cys Glu Arg Ser Asp Phe Arg Ala Gly Val
225                 230                 235


<210> SEQ ID NO 4
<211> LENGTH: 421
<212> TYPE: PRT
<213> ORGANISM: Bacillus licheniformis
<220> FEATURE:
<223> OTHER INFORMATION: putative carbohydrate esterase (unknown)

<400> SEQUENCE: 4

Met Pro Lys Glu Lys Lys Trp Gly Arg Ser Arg Pro Glu Gln Arg Glu
1               5                   10                  15

Ala Gln Pro Lys Lys Arg Ser Pro Phe Arg Trp Lys Thr Gly Ala Ser
```

-continued

```
            20                  25                  30

Ile Trp Ser Glu Gly Ala Ser Ala Lys Gly Val Cys His Arg Asn Phe
        35                  40                  45

Glu Val Tyr Gln Phe Asp Phe Gly Asp Gly Pro Leu Ala Ser Gly Phe
    50                  55                  60

Ile Pro Val Gly Ala Ala Ser Ala Tyr Thr Pro Leu Lys Gly Tyr Gly
65                  70                  75                  80

Phe Asp Asp Ala Ala Lys Val Ser Cys Thr Asp Arg Gly Thr Ala Asp
                85                  90                  95

Pro Leu Arg Ser Asp Phe Cys Ile Pro Asp Gly Thr Ala Phe Thr Val
            100                 105                 110

Asp Leu Pro Asp Gly Gln Tyr Gln Val Gln Ile Ile Thr Gly Asp Ala
        115                 120                 125

Arg Ala Lys Thr Asn Met Asp Val Arg Ala Asn Gly Met Leu Gln Leu
    130                 135                 140

Tyr Ser Phe Gly Ala Glu Ala Gly Gly Tyr Asn Glu Lys Thr Phe Pro
145                 150                 155                 160

Ile His Ile Ser Gly Gly Arg Leu Ser Ile Gln Ala Leu Thr Ala Arg
                165                 170                 175

Thr Met Pro Arg Leu Asn Ala Leu Val Ile Thr Lys Thr Ala Tyr His
            180                 185                 190

Val Thr Asp Asp Asn Thr Thr Val Phe Leu Ala Gly Asp Ser Thr Val
        195                 200                 205

Ser Asp Tyr Glu Pro Gly Tyr Ala Pro Met Ala Gly Trp Gly Gln Phe
    210                 215                 220

Leu Gly Gly Tyr Phe Ser Asp Glu Ile Val Ile Asp Asn Gln Ala Lys
225                 230                 235                 240

Arg Ala Arg Ser Ala Lys Ser Phe Val Asp Glu Arg Ser Leu Ala Thr
                245                 250                 255

Ile Leu Asn Arg Met Lys Arg Gly Asp Tyr Leu Leu Ile Gln Phe Gly
            260                 265                 270

Ile Asn Asp Ala Gly Gln Asp Pro Ala Arg His Thr Asp Pro Tyr Thr
        275                 280                 285

Thr Phe Gln Glu Tyr Leu Arg Thr Tyr Ile Asn Lys Ala Arg Glu Lys
    290                 295                 300

Gly Gly Arg His Val Leu Val Thr Ser Gln Ser Lys Arg Thr Tyr Asp
305                 310                 315                 320

Glu Lys Gly Val Phe Tyr Asn Ser Ile Gly Glu Tyr Pro Asn Ala Met
                325                 330                 335

Arg Gln Leu Gly Arg Glu Met Asn Val Pro Val Ile Asp Leu Asn Lys
            340                 345                 350

Lys Ser Ile Glu Tyr Tyr Asn Glu Ile Gly Val Glu Ala Thr Lys Asn
        355                 360                 365

Val Phe Met Phe Leu Glu Pro Gly Glu Ser Pro Asn Tyr Pro Glu Gly
    370                 375                 380

Ile Gln Asp Arg Val His Phe His Glu Phe Gly Ala Asn Gln Leu Ala
385                 390                 395                 400

Arg Leu Val Thr Gly Glu Ile Ser Asp Leu Asn Ile Tyr Pro Leu Lys
                405                 410                 415

His Ser Leu Lys Lys
            420
```

<210> SEQ ID NO 5

<211> LENGTH: 214
<212> TYPE: PRT
<213> ORGANISM: Bacillus licheniformis
<220> FEATURE:
<223> OTHER INFORMATION: putative rhamnogalacturonan acetylesterase
(yesY)

<400> SEQUENCE: 5

```
Met Thr Ile Ser Ile Tyr Leu Ala Gly Asp Ser Thr Val Gln His Tyr
1               5                   10                  15

Lys Ala Asp Ser Pro Gln Gly Gly Trp Gly Glu Phe Leu Gln Ser Tyr
            20                  25                  30

Leu Ser Gly Asn Val Gln Val Ile Asn Arg Ala Ile Gly Gly Arg Ser
        35                  40                  45

Ser Lys Thr Phe Val Glu Glu Gly Arg Leu Ala Ser Ile Leu Asp Val
    50                  55                  60

Ile Lys Gln Asp Asp Trp Leu Phe Val Gln Met Gly His Asn Asp Ala
65                  70                  75                  80

Ser Lys Asp Lys Pro Glu Arg Tyr Thr Glu Pro Tyr Thr Thr Tyr Lys
                85                  90                  95

Gln Tyr Leu Lys Met Tyr Val Asp Gly Ala Arg Gln Lys Gly Ala Ser
            100                 105                 110

Pro Leu Leu Ile Thr Pro Val Ala Arg Leu His Tyr Lys Asp Gly Val
        115                 120                 125

Phe Leu Asn Asp Phe Pro Asp Tyr Cys Ile Ala Met Lys Gln Val Ala
    130                 135                 140

Ser Glu Glu Asn Val Arg Leu Ile Asp Leu Met Asp Lys Ser Leu Gln
145                 150                 155                 160

His Phe Ala Glu Lys Gly Tyr Ser Glu Val Phe Lys Tyr Phe Met Ile
                165                 170                 175

Ser Glu Asn Val Asn Asp Tyr Thr His Phe Thr Lys Lys Gly Ala Arg
            180                 185                 190

Glu Met Ala Lys Leu Val Ser Glu Gly Ile Arg Glu Leu Gly Leu Pro
        195                 200                 205

Phe Val Lys Glu Thr Val
    210
```

<210> SEQ ID NO 6
<211> LENGTH: 371
<212> TYPE: PRT
<213> ORGANISM: Bacillus licheniformis
<220> FEATURE:
<223> OTHER INFORMATION: hypothetical protein (unknown)

<400> SEQUENCE: 6

```
Met Tyr Leu Asn Lys Lys Ser Asp Ile Pro Lys Leu Thr Asp Lys Glu
1               5                   10                  15

Tyr Tyr Phe Leu Ser Gln Asn Thr Tyr Ser Thr Asp Lys Met Lys Glu
            20                  25                  30

Ala Phe Lys Glu Arg Thr Pro Ile Glu Ser Lys Ser Asn Lys Ala Phe
        35                  40                  45

Phe Val Asp Lys Ile Lys Arg Asp Ser Asp Thr Gly Leu Asp Ala Tyr
    50                  55                  60

Val Phe Val Gln Ala Lys Lys Lys Asp Gly Lys Trp Val Lys Pro Asn
65                  70                  75                  80

Ala Pro Glu Asn Val Val Val Ala Phe Ala Gly Thr Asn Pro Lys Glu
                85                  90                  95
```

-continued

```
Gln Phe Phe Gln Asp Val Ile Asp Ala Asp Gly Gly Asn Val Val Met
            100                 105                 110

Gly Leu Asp Pro Lys Lys Lys Ser Gln Tyr Ile Ile Glu Lys Asp Ala
        115                 120                 125

Lys Asp Thr Ser Lys Thr Ile Gly Lys Tyr Asn Ala Thr Pro Ser Gln
    130                 135                 140

Asp Ala Met Leu Ser Thr Gly Lys Tyr Lys Leu Ile Thr Lys Thr Ser
145                 150                 155                 160

Gln Ile Gly Gln Ala Asp Asp Leu Val Arg Glu Val Lys Gln Lys Tyr
                165                 170                 175

Lys Gly Thr Ser Thr Val Ile Ser Thr Thr Gly His Ser Leu Gly Gly
            180                 185                 190

Ala Glu Ala Glu Tyr Ser Ala Val Asn Asn Asp Ile Tyr Ala Val Ala
        195                 200                 205

Phe Asn Asn Pro Ser Val Val Lys Leu His Ser Glu Glu Lys Gln Lys
    210                 215                 220

Glu Ile Arg Ser Gly Lys Tyr Asp Ser Ser Val Lys Ala Ile Val Asn
225                 230                 235                 240

Pro Asp Asp Met Thr Gly Ser Gly Trp Trp Asn Glu Tyr Glu Arg His
                245                 250                 255

Ala Gly Arg Thr Ile Tyr Thr Lys Asp Pro Ser Thr Ser Arg Val Glu
            260                 265                 270

Arg Gln Ile Arg Leu Asp Pro Lys Tyr Ser Gly Gly Ile Phe Gly Thr
        275                 280                 285

Val Phe Asn Val Ala Val Asp Tyr Ile Ala Thr Thr Ala Met Gly Met
    290                 295                 300

Pro Asp Thr His Gly Leu Asn Lys Gly Asn Phe Thr Phe Asp Glu Asn
305                 310                 315                 320

Gly Asn Val Gln Asn Ile Glu Gly Asp Glu Leu Val Tyr Asp Lys Asn
                325                 330                 335

Leu Lys Ala Met Leu Pro Pro Glu Val Ala Ser Gly Ser Gly Ala Ile
            340                 345                 350

Lys Val Thr Pro Glu Val Ala Lys Gln Leu Ala Gln Lys Val Asn Ala
        355                 360                 365

Cys Gly Arg
    370
```

<210> SEQ ID NO 7
<211> LENGTH: 338
<212> TYPE: PRT
<213> ORGANISM: Bacillus licheniformis
<220> FEATURE:
<223> OTHER INFORMATION: flagellar motor switch protein (fliG)

<400> SEQUENCE: 7

```
Met Ala Lys Met Lys Gln Asp Arg Leu Thr Gly Lys Gln Lys Ala Ala
1               5                   10                  15

Ile Leu Met Ile Ser Leu Gly Leu Asp Val Ser Ala Ser Val Tyr Lys
            20                  25                  30

His Leu Thr Asp Glu Glu Ile Glu Arg Leu Thr Leu Glu Ile Ser Asn
        35                  40                  45

Val Arg Ala Val Ser Pro Glu Lys Lys Asp Glu Ile Ile Gln Glu Phe
    50                  55                  60

His Glu Thr Ala Ile Ala Gln Glu Tyr Ile Ser Gln Gly Gly Ile His
65                  70                  75                  80
```

-continued

Tyr Ala Lys Gln Val Leu Asp Lys Ala Leu Gly Glu Asp Lys Ala Ala
85 90 95

Ser Ile Ile Asn Arg Leu Thr Ser Ser Leu Gln Val Arg Pro Phe Asp
100 105 110

Phe Ala Arg Lys Ala Asp Pro Glu Gln Ile Leu Asn Phe Ile Gln His
115 120 125

Glu His Pro Gln Thr Ile Ala Leu Ile Leu Ser Tyr Leu Asp Pro Val
130 135 140

Gln Ser Gly Gln Ile Leu Ser Glu Leu Asn Gln Asp Val Gln Ala Glu
145 150 155 160

Val Ala Arg Arg Ile Ala Val Met Asp Arg Thr Ser Pro Glu Ile Ile
165 170 175

Asn Glu Val Glu Gln Ile Leu Glu Gln Lys Leu Ser Ser Thr Phe Thr
180 185 190

Gln Asp Tyr Thr Gln Thr Gly Gly Ile Glu Ala Val Val Glu Val Leu
195 200 205

Asn Gly Val Asp Arg Gly Thr Glu Lys Thr Ile Leu Asp Ala Leu Glu
210 215 220

Ile Gln Asp Pro Glu Leu Ala Asp Glu Ile Lys Lys Arg Met Phe Val
225 230 235 240

Phe Glu Asp Ile Val Thr Leu Asp Asn Arg Ala Ile Gln Arg Val Ile
245 250 255

Arg Asp Val Glu Asn Asp Asp Leu Leu Leu Ser Leu Lys Val Ala Ser
260 265 270

Glu Glu Val Lys Asp Ile Val Phe Ser Asn Met Ser Gln Arg Met Ala
275 280 285

Glu Thr Phe Lys Glu Glu Met Glu Phe Met Gly Pro Val Arg Leu Arg
290 295 300

Asp Val Glu Glu Ala Gln Ser Arg Ile Val Ser Val Ile Arg Arg Leu
305 310 315 320

Glu Glu Ala Gly Glu Ile Val Ile Ala Arg Gly Gly Gly Asp Asp Ile
325 330 335

Ile Val

<210> SEQ ID NO 8
<211> LENGTH: 286
<212> TYPE: PRT
<213> ORGANISM: Bacillus licheniformis
<220> FEATURE:
<223> OTHER INFORMATION: AB hydrolase superfamily protein (yisY)

<400> SEQUENCE: 8

Met Phe Ser Pro Arg Arg His Ser Pro Ile Tyr Ile Leu Gly Val Ser
1 5 10 15

Tyr Gly Lys Asp Met Ile Gly Gly Asp Gly Met Gly Tyr Phe Ile Glu
20 25 30

Ala Glu Pro Ser Val Asn Leu Tyr Val Glu Asp Ile Asn Pro Gln Ser
35 40 45

Gly Lys Ala Ile Val Phe Leu His Gly Trp Pro Leu Ser His Leu Gln
50 55 60

Phe Glu Tyr Gln Phe Asp Asp Leu Ser Arg Lys Gly Tyr Arg Cys Ile
65 70 75 80

Gly Ile Asp Trp Arg Gly Phe Gly Arg Ser Asp Lys Pro Ala Thr Gly
85 90 95

Tyr Asn Tyr Asn Arg Leu Ala Asp Asp Ile Arg Ala Val Val Glu Ala

```
            100                 105                 110

Leu Gln Leu Asn Asn Phe Thr Leu Ala Gly His Ser Thr Gly Gly Ala
        115                 120                 125

Ile Ala Leu Arg Tyr Met Ser Arg Tyr Arg Gly Ala Gly Val Ser Lys
    130                 135                 140

Leu Val Leu Ile Asp Ala Ala Ala Pro Val Gly Phe Thr Glu Glu Thr
145                 150                 155                 160

Ala Ala Lys Leu Leu Gln Gln Ala Ser Asn Asp Arg Pro Lys Met Met
                165                 170                 175

Arg Glu Val Thr Asp Thr Phe Phe Phe Gln Tyr Ile Thr Gln Pro Phe
            180                 185                 190

Ser Asp Cys Phe Phe Gln Leu Gly Leu Gln Ala Ala Gly Trp Ser Thr
        195                 200                 205

Lys Ala Val Ile Glu Met Leu Arg Asp Glu Lys Leu Tyr Asp Asp Pro
    210                 215                 220

Glu Lys Val Ala Ala Pro Ala Leu Ile Ile His Gly Ile Gln Asp Lys
225                 230                 235                 240

Val Ile Pro Phe Ala Gln Ala Lys Glu Leu Ser Arg Lys Ile Arg Asn
                245                 250                 255

Ser Tyr Leu Val Pro Phe Gln Tyr Ser Gly His Gly Pro Phe Trp Glu
            260                 265                 270

Glu Arg Lys Met Phe Asn Arg Ile Leu Thr Gln Phe Ile Gly
        275                 280                 285


<210> SEQ ID NO 9
<211> LENGTH: 201
<212> TYPE: PRT
<213> ORGANISM: Bacillus licheniformis
<220> FEATURE:
<223> OTHER INFORMATION: putative hydrolase (mhqD)

<400> SEQUENCE: 9

Met Asn Tyr Ile Tyr Glu Lys Gly Asp Ser Asp Leu Thr Leu Leu Leu
1               5                   10                  15

Leu His Gly Thr Gly Gly Asn Glu His Asp Leu Leu Pro Ile Gly Lys
            20                  25                  30

Met Ile Asp Pro Asp Ala Asn Leu Leu Gly Val Arg Gly Asn Val Leu
        35                  40                  45

Glu Asn Gly Met Pro Arg Phe Phe Arg Arg Leu Arg Glu Gly Val Phe
    50                  55                  60

Asp Glu Lys Asp Leu Ile Glu Arg Thr Asp Glu Leu Lys Thr Phe Leu
65                  70                  75                  80

Asp Glu Ala Ala Lys Glu Leu His Phe Asp Arg Ser Arg Val Val Ala
                85                  90                  95

Ile Gly Tyr Ser Asn Gly Ala Asn Ile Ala Gly Ser Leu Leu Phe Arg
            100                 105                 110

His Glu His Val Leu Lys Gly Ala Ile Leu His His Pro Met Val Pro
        115                 120                 125

Phe Arg Asn Arg Lys Leu Pro Asp Met Thr Gly Leu Pro Val Phe Ile
    130                 135                 140

Gly Ala Gly Lys Thr Asp Pro Leu Cys Pro Pro Gln Glu Ser Ser Glu
145                 150                 155                 160

Leu Ala Gly Tyr Phe Thr Asn Ala Gly Ala Lys Val Leu Leu His Trp
                165                 170                 175

Glu Gly Gly Gly His Gln Leu Thr His Gly Glu Ile Glu Lys Ala Lys
```

```
            180                 185                 190

Ile Trp Tyr Glu Lys His Ile Lys Ala
        195                 200


<210> SEQ ID NO 10
<211> LENGTH: 250
<212> TYPE: PRT
<213> ORGANISM: Bacillus licheniformis
<220> FEATURE:
<223> OTHER INFORMATION: putative esterase (ypmR)

<400> SEQUENCE: 10

Met Asn Ile Arg Phe Ile Thr Val Met Met Ala Leu Val Cys Leu Leu
1               5                   10                  15

Ser Ala Cys Thr Glu Trp Asn Ala Gly Val Glu Lys Thr Ser Val Ser
            20                  25                  30

Pro Lys Arg Asp Ile Val Ile Ala Ala Val Gly Asp Ser Leu Thr Glu
        35                  40                  45

Gly Val Gly Asp Gln Glu Lys Lys Gly Tyr Val Gly Met Val Ala Asp
    50                  55                  60

Glu Leu Glu Ser Arg Ser Asp Val Lys Ser Val Thr Val Lys Asn Tyr
65                  70                  75                  80

Ala Val Lys Gly Ser Arg Thr Asp Gln Leu Leu Glu Arg Leu Lys Asp
                85                  90                  95

Lys Glu Val Gln Glu Gly Leu Lys Asp Ala Asp Tyr Ile Leu Phe Thr
            100                 105                 110

Ile Gly Gly Asn Asp Leu Met Lys Val Val Arg Gln Asn Phe Ala His
        115                 120                 125

Leu Thr Leu Thr Pro Phe Arg Ala Glu Gln Lys Leu Phe Glu Lys Arg
    130                 135                 140

Phe Ser Asn Ile Leu Ala Glu Ile Arg Glu Gln Asn Ala Ser Ala Glu
145                 150                 155                 160

Leu Ile Tyr Val Ser Met Tyr Asn Pro Phe Lys Phe Thr Leu Ser Glu
                165                 170                 175

Leu Arg Glu Val Asp Gln Val Val Asp Glu Trp Asn Glu Gly Ala Glu
            180                 185                 190

Lys Arg Leu Lys Lys Val Ser Asn Thr Lys Met Ala Asp Ile Ala Asp
        195                 200                 205

Ile Phe Glu Glu Tyr Ser Asp Glu Lys Lys Ile Ala Glu Asp Glu Phe
    210                 215                 220

His Pro Asn Gln Tyr Gly Tyr Ser Leu Ile Ala Lys Arg Val Tyr Glu
225                 230                 235                 240

Gln Ile Lys Asn Glu Asp Leu Pro Ala Glu
                245                 250


<210> SEQ ID NO 11
<211> LENGTH: 204
<212> TYPE: PRT
<213> ORGANISM: Bacillus licheniformis
<220> FEATURE:
<223> OTHER INFORMATION: putative lipase (lip)

<400> SEQUENCE: 11

Met Arg Arg His Ser Phe Leu Ser Ile Leu Leu Ile Cys Met Leu Ser
1               5                   10                  15

Val Val Ser Val Phe Ser Phe Arg Pro Ser Ala Ala Ser Ala Ala Ser
            20                  25                  30
```

-continued

```
His Asn Pro Val Val Met Val His Gly Ile Gly Gly Ala Asp Tyr Asn
        35                  40                  45

Phe Ile Gly Ile Lys Ser Tyr Leu Gln Ser Gln Gly Trp Thr Ser Ser
    50                  55                  60

Glu Leu Tyr Ala Ile Asn Phe Ile Asp Lys Thr Gly Asn Asn Ile Asn
65                  70                  75                  80

Asn Ala Pro Arg Leu Ser Glu Tyr Ile Lys Arg Val Leu Asn Gln Thr
                85                  90                  95

Gly Ala Ser Lys Val Asp Ile Val Ala His Ser Met Gly Gly Ala Asn
            100                 105                 110

Thr Leu Tyr Tyr Ile Lys Asn Leu Asp Gly Ala Asp Lys Val Gly His
        115                 120                 125

Val Val Thr Leu Gly Gly Ala Asn Arg Leu Val Thr Asn Thr Ala Pro
    130                 135                 140

Gln Asn Asp Lys Ile Ser Tyr Thr Ser Ile Tyr Ser Thr Ser Asp Tyr
145                 150                 155                 160

Ile Val Leu Asn Ser Leu Ser Lys Leu Asp Gly Ala Asn Asn Val Gln
                165                 170                 175

Ile Ser Gly Val Ser His Val Gly Leu Leu Phe Ser Ser Lys Val Asn
            180                 185                 190

Ala Leu Ile Lys Asp Gly Leu Thr Ala Ser Gly Lys
        195                 200


<210> SEQ ID NO 12
<211> LENGTH: 253
<212> TYPE: PRT
<213> ORGANISM: Bacillus licheniformis
<220> FEATURE:
<223> OTHER INFORMATION: hypothetical protein (yqiL)

<400> SEQUENCE: 12

Met Thr Ile Thr Glu Arg Ile Tyr Thr Val Glu Gly Cys Met Phe Tyr
1               5                   10                  15

Thr Lys Gln Arg Lys Gly Lys Lys Asn Ala Thr Ile Ile Phe Glu Ala
            20                  25                  30

Gly Tyr Gly Phe Ser Ser Thr Thr Trp Gln Pro Ile Leu Ser Asp Ile
        35                  40                  45

Asp Glu Asp Leu Gly Leu Phe Ala Tyr Asp Arg Ala Gly Leu Gly Lys
    50                  55                  60

Ser Gly Pro Ser Thr Ser Lys Arg Thr Ala Asp Gln Met Val Lys Glu
65                  70                  75                  80

Leu Lys Ala Leu Leu Ala Ala Ala Asp Val Lys Pro Pro Tyr Leu Phe
                85                  90                  95

Val Ala His Ser Phe Gly Ala Val Ile Ala Arg Leu Phe Ala Ser Arg
            100                 105                 110

Tyr Ser Asp Glu Val Ile Gly Met Val Leu Leu Asp Pro Ala Cys Glu
        115                 120                 125

Asp Gln Glu Glu Lys Val Leu Pro Leu Leu Pro Asp Thr Leu Lys Glu
    130                 135                 140

Asp Tyr Val Lys Gln Phe Ser Ile Glu Gly Ser His Glu Asp Phe Lys
145                 150                 155                 160

Gln Ser Leu Asp Met Leu Lys Gln Glu Lys Lys His Leu Gly Ser Val
                165                 170                 175

Pro Leu Leu Val Leu Ser Ala Gly Lys Arg Thr Glu Ala Ala Lys Gln
            180                 185                 190
```

-continued

```
Ala His Gln Glu Trp Leu Lys Leu His Ser Arg Leu Leu Ser Leu Ser
        195                 200                 205

His Gln Ser Gly Trp Ile Gln Ala Lys Asn Ser Ser His Leu Ile His
    210                 215                 220

His Asp Glu Pro His Ile Val Gln Leu Ala Ile Tyr Asp Val Trp Tyr
225                 230                 235                 240

Ala Ala Gln Gln Gln Thr Tyr Ala Tyr Gln Ala Ala Asn
                245                 250


<210> SEQ ID NO 13
<211> LENGTH: 243
<212> TYPE: PRT
<213> ORGANISM: Bacillus licheniformis
<220> FEATURE:
<223> OTHER INFORMATION: putative lipoprotein (yqeF)

<400> SEQUENCE: 13

Met Lys Lys Ser Leu Val Met Val Leu Val Phe Leu Leu Leu Leu Ser
1               5                   10                  15

Gly Cys Gly Glu Asp Asp Pro Arg Lys Val Val Ala Phe Gly Asp Ser
            20                  25                  30

Asn Thr Arg Gly Ser Asn Trp Gln Phe Arg Asp Tyr Pro Lys Ala Glu
        35                  40                  45

Lys Trp Val Asn Leu Leu Gln Thr Ser Leu Gln Gly Gln Tyr Lys Ile
    50                  55                  60

Asn Asn Ala Gly Ile Gly Gly Glu Thr Thr Glu Asp Ala Arg Phe Arg
65                  70                  75                  80

Phe Arg Lys Asp Val Leu Asp Lys Gln Pro Ala Tyr Leu Phe Ile Met
                85                  90                  95

Phe Gly Thr Asn Asp Ala Ala Ile Leu Thr Lys Gly Leu Pro Arg Val
            100                 105                 110

Ser Lys Lys Arg Phe Lys Glu Asn Leu Tyr Tyr Phe Val Lys Glu Ser
        115                 120                 125

Arg Arg Arg Gly Ile Glu Pro Val Leu Met Thr Cys Leu Pro Ile Val
    130                 135                 140

Glu Gly Ser Gly Asp Asn Ile Phe Tyr Tyr Ala Arg Tyr Arg Ala Ser
145                 150                 155                 160

Ser Phe Glu Lys Tyr Gly Gly Ala Arg Lys Trp His Asp Ser Tyr Asn
                165                 170                 175

Asp Val Thr Arg Glu Thr Ala Arg Glu Leu Asp Val Pro Leu Ile Asp
            180                 185                 190

Asn Trp Lys Asn Ile Val Lys Lys Ala Gly Gly Ala Thr Asp Glu Lys
        195                 200                 205

Leu Ile His Ser Arg Phe Ile Asp Pro Ser Gly Asn His Leu Thr Pro
    210                 215                 220

Lys Gly Ala Arg Ile Ile Phe Glu Gly Ile Asn Lys Ser Lys Ile Ile
225                 230                 235                 240

Lys Thr Ser


<210> SEQ ID NO 14
<211> LENGTH: 275
<212> TYPE: PRT
<213> ORGANISM: Bacillus licheniformis
<220> FEATURE:
<223> OTHER INFORMATION: putative lipolytic enzyme (unknown)

<400> SEQUENCE: 14
```

-continued

Met Arg Gly Phe Ile Lys Trp Ala Gly Leu Ala Ile Leu Cys Ile Gly
1 5 10 15

Leu Phe Ala Cys Thr Ser Asn Arg Asn Ala Glu Asn Val His Tyr Ala
20 25 30

Lys Asp Asp Arg Gln Thr Leu Asp Ile Tyr Thr Pro Gln Ser Asn Glu
35 40 45

Gly Glu Lys His Pro Val Leu Ile Tyr Leu His Gly Gly Gly Trp Thr
50 55 60

Ser Gly Asp Lys Ser Arg Ala Ala Ser Lys Pro Ala Phe Phe Thr Asp
65 70 75 80

Asn Gly Tyr Val Phe Val Ser Val Asn Tyr Arg Leu His Pro Asp Val
85 90 95

Gln Tyr Asp Glu Met Ala Asp Asp Ala Ala Lys Ala Val Lys Trp Val
100 105 110

Met Asp His Ala Asp Glu Tyr Gln Ile Asp Pro Ser Lys Ile Asn Val
115 120 125

Met Gly His Ser Ala Gly Gly His Leu Ala Gly Leu Ile Ala Ala Asp
130 135 140

Ser Thr Tyr Leu Asn Arg Val Gly Leu Thr Pro Ala Ala Leu Asn Ser
145 150 155 160

Ile Val Val Leu Asp Gly Pro Leu Asp Met Lys Arg Phe Ile Glu Ala
165 170 175

Ile Pro Ser Tyr Lys Glu Val Phe Gly Thr Asp Glu Lys Val Trp Thr
180 185 190

Lys Ala Ser Pro Leu Ser Tyr Ile Asn Asn Ser Lys Leu Pro Pro Ala
195 200 205

Tyr Leu Val Thr Arg Trp Glu Asp Pro Ala Val Tyr Lys Phe Ala Glu
210 215 220

Thr Ala Asn Lys Ala Lys Ala Thr Glu Phe Val Tyr Gln Val Asn Ser
225 230 235 240

Leu Ser His Ser Asp Leu Asn Lys Met Phe Gly Ser Pro Asp Ala Pro
245 250 255

Ala Glu Ala Gln Asn Leu Thr Lys Ala Val Met Ala Phe Leu Glu Lys
260 265 270

Glu Asn Lys
275

<210> SEQ ID NO 15
<211> LENGTH: 295
<212> TYPE: PRT
<213> ORGANISM: Bacillus licheniformis
<220> FEATURE:
<223> OTHER INFORMATION: putative hydrolase (ytaP)

<400> SEQUENCE: 15

Met Arg Ser Gln Leu Phe Lys Leu Leu Gly Asp Leu Pro Gly Lys Lys
1 5 10 15

Ser Ile Asp Ala Ser Thr Leu Lys Ile Glu Glu Lys Ser Ser Phe Ile
20 25 30

Leu Glu Thr Leu Leu Leu Asp Leu Asn Gly Ile Glu Ala Val Pro Ala
35 40 45

Tyr Phe Ala Lys Pro Lys Gln Met Asn Gly Lys Arg Pro Ala Val Leu
50 55 60

Tyr Cys His Ser His Gly Gly Arg Tyr Glu Arg Gly Lys Glu Glu Leu
65 70 75 80

-continued

Val Glu Gly Ala Glu Tyr Leu Gln Ala Pro Pro Phe Ala Glu Glu Leu
85 90 95

Thr Ala Leu Gly Phe Ser Val Leu Ala Ile Asp His Trp Ala Phe Gly
100 105 110

Asp Arg Arg Gly Lys Thr Glu Ser Glu Ile Phe Lys Glu Met Leu Trp
115 120 125

Thr Gly Arg Val Met Trp Gly Met Met Val Phe Asp Ser Ile Arg Ala
130 135 140

Ile Asp Tyr Leu Lys Met Arg Glu Asp Ile Asp Glu Ser Arg Ile Ala
145 150 155 160

Ser Leu Gly Met Ser Met Gly Gly Leu Met Ala Trp Trp Thr Ala Ala
165 170 175

Leu Asp Glu Arg Val Ser Val Cys Val Asp Ile Cys Ala Gln Val Asp
180 185 190

Ser Glu Thr Leu Ile Lys Thr Gln Asn Leu Asp Arg His Asn Leu Tyr
195 200 205

Ser Tyr Val Pro Gly Leu Val Lys His Phe Ser Thr Ala Gln Ile Glu
210 215 220

Ser Leu Ile Ala Pro Arg Pro His Leu Ser Leu Val Gly Thr Ala Asp
225 230 235 240

Lys Leu Thr Pro Val Gln Gly Ile Asp Ile Ile Glu Glu Lys Leu Ser
245 250 255

Asp Val Tyr Ile Glu Lys Gly Ala Gly Glu Arg Tyr Glu Val Phe Arg
260 265 270

Ser His Ser Gly His Leu Glu Thr Ala Gly Met Arg His Lys Ala Val
275 280 285

Gly Phe Leu Lys Thr Trp Leu
290 295

<210> SEQ ID NO 16
<211> LENGTH: 259
<212> TYPE: PRT
<213> ORGANISM: Bacillus licheniformis
<220> FEATURE:
<223> OTHER INFORMATION: phospholipase (ytpA)

<400> SEQUENCE: 16

Met Trp Cys Met Glu Ala Glu Arg Pro Val Ala Thr Ile Val Val Ile
1 5 10 15

His Gly Ala Cys Glu His His Gly Arg Tyr Lys Trp Leu Ser Glu Met
20 25 30

Trp Arg Ser Ser Gly Phe Asn Val Val Met Gly Asp Leu Pro Gly Gln
35 40 45

Gly Thr Ser Thr Arg Glu Arg Gly His Ile Arg Ser Phe Gln Glu Tyr
50 55 60

Ile Asp Glu Val Asp Lys Trp Val Ala Arg Ala Lys Ala Phe Glu Leu
65 70 75 80

Pro Val Phe Met Leu Gly His Ser Met Gly Gly Leu Ile Ala Ile Glu
85 90 95

Trp Phe Lys Gln Gln Gln Ser Gly Ile Ala Gly Leu Ile Leu Ser Ser
100 105 110

Pro Cys Leu Gly Leu Gln Leu Lys Pro Asn Lys Phe Leu Asp Leu Ile
115 120 125

Ser Lys Gly Leu Asn Val Leu Ala Pro Ser Met Arg Phe Glu Ser Gly
130 135 140

-continued

```
Ile Thr Pro Asp Lys Ala Thr Arg Asn Lys Glu Val Ile Glu Met Asp
145                 150                 155                 160

Ile Asn Asp Ser Leu Tyr Ile Thr Lys Val Ser Val Arg Trp Tyr Gln
                165                 170                 175

Glu Met Leu Lys Ala Leu Lys Ser Ala Met Glu Pro Thr Asp Ala Phe
            180                 185                 190

Leu Asn Ile Pro Leu Phe Val Met Gln Ala Gly Thr Asp Trp Leu Val
        195                 200                 205

Asp Lys Lys Met Val Val Lys Trp Phe Asn Gln Leu Ala Ser His Asn
    210                 215                 220

Lys Thr Tyr Arg Glu Trp Asp Gly Leu Tyr His Glu Ile Phe Asn Glu
225                 230                 235                 240

Pro Glu Arg Glu Asp Val Phe Lys Ala Ala Arg Ala Phe Ala Glu Gln
                245                 250                 255

Tyr Ile Thr


<210> SEQ ID NO 17
<211> LENGTH: 266
<212> TYPE: PRT
<213> ORGANISM: Bacillus licheniformis
<220> FEATURE:
<223> OTHER INFORMATION: putative dipeptidylpeptidase (ytmA)

<400> SEQUENCE: 17

Met Trp Ile Glu Lys Arg Arg Phe Pro Ser Pro Asn Lys Glu Val Arg
1               5                   10                  15

Leu Phe Ser Val Thr Tyr Leu Ser Gln Gly Leu Lys Val Lys Gly Leu
            20                  25                  30

Leu Ala Glu Pro Ala Ala Pro Gly Asn Tyr Asp Gly Phe Leu Tyr Leu
        35                  40                  45

Arg Gly Gly Ile Lys Asn Val Gly Met Val Arg Pro Gly Arg Ile Val
    50                  55                  60

Gln Phe Ala Ser Gln Gly Phe Val Val Leu Ala Pro Phe Tyr Arg Gly
65                  70                  75                  80

Asn Gln Gly Gly Glu Gly Asp Glu Asp Phe Ala Gly Asn Asp Arg Glu
                85                  90                  95

Asp Ala Phe Ala Ala Phe Arg Leu Leu Gln Lys His Glu Leu Val Lys
            100                 105                 110

Asp Gly Arg Val His Ile Phe Gly Phe Ser Arg Gly Gly Ile Met Gly
        115                 120                 125

Ile Leu Thr Ala Ile Glu Met Lys Ala Ala Ala Ala Ser Phe Val Ser
    130                 135                 140

Trp Gly Gly Val Ser Asp Met Val Met Thr Tyr Arg Glu Arg Lys Asp
145                 150                 155                 160

Leu Arg Arg Met Met Lys Arg Val Ile Gly Gly Thr Pro Glu Lys Val
                165                 170                 175

Pro Glu Ala Tyr Glu Trp Arg Thr Pro Phe Asp Glu Leu Glu Lys Ile
            180                 185                 190

Glu Ala Pro Val Leu Leu Ile His Gly Ala Asn Asp Glu Asn Val Ser
        195                 200                 205

Ile Glu His Ala Arg Arg Leu Glu Arg Glu Leu Leu Arg Arg Asn Lys
    210                 215                 220

Ser Val Asp Thr Trp Tyr Phe Ser Gln Tyr Thr His Tyr Phe Pro Pro
225                 230                 235                 240

Arg Glu Asn Arg Arg Ile Val Arg Glu Leu Ser Gln Trp Met Lys Ser
```

```
                245                 250                 255

Arg Pro Trp Thr Ser Tyr Gly Lys Leu Lys
            260                 265


<210> SEQ ID NO 18
<211> LENGTH: 273
<212> TYPE: PRT
<213> ORGANISM: Bacillus licheniformis
<220> FEATURE:
<223> OTHER INFORMATION: 2-succinyl-6-hydroxy-2, 4-cyclohexadiene-1-
      carboxylate synthase (ytxM)

<400> SEQUENCE: 18

Met Ala Val Leu Lys Leu Thr Leu Lys Asp Gly Val Ser Tyr Lys Ile
1               5                   10                  15

Glu Asp Asn Gly Leu Ser Ala Glu Lys Thr Ala Val Phe Leu His Gly
            20                  25                  30

Phe Thr Gly Ser Ala Ala Thr Trp Asp Gly Ile Asp Gly Tyr Phe Gln
        35                  40                  45

Gly Met Arg Leu Ile Lys Leu Asn Leu Leu Gly His Gly Gly Thr Asp
    50                  55                  60

Ser Pro Ser Asp Ser Arg Arg Tyr Thr Thr Glu Lys Gln Ala Ala Asp
65                  70                  75                  80

Leu Ile Glu Ile Phe Asp Arg Leu Asn Val Lys Gln Ala Tyr Leu Ile
                85                  90                  95

Gly Tyr Ser Met Gly Gly Arg Leu Ala Leu Ser Leu Ala Met Ile His
            100                 105                 110

Pro Glu Arg Val Ser Gly Leu Val Leu Glu Ser Ser Ser Pro Gly Leu
        115                 120                 125

Asp Ser Pro Glu Glu Arg Lys Ala Arg Arg Glu Gln Asp Ser Arg Leu
    130                 135                 140

Ser Arg Arg Ile Leu Glu Glu Gly Ile Lys Ser Phe Val Asp Tyr Trp
145                 150                 155                 160

Glu Gly Ile Pro Leu Phe Ala Ser Gln Leu Ser Met Asp Pro Ser Lys
                165                 170                 175

Arg Lys Lys Val Arg Glu Glu Arg Leu Asn Asn Asn Pro Ile Gly Leu
            180                 185                 190

Arg Gly Ser Leu Ile Gly Met Gly Thr Gly Ser Gln Pro Ser Trp Trp
        195                 200                 205

Asn Lys Leu Ser Gly Ile Asn Tyr Pro Val Leu Leu Ile Ala Gly Ser
    210                 215                 220

Leu Asp Gln Lys Phe Val Ala Ile Asn Glu Ser Met Ala Lys Arg Ile
225                 230                 235                 240

Pro Ala Ala Arg Leu Glu Ile Val Glu His Thr Gly His Ala Val His
                245                 250                 255

Val Glu Glu Pro Asp Phe Phe Gly Arg Ile Val Ser Glu Phe Ile Leu
            260                 265                 270

Lys


<210> SEQ ID NO 19
<211> LENGTH: 273
<212> TYPE: PRT
<213> ORGANISM: Bacillus licheniformis
<220> FEATURE:
<223> OTHER INFORMATION: alpha/beta hydrolase (yugF)

<400> SEQUENCE: 19
```

-continued

```
Met Leu Leu Thr Lys Pro Ser Ile Glu Thr Ile Gln Gly Val Asn Ile
1               5                   10                  15

Tyr Tyr Glu His Tyr Glu Asn Pro Gly Lys Thr Ser Leu Val Leu Ile
            20                  25                  30

His Gly Phe Leu Ser Ser Ser Phe Cys Tyr Arg Lys Ile Ile Pro Leu
        35                  40                  45

Leu Lys Asp Glu Phe Asn Leu Val Ala Val Asp Leu Pro Pro Phe Gly
    50                  55                  60

Gln Ser Glu Lys Ser Ser Thr Phe Val Tyr Thr Tyr Gln Asn Met Ala
65                  70                  75                  80

Arg Val Val Ile Glu Leu Ile Glu Arg Leu Lys Ile Lys Asp Ala Val
                85                  90                  95

Leu Val Gly His Ser Met Gly Gly Gln Ile Ser Leu Tyr Ala Ile Lys
            100                 105                 110

Glu Arg Pro Glu Leu Phe Lys Lys Val Val Leu Leu Cys Ser Ser Gly
        115                 120                 125

Tyr Leu Lys Arg Ser Pro Arg Ser Leu Ile Phe Gly Ser His Ile Pro
    130                 135                 140

Tyr Phe Tyr Leu Tyr Ile Lys Arg Trp Leu Ser Lys Gln Gly Val Leu
145                 150                 155                 160

Lys Asn Leu Met Asn Val Val Tyr Asp Ser Ser Leu Ile Asp Gln Glu
                165                 170                 175

Met Ile Asn Gly Tyr Leu Lys Pro Phe Leu Asp Asp Gln Ile Phe Arg
            180                 185                 190

Ala Leu Ala Arg Leu Ile Arg His Arg Glu Gly Asp Leu Ser Pro Asp
        195                 200                 205

Asp Leu Lys Lys Ile Glu Thr Pro Ser Leu Leu Ile Trp Gly Glu Glu
    210                 215                 220

Asp Arg Val Val Pro Val Gln Ile Gly Lys Arg Leu His Gln Asp Leu
225                 230                 235                 240

Pro Asn Ser Ile Phe Tyr Ser Leu Gln Glu Thr Gly His Leu Val Pro
                245                 250                 255

Glu Glu Asn Pro Asp Tyr Val Ser Asp Lys Ile Ala Asn Phe Ile Leu
            260                 265                 270

Thr


<210> SEQ ID NO 20
<211> LENGTH: 298
<212> TYPE: PRT
<213> ORGANISM: Bacillus licheniformis
<220> FEATURE:
<223> OTHER INFORMATION: dipeptidylpeptidase (unknown)

<400> SEQUENCE: 20

Met Thr Asn His Ile Lys Glu Ile Asn Trp Glu Gln Asn Thr Asn Ser
1               5                   10                  15

Tyr Ile Gln Leu Ile Pro Asn Ile Glu Tyr Thr Lys Val Glu Asp Thr
            20                  25                  30

Ser Leu Thr Leu His Leu Leu Val Tyr Arg Asn Pro Met Asp Ala Leu
        35                  40                  45

Phe Asn Arg Lys Gly Asn Gln Glu Thr Tyr Pro Leu Ile Ile Tyr Leu
    50                  55                  60

Gln Gly Cys Gly Trp Gly Trp Thr Lys Gln Asp Thr Ser Ala Phe Ile
65                  70                  75                  80

Pro Gln Leu Val Pro Phe Val Glu Gln Gly Tyr Val Val Ala Ser Val
```

-continued 85 90 95

Gln Tyr Arg Gly Ser Gly Glu Ala Val Phe Pro Ala Gln Leu His Asp
100 105 110

Val Lys Thr Ala Val Arg Phe Leu Lys Ala Asn Ala Ala Arg Tyr Asn
115 120 125

Ile Asp Pro Asp Arg Val Gly Val Trp Gly Asp Ser Ser Gly Gly His
130 135 140

Leu Ala Leu Leu Leu Gly Leu Thr Glu Gly Ile Glu Glu Phe Glu Gly
145 150 155 160

Pro Asp Glu Tyr Arg His Val Ser Ser Lys Val Asp Ala Val Ala Asp
165 170 175

Trp Phe Gly Pro Val Asp Leu Leu Ser Met Ser Lys Tyr Pro Ser Ile
180 185 190

Phe Asp His Asp Ser Pro Asn Ser Pro Glu Ser Lys Leu Ile Gly Gly
195 200 205

Ala Val Gln Glu Asn Arg Val Gln Ala Lys Gln Ala Ser Pro Ile Ser
210 215 220

Tyr Val His Arg Glu Ala Pro Pro Ile Leu Ile Met His Gly Asp Gln
225 230 235 240

Asp Asp Val Val Pro Tyr Gln Gln Ser Val Gln Leu Phe Glu Ala Leu
245 250 255

Ile Lys Glu Gly His Asp Ala Leu Met Tyr Lys Ile Asn Gly Ala Gly
260 265 270

His Asn Gly Phe Thr Gln Ala His Thr Leu Asp Ile Val Lys Ser Phe
275 280 285

Phe Arg Lys His Leu Lys Pro Gly Lys Ala
290 295

<210> SEQ ID NO 21
<211> LENGTH: 653
<212> TYPE: PRT
<213> ORGANISM: Bacillus licheniformis
<220> FEATURE:
<223> OTHER INFORMATION: putative acylaminoacyl-peptidase (yuxL)

<400> SEQUENCE: 21

Met Lys Gln Leu Ile Thr Glu Lys Asp Leu Ile Lys Leu Val Ser Ile
1 5 10 15

Thr Asp Pro Gln Tyr Ser Pro Asp Gly Ala Lys Ile Ala Tyr Val Gln
20 25 30

Thr Lys Val Asn Glu Lys Gln Asp Ser Tyr Asp Ser His Ile Met Ile
35 40 45

Tyr Asp Arg Glu Lys Gln Ala Ser Val Gln Trp Thr Phe Gly Lys Gly
50 55 60

Arg Asn Gln His Pro Arg Trp Ser Pro Asp Gly Lys Tyr Leu Ala Phe
65 70 75 80

Thr Ser Asn Arg Glu Glu Thr Ala Gln Ile Tyr Val Ile Ser Ala Ala
85 90 95

Gly Gly Glu Ala Arg Lys Val Thr Asp Ile Pro Tyr Asp Val Ser Gln
100 105 110

Pro Glu Trp Ser Pro Asp Gly Lys Ser Leu Leu Cys Ser Val Lys Leu
115 120 125

Thr Lys Glu Glu Ser Val Asp Asp Glu Lys Lys Thr Glu Ile Glu Asp
130 135 140

His Glu Pro Leu Glu Val Asp Ser Leu Ser Tyr Lys Ala Asp Gly Gln

-continued

```
145                 150                 155                 160

Gly Phe Lys Arg Gly Lys Tyr Thr Gln Leu Val Leu Val Gln Val Glu
                165                 170                 175

Thr Gly Glu Met Lys Gln Leu Thr Asp Leu Glu Arg Asp His Phe Ser
            180                 185                 190

His Ala Phe Ser Pro Cys Gly Asp Gln Ile Ala Phe Cys Ala Asn Gln
        195                 200                 205

Thr Asp Met Arg Val Asn Asp Val Tyr Leu Met Asn Leu Ser Thr Gly
    210                 215                 220

Asp Leu Lys Arg Leu Thr Gly Gln Asn Gly Ile Phe Ser Ser Leu Ser
225                 230                 235                 240

Phe Ser Pro Asp Gly Lys His Leu Ala Phe Ile Gly Asn Glu Lys Glu
                245                 250                 255

Tyr Gln Asn Ala Thr Leu Asp Lys Ala Trp Leu Tyr Asp Ile Glu Thr
            260                 265                 270

Gly Lys Leu Thr Cys Leu Thr Glu Met Leu Asp Val His Leu Ser Asp
        275                 280                 285

Ala Val Ala Gly Asp Ser Leu Val Gly Gly Val Leu Pro Lys Pro Ala
    290                 295                 300

Trp Thr Lys Asp Gly Asn Gly Phe Tyr Val Ile Gly Ser Asp Gln Gly
305                 310                 315                 320

Ser Thr Gly Ile Tyr Tyr Ile Ser Ile Glu Gly Leu Ala Tyr Pro Val
                325                 330                 335

Arg Leu Glu Lys Glu His Val Asn Gly Phe Ser Leu His Pro Asp Glu
            340                 345                 350

Ser Gly Phe Ala Ala Ser Ile Ala Leu Pro Val Arg Pro Ser Glu Leu
        355                 360                 365

Tyr His Leu Gln Leu Gly Glu Glu Lys Ala Glu Arg Leu Thr Asp Ala
    370                 375                 380

Asn Gln Ala Phe Thr Glu Glu His Ile Ile Ser Glu Pro Glu Glu Leu
385                 390                 395                 400

Gln Phe Gln Ala Ala Asp Gly Leu Thr Ile His Gly Trp Leu Ile Lys
                405                 410                 415

Pro Ala Gln Tyr Glu Lys Gly Asn Thr Tyr Pro Leu Ile Leu Glu Val
            420                 425                 430

His Gly Gly Pro His Ala Met Tyr Ala Asn Ala Tyr Phe His Glu Phe
        435                 440                 445

Gln Val Leu Ala Ala Lys Gly Ser Ala Val Val Tyr Val Asn Pro Arg
    450                 455                 460

Gly Ser His Gly Tyr Gly Gln Asp Phe Val Asn Arg Val Arg Gly Asp
465                 470                 475                 480

Tyr Gly Gly Gly Asp Phe Lys Asp Val Met Ala Ala Val Asp His Val
                485                 490                 495

Leu Glu His Tyr Asp Phe Val Asp Gln Glu Arg Leu Gly Ile Thr Gly
            500                 505                 510

Gly Ser Tyr Gly Gly Phe Met Thr Asn Trp Ala Val Gly His Thr Lys
        515                 520                 525

Arg Phe Lys Ala Ala Val Thr Gln Arg Ser Ile Ser Asn Trp Ile Ser
    530                 535                 540

Phe Tyr Gly Val Ser Asp Ile Gly Tyr Phe Phe Thr Asp Trp Gln Leu
545                 550                 555                 560

Gly Ala Asp Leu Phe Glu Asp Pro Gly Lys Leu Trp Glu His Ser Pro
                565                 570                 575
```

Leu Lys Tyr Ala Asp Lys Val Glu Thr Pro Leu Leu Ile Leu His Gly
580 585 590

Glu Arg Asp Asp Arg Cys Pro Ile Glu Gln Ala Glu Gln Leu Phe Thr
595 600 605

Ala Leu Lys Lys Met Gly Lys Glu Val Lys Leu Val Arg Phe Pro Asn
610 615 620

Ala Ser His Asp Leu Ser Arg Ser Gly His Pro Lys Gln Arg Ile Arg
625 630 635 640

Arg Leu Glu Tyr Ile Ala Gly Trp Phe Glu Ala Tyr Leu
645 650

<210> SEQ ID NO 22
<211> LENGTH: 479
<212> TYPE: PRT
<213> ORGANISM: Bacillus licheniformis
<220> FEATURE:
<223> OTHER INFORMATION: phage putative hydrolase protein (unknown)

<400> SEQUENCE: 22

Met Ser Lys Lys Ile Lys Lys Ser Asn Leu Thr Asp Glu Thr Tyr Tyr
1 5 10 15

Arg Ile Ser Gln Arg Ser Tyr Asn Tyr Asp Tyr Leu Arg Lys Lys Leu
20 25 30

Lys Asn Lys Glu Tyr Ile Arg Ile Asn Ser Ser Val Ser Gly Ala Thr
35 40 45

Tyr Trp Tyr Val Asp Lys Ile Lys Thr Asp Glu Asp Thr Gly Leu Asp
50 55 60

Ala Ala Val Leu Ser Gln Ala Glu Asn Lys Asn Gly Lys Trp Val Lys
65 70 75 80

Ser Asp His Pro Lys Asn Val Val Val Ala Phe Ala Gly Thr Asp Pro
85 90 95

Gly Lys Asp Pro Leu Ser Asp Val Glu Gln Ala Asp Ile Asn His Ile
100 105 110

Val Leu Gly Asn Asp Pro Lys Asp Lys Thr Gln Tyr Val Val Lys Lys
115 120 125

Asp Ala Lys Asp Met Ser Lys Thr Phe Gly Arg Tyr Ile Gly Ser Met
130 135 140

Glu Gln Thr Ala Met Leu Glu Ser Gly Asp Tyr Lys Leu Ile Thr Lys
145 150 155 160

Thr Ser Gln Ile Asp Gln Ala Asp Gln Leu Val Arg Glu Val Lys Gln
165 170 175

Lys Tyr Lys Gly Thr Ser Thr Val Ile Ser Thr Thr Gly His Ser Leu
180 185 190

Gly Gly Ala Glu Ala Glu Tyr Ser Ala Val Asn Asn Asp Ile Tyr Ala
195 200 205

Val Ala Phe Asn Ser Pro Ser Ile Val His Leu His Ser Asp Glu Lys
210 215 220

Gln Lys Glu Ile Asn Asn Gly Asp Tyr Asn Ser Tyr Val Lys Ser Ile
225 230 235 240

Ile Asn Pro Asp Asp Met Val Gly Ala Gly Trp Trp Asp Glu Phe Asp
245 250 255

Arg His Asn Gly Thr Thr Ile Tyr Thr Lys Asp Pro Ser Ile Ala Thr
260 265 270

Ala Asn Arg Glu Glu Arg Leu Asp Gly Asn Lys Leu Gln Gln Val Gly
275 280 285

Arg Asn Leu Leu Tyr Phe Ala Asn Thr Leu Ile Phe Gln Asn Pro Asp
    290                 295                 300

Thr His Gly Ile Asn Lys Ser Asn Phe Ser Phe Asp Glu Asn Gly Asn
305                 310                 315                 320

Val Gln Asn Ile Glu Gly Asp Glu Leu Val Tyr Asp Lys Asn Leu Lys
                325                 330                 335

Ala Met Leu Pro Pro Glu Val Ala Ser Gly Ser Gly Ala Ile Lys Val
            340                 345                 350

Thr Pro Glu Val Ala Lys Gln Leu Ala Gln Lys Val Asn Ala Ile Ile
        355                 360                 365

Asp Asp Leu Arg Thr Met Lys Arg Glu Ala Glu Asn Ala Tyr Gln Glu
    370                 375                 380

His Asp Ala Glu Ile Asn Asp Leu Lys His Asp Thr Tyr Arg Gln Val
385                 390                 395                 400

Gly His Gly Leu Tyr Asp Lys Leu Thr Leu Glu Asp Val Asn Asn Thr
                405                 410                 415

Leu Lys Asn Leu Ala Gln Ser Phe Asp Lys Lys Gly Asn Pro Leu Phe
            420                 425                 430

Tyr Asp Val His Ala Glu Lys Ala Tyr Ile Ala Ser Leu Lys Asn Thr
        435                 440                 445

Ile Ser Asp Leu Glu Asp Ile Ser Gly Tyr Leu Ala Gln Ile Ala Lys
    450                 455                 460

Asp Phe Lys Ser Lys Asp Lys Met Leu Ala Asn Trp Leu Lys Leu
465                 470                 475

<210> SEQ ID NO 23
<211> LENGTH: 282
<212> TYPE: PRT
<213> ORGANISM: Bacillus licheniformis
<220> FEATURE:
<223> OTHER INFORMATION: trilactone hydrolase (besA)

<400> SEQUENCE: 23

Met Ala Gln Glu Lys Leu Gln Gln Ser Val Asn Ala Ala Glu Cys Ile
1               5                   10                  15

Pro Val Ala Ile Pro Gly Thr Glu Gln Arg Cys Met Arg Ser Leu Asp
            20                  25                  30

Gly Ser Arg Thr Tyr Arg Ile Phe Ile Ala Lys Pro Phe Gly Glu Gln
        35                  40                  45

Pro Pro Ala Gly Tyr Pro Val Ile Tyr Leu Leu Asp Ala Asn Ser Val
    50                  55                  60

Phe Gly Thr Met Val Glu Ala Leu Arg Met Gln Ser Arg Arg Pro Asp
65                  70                  75                  80

Lys Thr Gly Val Gly Thr Ala Val Ile Val Gly Ile Gly Tyr Glu Thr
                85                  90                  95

Asp Ala Pro Phe Asp Arg Gly Arg Tyr Tyr Asp Phe Thr Leu Pro Glu
            100                 105                 110

Ser Gly Ala Glu Leu Pro Met Arg Pro Asp Gly Ala Asp Trp Pro Glu
        115                 120                 125

Pro Gly Gly Ala Lys Ala Phe Leu Ser Phe Ile Glu Gln Gln Leu Lys
    130                 135                 140

Pro Glu Ile Glu Gln Glu Phe Thr Ile Asp Val Lys Arg Gln Ala Ile
145                 150                 155                 160

Phe Gly His Ser Leu Gly Gly Leu Phe Val Leu Gln Thr Leu Phe Thr
                165                 170                 175

-continued

```
Lys Pro Asp Leu Phe Gln Thr Tyr Ile Ala Gly Ser Pro Ser Ile His
            180                 185                 190

Trp His Pro Ser Phe Phe Asp Lys Glu His Asp Phe Val Ser Lys Leu
        195                 200                 205

Gln Glu Ala Asp Gly Asp Val Lys Val Leu Leu Gly Ala Gly Glu Leu
    210                 215                 220

Glu Lys Thr His Lys Ser Gly Met Asn Asp Asn Ala Lys Arg Leu Ala
225                 230                 235                 240

Asp Arg Leu Ala Ala Leu Glu Ser Gln Gly Val Arg Ala Glu Tyr His
                245                 250                 255

Glu Phe Lys Gly Glu Gly His Ile Ser Val Leu Pro Val Leu Ile Ser
            260                 265                 270

Arg Ala Leu Arg Phe Ala Phe Lys Pro Asp
        275                 280


<210> SEQ ID NO 24
<211> LENGTH: 220
<212> TYPE: PRT
<213> ORGANISM: Bacillus licheniformis
<220> FEATURE:
<223> OTHER INFORMATION: rhamnogalacturonan acetylesterase (unknown)

<400> SEQUENCE: 24

Met Met Arg Asp Ile Gln Leu Phe Leu Ala Gly Asp Ser Thr Val Cys
1               5                   10                  15

Asp Tyr Asp Glu Asn Arg Ala Pro Arg Ala Gly Trp Gly Gln Lys Ile
            20                  25                  30

Gly Glu Phe Leu Ser Ala Gly Val Leu Ile Arg Asn Glu Ala Ala Ser
        35                  40                  45

Gly Arg Ser Ser Lys Ser Phe Ile Glu Glu Gly Arg Leu Lys Arg Ile
    50                  55                  60

Ile Thr Gln Ile Lys Ser Gly Asp Tyr Leu Phe Val Gln Phe Gly His
65                  70                  75                  80

Asn Asp Gln Lys Pro Asp Asp Arg Tyr Thr Glu Pro Tyr Thr Thr Tyr
                85                  90                  95

Lys Gln His Leu Thr Arg Tyr Ile Asp Glu Ala Arg Leu Lys Lys Ala
            100                 105                 110

Asn Pro Val Leu Ile Thr Pro Val Gln Arg Arg Ser Phe Ala Ser Asp
        115                 120                 125

Gly Arg Phe Lys Asn Thr His Gly Asp Tyr Pro Asp Ala Met Ile Gln
    130                 135                 140

Leu Ala Glu Glu Leu Arg Val Pro Leu Ile Asp Leu Ala Phe Lys Ser
145                 150                 155                 160

Arg Gln Leu Leu Glu Ser Leu Gly Pro Glu Ala Ser Lys Lys Leu Tyr
                165                 170                 175

Leu Trp Leu Glu Pro Gly Glu His Pro Asn Tyr Pro Asp Gly Ala Arg
            180                 185                 190

Asp Asp Thr His Phe Cys Asp Phe Gly Ala Lys Glu Ile Ala Lys Leu
        195                 200                 205

Val Ala Gln Glu Ala Lys Glu Ala Gly Ile Pro Leu
    210                 215                 220


<210> SEQ ID NO 25
<211> LENGTH: 246
<212> TYPE: PRT
<213> ORGANISM: Bacillus licheniformis
```

-continued

<220> FEATURE:
<223> OTHER INFORMATION: lichenysin synthase (lchAD)

<400> SEQUENCE: 25

```
Met Asn Glu Ile Ile Lys Gln Phe Gly Ala Pro Ala Ser Gly Met Gln
1               5                   10                  15

Leu Ile Cys Phe Pro Phe Ala Gly Gly Tyr Ser Ala Ser Phe Arg Pro
            20                  25                  30

Leu His Glu His Leu Lys Thr Asp Phe Asp Met Leu Ala Ile Glu Pro
        35                  40                  45

Pro Gly His Gly Thr Asn Arg Met Ala Leu Val Asp Asn Leu Glu Lys
    50                  55                  60

Leu Ala Asp Leu Tyr Ile Ala Ala Leu Lys Pro Arg Leu Ser Ser Gln
65                  70                  75                  80

Phe Val Leu Phe Gly His Ser Met Gly Gly Met Val Val Tyr Arg Leu
                85                  90                  95

Ala Gln Lys Leu Glu Gln Glu Gly Ile Phe Pro Ala Ala Ala Val Ile
            100                 105                 110

Ser Ala Ile Gln Pro Pro His Ile Gln Arg Gln Lys Val Ser His Gln
        115                 120                 125

Lys Asp Asp Ala Phe Leu Asp His Leu Ile Gln Leu Gly Gly Ile Pro
    130                 135                 140

Lys Glu Leu Ala Glu His Arg Glu Met Met Asn Phe Phe Leu Pro Ser
145                 150                 155                 160

Phe Arg Ala Asp Tyr Arg Ala Leu Glu Thr Phe Cys His Thr Asp His
                165                 170                 175

Thr Pro Leu Arg Ser Pro Val His Ile Leu Asn Gly Asp Arg Asp Glu
            180                 185                 190

Lys Cys Met Arg Asp Ala Leu Gly Trp Lys Lys Trp Ala Asn Thr Ile
        195                 200                 205

Asp Phe His Tyr Phe Lys Gly Gly His Met Tyr Leu Leu Ser Glu Thr
    210                 215                 220

Glu Gln Val Ala Ala Lys Leu Lys Thr Ile Ala Ala Ala Ser Arg Ser
225                 230                 235                 240

Thr Ala Val Pro Thr Met
                245
```

<210> SEQ ID NO 26
<211> LENGTH: 271
<212> TYPE: PRT
<213> ORGANISM: Bacillus licheniformis
<220> FEATURE:
<223> OTHER INFORMATION: putative esterase (unknown)

<400> SEQUENCE: 26

```
Met Ile Leu Val Gln Asn Gly Val Met Asn Met Ile Asp Gly Thr Leu
1               5                   10                  15

Ile Lys Asp Thr Cys Phe Gly Arg Glu Leu Leu Ile Tyr Leu Pro Pro
            20                  25                  30

Ser Tyr Gly Ser Gly Glu Asn Arg Tyr Pro Val Leu Tyr Val His Asp
        35                  40                  45

Leu Gly Asp Leu Phe Asp Pro Ala Tyr Ser Asn Ser Leu Arg Ser Ile
    50                  55                  60

Glu Lys Leu Phe Ser Ser Gln Glu Val Pro Glu Leu Leu Leu Val Gly
65                  70                  75                  80

Val Ala Pro Lys Asp Arg Glu Ser Glu Tyr Thr Pro Phe Pro Lys Arg
```

-continued 85 90 95

His Leu Leu Pro Asn Lys Arg Glu Tyr Gly Gly Lys Gly Asn Glu Tyr
100 105 110

Ala Ala Phe Leu Ala Asn Arg Leu Lys Pro His Ile Asp Arg His Tyr
115 120 125

Arg Thr Asn Pro Ser Arg Glu Gln Thr Gly Ile Ile Gly Lys Ser Phe
130 135 140

Gly Gly Leu Ile Ser Val Tyr Thr Ala Phe Leu Ala Ser Glu Thr Phe
145 150 155 160

Gly Lys Ile Gly Ser Leu Ser Gly Ser Phe Trp Phe Glu Gly Ile Thr
165 170 175

Glu Phe Met Lys Asn Asn Arg Phe Glu Asn Lys His Leu Arg Ile Tyr
180 185 190

Met Asp Val Gly Ser Thr Glu Gly Thr Asp Arg Asp Asn Leu Gln Lys
195 200 205

Glu Met Ile Pro Arg Thr Lys Glu Ala Phe Ser Leu Leu Thr Glu Ser
210 215 220

Ala Ala Ser Glu Lys Glu Leu Lys Phe Val Ile Asp Glu Gly Gly Ser
225 230 235 240

His Arg Leu Glu Arg Phe Ala Lys Arg Phe Pro Glu Ala Val Lys Trp
245 250 255

Leu Phe Gly Ser Cys His Asn Ser Ala Arg Asn Gly Arg Ser Phe
260 265 270

<210> SEQ ID NO 27
<211> LENGTH: 212
<212> TYPE: PRT
<213> ORGANISM: Bacillus licheniformis
<220> FEATURE:
<223> OTHER INFORMATION: spore germination lipase LipC (lipC)

<400> SEQUENCE: 27

Met Thr Leu Gln Tyr Thr Ala Leu Gly Asp Ser Leu Thr Val Gly Val
1 5 10 15

Gly Ala Gly Leu Phe Glu Pro Gly Phe Val Gln Arg Tyr Lys Arg Lys
20 25 30

Met Glu Glu Asp Leu Asn Glu Glu Val Ser Leu Ile Val Phe Ala Lys
35 40 45

Ser Gly Leu Glu Thr Ser Glu Ile Leu Ala Met Leu Asn Glu Pro Phe
50 55 60

Ile Met Glu Gln Val Lys Lys Ala Asp Val Ile Thr Ile Thr Gly Cys
65 70 75 80

Gly Asn Asp Leu Leu Gln Ser Leu Glu Ile Tyr Glu Lys Glu Lys Asp
85 90 95

Glu His Val Phe Leu Glu Ala Ser Ser His Cys Gln Lys Asn Tyr Ser
100 105 110

Gly Met Leu Glu Lys Ile Arg Glu Ile Lys Gly Glu Lys Asp Thr Arg
115 120 125

Tyr Leu Val Arg Leu Leu Asn Leu Tyr Asn Pro Phe Pro Ser Ile Glu
130 135 140

Leu Ala Asp Lys Trp Ile Ser Gly Phe Asn Arg His Leu Lys Gln Leu
145 150 155 160

Glu Ser Ala Pro Gln Ile Lys Val Ile Asp Thr Tyr Ala Val Phe Lys
165 170 175

Gly Arg Glu Lys Glu Tyr Leu Ser Ile Asp Arg Val His Pro Ser Ser

```
            180                 185                 190

Arg Gly Tyr Glu Ala Met Ser Glu Lys Leu Arg Ala Ala Gly Tyr Gly
        195                 200                 205

Arg Leu Glu Gly
    210


<210> SEQ ID NO 28
<211> LENGTH: 236
<212> TYPE: PRT
<213> ORGANISM: Bacillus licheniformis
<220> FEATURE:
<223> OTHER INFORMATION: putative esterase/lipase (unknown)

<400> SEQUENCE: 28

Met Ile Gly Cys Leu Cys Ile His Gly Phe Thr Gly Ala Pro Tyr Glu
1               5                   10                  15

Leu Glu Pro Leu Ala Ser His Leu Lys Gln Thr Ala Asp Trp Gln Val
            20                  25                  30

Glu Met Ile Thr Leu Pro Gly His Gly Glu Met Pro Val Leu Lys Gly
        35                  40                  45

Val Cys Phe Gln Glu Trp Ile Ala Cys Ala Glu Val Glu Leu Ile Arg
    50                  55                  60

Leu Leu Lys Thr Cys Asp Thr Val Phe Leu Ile Gly Phe Ser Met Gly
65                  70                  75                  80

Gly Met Ile Ala Gly Tyr Leu Ala Gly Lys Tyr Pro Val Ser Arg Leu
                85                  90                  95

Val Leu Leu Ser Ala Ala Ala Gln Tyr Ile Ser Pro Gly Gln Leu Ile
            100                 105                 110

Gln Asp Leu Lys Asn Val Ile Lys Asp Ser Leu Gln Gly Lys Leu Glu
        115                 120                 125

Asp Asn Leu Leu Tyr Lys Arg Tyr Lys Gln Lys Leu Thr Ser Thr Pro
    130                 135                 140

Val Ser Ser Ala Phe Gln Phe Arg Lys Leu Val Lys Met Thr Lys Pro
145                 150                 155                 160

Ala Leu Lys Asn Leu Arg Ile Pro Val Leu Ile Val Gln Gly Glu Cys
                165                 170                 175

Asp Ala Ile Val Pro Val Ser Ser Ala Tyr Tyr Leu Tyr Glu Thr Ile
            180                 185                 190

Pro Ser Glu Glu Lys Glu Leu Cys Leu Leu Pro Glu Ser Lys His His
        195                 200                 205

Val Cys Leu Glu Glu Asn Ser Ser Ile Leu Phe Gln Thr Val Glu Ala
    210                 215                 220

Phe Leu Lys Lys Thr Pro Ile Glu Ser Ile Lys Lys
225                 230                 235


<210> SEQ ID NO 29
<211> LENGTH: 626
<212> TYPE: PRT
<213> ORGANISM: Bacillus licheniformis
<220> FEATURE:
<223> OTHER INFORMATION: putative peptidoglycan O-acetyltransferase
      (yrhL)

<400> SEQUENCE: 29

Met Arg Asp Gln Thr Gln Gln His Arg Tyr Ile Pro Gly Leu Asp Gly
1               5                   10                  15

Leu Arg Ala Phe Ala Val Leu Ala Val Ile Ala Tyr His Leu Asn Met
            20                  25                  30
```

-continued

Ser Trp Ala Asp Gly Gly Phe Ile Gly Val Asp Ile Phe Phe Val Leu
35 40 45

Ser Gly Tyr Leu Ile Thr Ser Ile Ile Leu Pro Ala Tyr Gly Asn Asp
50 55 60

Ile Ser Leu Thr Phe Arg Asp Phe Trp Val Arg Arg Ile Arg Arg Leu
65 70 75 80

Leu Pro Ala Ala Thr Leu Met Ile Phe Ala Thr Val Ile Trp Val Ala
85 90 95

Leu Phe Asn Arg Glu Leu Met His Thr Val Arg Gly Asp Ala Ile Ser
100 105 110

Ser Leu Leu Tyr Val Ser Asn Trp Trp Phe Ile Phe His Asp Leu Ser
115 120 125

Tyr Phe Asp Ser Phe Gly Ser Pro Ser Pro Leu Lys Asn Leu Trp Ser
130 135 140

Leu Ala Ile Glu Glu Gln Phe Tyr Phe Ile Trp Pro Ile Ile Leu Leu
145 150 155 160

Leu Gly Ile Tyr Ile Phe Lys Lys Arg Glu Arg Phe Ala Ala Ala Val
165 170 175

Val Leu Cys Ala Leu Cys Ser Ala Ile Trp Met Ser Ile Leu Tyr Val
180 185 190

Pro Gly Gly Asp Pro Ser Arg Val Tyr Tyr Gly Thr Asp Thr Arg Ala
195 200 205

Phe Glu Leu Leu Ile Gly Cys Ala Leu Ala Leu Val Trp Pro Met Lys
210 215 220

Arg Leu Ser Gly Asn Arg Leu Pro Asn Ser Leu Lys His Ala Leu His
225 230 235 240

Gly Thr Glu Leu Ala Ala Phe Ala Leu Leu Met Met Cys Ile Tyr Phe
245 250 255

Val Asp Glu Phe Ser Pro Phe Leu Tyr His Gly Gly Met Leu Ile Ile
260 265 270

Ser Ile Ile Ala Ala Ile Leu Ile Ala Cys Val Ser His Pro Ser Ser
275 280 285

Phe Leu Gly Phe Ala Leu Ser Val Lys Pro Leu Arg Trp Ile Gly Lys
290 295 300

Arg Ser Tyr Gly Ile Tyr Leu Trp His Tyr Pro Val Ile Val Leu Ser
305 310 315 320

Thr Pro Val Gln Glu Ile Gly Asn Pro Val Tyr Trp His Val Ala Met
325 330 335

Lys Val Ala Val Thr Phe Ile Leu Ala Glu Leu Ser Tyr Arg Phe Ile
340 345 350

Glu Lys Pro Ile Arg Lys Asp Gly Phe Lys Pro Phe Val Ser Arg Val
355 360 365

Phe Leu Asp Lys Ile Thr Glu Trp Lys Thr Ala Ser Val Pro Ser Lys
370 375 380

Ile Ser Ile Gly Leu Met Phe Ala Ala Leu Leu Val Phe Ala Gly Gly
385 390 395 400

Leu Ser Gly Leu Ala Asp Glu Lys Lys Gln Pro Gln Gln Ala Tyr Ser
405 410 415

Lys Ser Tyr Glu Glu Thr Ser Ala Ser Ala Asp Gln Pro Ala Asp Lys
420 425 430

Ser Glu Glu Arg Gln Asp Asp Lys Lys Ala Gln Thr Glu Ser Gly Asn
435 440 445

-continued

Glu Ser Lys Thr Gly Asn Gly Glu Glu Ser Ser Asp Thr Lys Asp Glu
    450                 455                 460

Gln Ser Ala Glu Lys Glu Pro Asp Arg Ile Glu Lys Glu Val Leu Ala
465                 470                 475                 480

Val Gly Asp Ser Val Met Leu Asp Ile Ala Ser Ser Leu Arg Arg Lys
                485                 490                 495

Ile Pro Gly Ile Thr Ile Asp Gly Gln Val Gly Arg Gln Val Arg Glu
            500                 505                 510

Ala Leu Gln Leu Thr Ser Thr Tyr Ala Ser Phe Asn His Pro Asp Lys
        515                 520                 525

Ala Val Val Ile Glu Leu Gly Thr Asn Gly Tyr Phe Thr Asp Gly Gln
    530                 535                 540

Leu Asp Ala Leu Leu Asp Ala Phe Ser Lys Ala Asp Val Tyr Leu Val
545                 550                 555                 560

Asn Thr Arg Val Pro Arg Gln Trp Glu Ser Lys Val Asn Glu Ser Leu
                565                 570                 575

Arg Lys His Ala Asp Ser Arg Gln Asn Val Thr Leu Val Asp Trp His
            580                 585                 590

Ala Glu Ala Leu Gln His Pro Glu Tyr Phe Thr Ala Asp Gly Val His
        595                 600                 605

Leu Met Pro Lys Gly Ala Glu Ala Leu Ala Ser Leu Ile Val Lys Ala
    610                 615                 620

Met Lys
625

<210> SEQ ID NO 30
<211> LENGTH: 303
<212> TYPE: PRT
<213> ORGANISM: Bacillus licheniformis
<220> FEATURE:
<223> OTHER INFORMATION: hypothetical protein (unknown)

<400> SEQUENCE: 30

Met Trp Ile Gly Ile Leu Leu Met Val Ser Gly Ile Gly Ile Ser Ile
1               5                   10                  15

Phe Ala Val Ser Leu Ile Val Ser Tyr Leu Phe Val Leu Pro Asn Arg
            20                  25                  30

Ser Thr Tyr Glu Glu Thr Phe Phe Ser Gly Leu Lys His Gly Glu Ile
        35                  40                  45

Ile Asp Asp Val Phe Glu Ser His Asp Lys Glu Glu Leu Phe Leu Thr
    50                  55                  60

Ala Gly Asp Gly Cys Arg Leu His Ala Leu Leu Phe Pro Val Gln Lys
65                  70                  75                  80

Ser Arg Lys Ala Val Ile Ile Ser His Gly Ile Lys Trp Ser Leu Phe
                85                  90                  95

Gly Gly Tyr Lys Tyr Val Glu Leu Phe Gln Ser Ile Gly Tyr Asn Val
            100                 105                 110

Leu Leu Cys Asp Ser Arg Cys His Gly Leu Ser Gly Gly Ser His Val
        115                 120                 125

Ser Tyr Gly Phe Tyr Glu Lys Asp Asp Leu Ala Arg Trp Ala Asp Glu
    130                 135                 140

Leu Glu Asn Arg Phe Gly Lys Asp Leu Trp Ile Gly Val Leu Gly Glu
145                 150                 155                 160

Ser Leu Gly Ala Ala Ala Ala Ile Glu Leu Met Lys Gln Asp Arg Arg
                165                 170                 175

-continued

```
Ile Lys Phe Cys Ile Ala Asp Ser Cys Phe Ser Asp Leu Thr Glu Leu
            180                 185                 190

Cys Arg Phe Gln Leu Lys Ala Ala Val Lys Leu Ser Val Pro Phe Leu
        195                 200                 205

Ile Pro Leu Ala Ser Gly Leu Ile Lys Arg Arg His Gly Trp Ser Leu
    210                 215                 220

Ala Asp Ile Ser Pro Val Ser Asn Leu Glu Gln Ser Asp Thr Pro Leu
225                 230                 235                 240

Leu Ile Ile His Gly Thr Lys Asp Gln Leu Val Pro Pro Glu Met Ala
                245                 250                 255

Lys Ser Leu Tyr Glu Arg Lys Lys Gly Phe Lys Lys Leu Tyr Trp Ile
            260                 265                 270

Glu Gly Ala Gly His Val Gly Gly Phe Arg His Asn Pro Glu Glu Tyr
        275                 280                 285

Leu Asn Lys Ile Lys Asp Phe Ile Leu Lys Ile Glu Pro Ala Asn
    290                 295                 300
```

<210> SEQ ID NO 31
<211> LENGTH: 573
<212> TYPE: DNA
<213> ORGANISM: Bacillus licheniformis
<220> FEATURE:
<223> OTHER INFORMATION: putative phosphatase (yhfR)

<400> SEQUENCE: 31

```
atgactgcga tttgtttgat ccggcacggc gagacggact ggaatgcttt aggaaaactg     60

cagggaagaa cagatatccc tttaaatgaa accggtaaaa aacaagcaaa agaaaccggg    120

gcgtttttga aagggtccga ctgggacgtc atcattacaa gccctttaag aagagcgaaa    180

gaaaccgctg aaatcatcaa tcaatacctc ggacttgaaa tcatcgaaat ggaggatttc    240

atcgagagga attacggaga tgcagaagga atgccattcg aagaaagaat gaggctctat    300

cctgataaag aatatccgaa tcaggaatca aaagaagcgc ttgccgaacg gctgatggcc    360

ggcgttcaaa aggtcagtga gcggtatccg gacaaaaaag tgctgatcgt cgcacacgga    420

gccgcgatac acgcgcttct gtcaaaaatc tcaaacggcg acatcaacct ggaaaacacg    480

aagctcgtca atgcctgcct aagcaacatc aaatttcatg aaaataaatg gcatgtgaag    540

gattacaacc tttcacacca tttgtcagat taa                                 573
```

<210> SEQ ID NO 32
<211> LENGTH: 768
<212> TYPE: DNA
<213> ORGANISM: Bacillus licheniformis
<220> FEATURE:
<223> OTHER INFORMATION: putative peptidase (yitV)

<400> SEQUENCE: 32

```
gtgatcataa tcgaaaagca gcatatttca aacattcctc ttttgcatat tgtaaaagag     60

gagaaaaaag agaaagctct tcctcttgtt ttcttcatac atggttttac aagcgcaaaa    120

gagcataacc ttcacttcgc atacctgctt gccgaaaaag gaatgcgcgt gattctgccc    180

gaggctctct atcacgggga aaggaatgaa cagctcaccc aggaagagct cgccccgaga    240

ttttgggaga tcgtcacgaa tgaaatcaaa gagctggaag tgctgaaaaa ccactttgaa    300

cgggaaaaca tgattgaaaa gggccgcatc ggcgccgccg gaacatcgat gggcggcatt    360

gtcacgctcg gcgctttgac tcaatacgaa tggattacaa ctgccgtcag tttaatgggc    420

agtcccgcct atgtagaatt ttttgatcag cagctcgcat ttatgcgtga aaagaaaatt    480
```

-continued gaacttccta tcacagaaga acaaatcgat cagcagcgcg aagaactgaa gcgttttgac 540
ttgagtctgc agccggacaa attgaacatg aggccgcttt tattttggca cggcaaacag 600
gacggcaccg ttccatttgc tttaacgcgc cgcttctatg aatcgattat tccactgtat 660
gaagctcggc ctgatttgct gcattttatc gaagatgagc gggccggaca taaagtatcg 720
agggaaggcc ttttgaaaac agtcgaatgg tttgacgcgc acttgtaa 768

<210> SEQ ID NO 33
<211> LENGTH: 717
<212> TYPE: DNA
<213> ORGANISM: Bacillus licheniformis
<220> FEATURE:
<223> OTHER INFORMATION: rhamnogalacturonan acetylesterase (yesT)

<400> SEQUENCE: 33
atgaaacgaa cagacaaaaa accgaaagtg acagtatatt tggccgggga ctcgaccgtc 60
gcagactgtc ccccgcatga agcgccgatg gccggctggg ggcagatgct tccgctgttt 120
ttctcagatg aggctgcggt cgtgaatatg gcaaaaggcg gggccagttc gaacagcttc 180
attgatgaag gccggctcga tgacattacg gagcggcttg cgcctggtga ttatgtgttg 240
atccagttcg gccacaacga tcaaaaaccg tacggaacag acccttatac aacctatcag 300
gagcatcttg tccgctatgt ggaagcggtt cgcgaaaaac aagcgacacc ggttttgatc 360
acttccgcag agcgcagacg ttttgatcaa aacggaaagc ccgccgacac actcggggat 420
tttccgaaag cgatgaaggc gctcgctgac agcttcgacg ttccgctgat cgatttatgg 480
tccaaaacaa aagcgctcta tgaatctctc ggaatcgaag gttcaaaacg gctgtttgtc 540
cactttcagc ctcatgagca ccctcattat ccaaatggaa tcgaagacaa tacccatttt 600
tccgaagcag gggcccgtca agtcgccagg ctggtgacag aaggaatcag agagcttggt 660
ctgcctctat cggcttatct gctttgtgaa aggagcgatt tccgtgccgg agtgtaa 717

<210> SEQ ID NO 34
<211> LENGTH: 1266
<212> TYPE: DNA
<213> ORGANISM: Bacillus licheniformis
<220> FEATURE:
<223> OTHER INFORMATION: putative carbohydrate esterase (unknown)

<400> SEQUENCE: 34
atgccgaagg agaaaaaatg gggacgatcc cggccggagc aaagggaagc tcagccgaaa 60
aagcgttcac cgtttcggtg gaagacgggc gcctcgatct ggagtgaagg ggcctcagcc 120
aaaggtgtat gccatcgaaa tttcgaggtg tatcagttcg atttcggtga cgggcctctt 180
gcttcgggtt ttattccggt aggcgctgct tcggcctata cccctctaaa aggctacgga 240
tttgacgacg cggcaaaggt gtcctgcacg gaccgaggta cggccgaccc gcttcgttca 300
gacttctgca ttccggatgg gacggcgttt actgtcgatt tgcctgacgg tcaatatcaa 360
gtccaaatca taaccggaga tgcgcgggca aagacgaaca tggacgtacg ggcaaacggc 420
atgctccagc tgtattcgtt tggagcggaa gcgggcggat acaacgaaaa aacgtttccg 480
attcatattt ccggcggccg tctttcgatc caagccttaa cggcgagaac aatgccgcgc 540
cttaatgcgt tggtcattac gaagacggct tatcatgtga cggatgacaa cacgacggtc 600
tttctggcgg gcgattccac ggtctccgat tatgagcccg gctatgcgcc gatggcaggc 660
tgggggcaat tttaggcgg ctatttctcg gatgaaatcg tcatcgacaa ccaggcgaaa 720

-continued cgcgcgagaa gcgcgaaaag ttttgtggat gaacggtcgc tggctacgat tttgaaccgg 780
atgaaacggg gcgactattt gttgattcag ttcggcatta atgacgcagg gcaagatcct 840
gcccgccata cagatccgta tacgacattt caggaatact tgagaacata tattaacaaa 900
gcccgcgaaa aaggaggacg tcatgtgctc gtcacttctc aaagcaaacg tacctatgat 960
gaaaagggcg ttttctacaa cagcatcgga gaatatccga acgcaatgag acagctggga 1020
cgggaaatga acgttccggt gatcgattta aacaaaaaaa gcattgaata ttacaacgag 1080
atcggcgttg aagcgactaa aaacgtattt atgtttctgg aaccgggaga aagcccgaat 1140
tatccggaag gcatccagga cagggtgcat tttcacgagt tcggcgccaa ccaattggca 1200
aggctcgtca caggagaaat ctccgatttg aatatatatc cgctgaaaca ctcgctcaag 1260
aaataa 1266

<210> SEQ ID NO 35
<211> LENGTH: 645
<212> TYPE: DNA
<213> ORGANISM: Bacillus licheniformis
<220> FEATURE:
<223> OTHER INFORMATION: putative rhamnogalacturonan acetylesterase (yesY)

<400> SEQUENCE: 35
atgacaatca gcatctattt ggccggcgat tcgaccgtgc agcattataa ggctgattcg 60
cctcagggag gctggggcga atttctccag tcttatttat ccggaaatgt acaggtgatc 120
aaccgggcaa tcgggggccg gagttcaaaa acgttcgttg aagaaggaag acttgcatct 180
attttggatg tgatcaaaca ggatgattgg ctgttcgttc agatggggca caatgatgcg 240
tcgaaagaca aaccagaacg ctatacagag ccgtatacga cgtataaaca atacttgaaa 300
atgtacgttg acggcgcgcg tcaaaaaggg gcatcgccgc ttctcatcac acctgtcgca 360
aggctccatt acaaagacgg cgtcttttta aacgatttcc cggactactg cattgcgatg 420
aagcaggtcg caagcgaaga aaacgtccgc ttgatcgatt taatggacaa aagccttcag 480
cattttgcgg aaaaaggata cagcgaagta tttaaatatt ttatgatctc ggaaaatgtc 540
aacgactata cacattttac gaaaaaaggg gcccgggaaa tggcgaagct cgtctcggag 600
ggcattcgag agcttgggct gccgtttgtc aaagagacgg tatga 645

<210> SEQ ID NO 36
<211> LENGTH: 1116
<212> TYPE: DNA
<213> ORGANISM: Bacillus licheniformis
<220> FEATURE:
<223> OTHER INFORMATION: hypothetical protein (unknown)

<400> SEQUENCE: 36
atgtacctga ataaaaagag cgatattcct aaattaacag ataaagagta ttattttctt 60
agccaaaaca catatagtac cgataaaatg aaagaagcat tcaaggaaag aacacctata 120
gagagtaaat caaataaggc tttttttgtt gataaaatta aaagggactc tgacactgga 180
cttgatgcgt atgtttttgt tcaagcaaag aaaaaggacg gtaaatgggt taaacctaac 240
gcaccagaaa acgtcgtcgt ggccttcgct ggaacaaatc ctaaagaaca gtttttttcaa 300 gatgttattg atgcagacgg cggtaacgtt gttatgggtc ttgatccgaa aaagaaatcg 360
caatacataa tcgaaaaaga tgcgaaggat acatcaaaaa caataggaaa atacaacgca 420
accccctcac aagacgcgat gcttagcacc ggtaaataca aattaattac gaaaacgtcc 480

-continued

```
caaatcgggc aagctgatga tctggtacgg gaagttaaac aaaagtataa aggcacctcg     540

acggttattt caaccaccgg acactctctt ggcggcgcag aggctgaata cagcgctgtg     600

aacaatgata tatacgcagt cgcattcaac aatccttccg tcgttaaatt gcattctgaa     660

gaaaagcaaa aggagatccg aagcggcaaa tatgactcgt ctgtaaaagc gattgtcaat     720

ccggatgata tgactggttc cggctggtgg aatgagtacg aacgacacgc aggcagaaca     780

atatatacca aagacccctc tacttcgcgt gtggaacgac aaatacgact agatccgaag     840

tatagcggcg gtatatttgg cacagtgttt aatgtcgctg tagactacat tgctaccaca     900

gcaatgggaa tgccggatac acacggcctc aacaaaggca actttacctt cgacgaaaac     960

ggcaacgttc aaaatataga gggcgatgaa ctcgtttatg acaaaaattt aaaagcgatg    1020

cttccaccgg aagttgcatc cggaagtggc gcaattaaag taacgcccga agttgccaag    1080

cagctcgcgc aaaaagtaaa tgcttgcgga cgatga                              1116
```

<210> SEQ ID NO 37
<211> LENGTH: 1017
<212> TYPE: DNA
<213> ORGANISM: Bacillus licheniformis
<220> FEATURE:
<223> OTHER INFORMATION: flagellar motor switch protein (fliG)

<400> SEQUENCE: 37

```
atggcaaaaa tgaaacaaga caggcttaca ggcaaacaaa aagcggccat tctcatgata      60

tccttagggc ttgatgtgtc agcttccgtt tacaagcatt taacagatga agagatcgaa     120

aggctgacgc ttgaaatatc aaatgtcaga gctgtatcac ctgagaaaaa agatgagatt     180

attcaggaat ttcatgaaac ggctattgct caagaatata tttctcaagg cggcattcat     240

tacgccaagc aggtgcttga caaagcgctc ggcgaagaca aagccgccag cattatcaac     300

aggctgacat cgtctcttca agtcagaccg ttcgattttg ccagaaaagc ggatcccgag     360

cagattctga actttatcca gcatgagcac ccgcagacga tcgcattgat tctgtcttat     420

ctcgatcccg tgcaatcggg tcagatattg tcagagctga atcaggatgt gcaggcagag     480

gttgcaagaa ggatcgctgt tatggacagg acgtcgccgg aaatcatcaa tgaagtcgaa     540

cagattctgg agcaaaagct atcgtccaca ttcactcagg actacacgca gaccggcggt     600

atcgaagccg tagtcgaagt gttgaacgga gttgacagag gtacggagaa aacgatcctt     660

gacgcccttg aaattcagga tcctgagctt gccgacgaga ttaaaaagcg gatgttcgtc     720

tttgaagata tcgttacgct tgataaccgc gctattcaaa gggttatccg cgatgtggaa     780

aacgacgatc tgcttctttc tctcaaagtg gccagcgaag aggtcaaaga catcgtcttc     840

agcaacatgt cgcagcgtat ggctgaaaca tttaaagagg aaatggaatt catgggccct     900

gtgcgtctgc gtgacgtaga agaagctcaa tcgagaatcg taagcgtcat ccgaagactt     960

gaagaagcag gtgagatcgt aatcgccaga ggcggaggag atgatatcat tgtctaa      1017
```

<210> SEQ ID NO 38
<211> LENGTH: 861
<212> TYPE: DNA
<213> ORGANISM: Bacillus licheniformis
<220> FEATURE:
<223> OTHER INFORMATION: AB hydrolase superfamily protein (yisY)

<400> SEQUENCE: 38

```
atgttcagcc ctcggagaca ttcacctatt tacatcttgg gagtatctta tggtaaagac      60

atgatcgggg gcgacggcat gggatatttt atcgaggcag aaccaagcgt taatctgtac     120
```

gttgaagaca tcaatcctca aagcggcaaa gccattgtat ttttgcacgg ctggccatta 180
agccatctcc agtttgaata tcaatttgac gatctttcgc gaaagggata ccgctgtatc 240
ggcattgact ggcgtggatt cgggcgttcg gataagccgg cgacgggcta taattacaac 300
cgtttggctg atgatatccg cgctgtcgtt gaggcgcttc aattaaacaa cttcacgctt 360
gccggtcatt caaccggcgg cgccatagca ctccgctata tgtcccgata taggggcgct 420
ggggtctcaa agctggtttt gatcgatgcg gcggcgcctg tgggatttac tgaagaaacg 480
gcagccaaat tgcttcagca agcgtctaac gatcgtccca agatgatgcg cgaagtgacc 540
gacacgtttt tctttcaata tattacacaa ccgttctcag actgtttttt tcaattggga 600
ttgcaggcgg caggctggtc gacaaaagcg gtcatcgaaa tgctgagaga tgagaaactg 660
tatgatgatc cggaaaaagt cgctgctcca gccttaatca ttcacggtat tcaagacaag 720
gtgattccgt ttgcacaagc aaaggagctc agccgcaaaa tcagaaattc atatcttgtt 780
ccgtttcaat acagcggaca cggtccattc tgggaggaac gcaaaatgtt caatcggatt 840
ttaacgcaat ttatcggttg a 861

<210> SEQ ID NO 39
<211> LENGTH: 606
<212> TYPE: DNA
<213> ORGANISM: Bacillus licheniformis
<220> FEATURE:
<223> OTHER INFORMATION: putative hydrolase (mhqD)

<400> SEQUENCE: 39
atgaattata tatatgaaaa aggggactct gatctcaccc tgttgttatt gcatggaaca 60
gggggaaacg aacacgatct tctgccgatc ggcaagatga ttgatcccga tgcaaatttg 120
ctcggggtca ggggaaatgt gctggaaaac ggaatgcccc gtttttcag gcggctgaga 180 gaaggggtgt ttgacgaaaa agatttgatc gaacggacgg atgaattaaa aacgtttcta 240
gatgaagcag ccaaggaact tcactttgac agaagccggg tggtcgcaat cggctattca 300
aacggcgcca atatcgcggg aagtctgctg ttccgtcatg aacatgtact gaaaggggcg 360
attttgcatc atccgatggt tccgtttaga aatcgcaagc tccctgatat gacaggtctg 420
cccgtgttta tcggggccgg caaaacagat ccgctctgtc cgccgcagga atcaagcgag 480
cttgccggct atttcacaaa cgccggcgcc aaagtgctcc ttcactggga aggcggaggc 540
catcagctga cacacggcga aattgaaaag gcgaaaatct ggtatgaaaa gcatataaaa 600
gcataa 606

<210> SEQ ID NO 40
<211> LENGTH: 753
<212> TYPE: DNA
<213> ORGANISM: Bacillus licheniformis
<220> FEATURE:
<223> OTHER INFORMATION: putative esterase (ypmR)

<400> SEQUENCE: 40
ttgaacatac gttttattac agtcatgatg gccctcgtct gtctgctttc agcctgtacg 60
gagtggaatg cgggtgttga aaaaacatcg gtctccccta agcgcgatat cgtgattgca 120
gcggtgggcg attctctgac agagggggta ggcgatcaag aaaagaaagg ctatgtcggc 180
atggtggccg atgagcttga aagccggagc gatgtgaagt ccgtaacggt caaaaattat 240
gccgttaaag gctcccggac tgatcagctg cttgaaagat taaaagacaa agaagtacaa 300
gagggcctga aagatgcaga ctacattttg tttacaatcg ggggcaacga cctgatgaaa 360
gtcgtccgcc aaaacttcgc gcacttaacg ctcacacctt tccgtgctga acaaaaactg 420
tttgaaaagc ggttttcgaa tattttagcg gaaatcagag agcaaaacgc cagcgctgaa 480
ttgatttatg tcagcatgta taatccgttt aagtttacgc tgtctgaact gcgggaagtt 540
gaccaagtcg tagacgaatg gaatgaaggc gcggaaaaaa ggctgaagaa ggtctccaac 600
acgaaaatgg cggatatcgc tgatattttt gaggaataca gcgatgaaaa gaagattgca 660
gaagacgagt ttcatcctaa tcaatacggg tattctttaa tagcgaaacg cgtttacgaa 720
caaattaaaa acgaagacct cccagcagaa taa 753

<210> SEQ ID NO 41
<211> LENGTH: 615
<212> TYPE: DNA
<213> ORGANISM: Bacillus licheniformis
<220> FEATURE:
<223> OTHER INFORMATION: putative lipase (lip)

<400> SEQUENCE: 41
atgcgtcgtc attcattttt atctattcta ttgatttgca tgctgtctgt tgtgtccgta 60
ttttcgttcc ggccttcagc agcttccgcc gcttcccaca atccggtcgt catggtccac 120
ggcatcggcg gagccgatta taacttcatc ggcattaaat cgtatttaca atctcaaggc 180
tggacaagca gtgagcttta cgccatcaac tttatcgata aaacgggaaa taatataaac 240
aatgctccga gattatccga atacatcaag cgtgtgctga atcaaacagg agcatcaaaa 300
gtcgatattg tcgcccacag catgggcggg gccaatacgc tctattatat taaaaatctg 360
gatggtgcgg ataaagtcgg acatgtcgtc acccttgggg gcgctaatcg tctcgttaca 420
aacacggcgc ctcagaatga caaaatctca tacacttcga tttacagcac aagcgactat 480
atcgtcttaa acagcctctc caaacttgat ggtgcaaaca atgtgcaaat ctcaggcgta 540
agccatgtcg gtcttttgtt cagcagcaaa gtaaatgcct tgattaaaga cgggctgacc 600
gccagcggga aataa 615

<210> SEQ ID NO 42
<211> LENGTH: 762
<212> TYPE: DNA
<213> ORGANISM: Bacillus licheniformis
<220> FEATURE:
<223> OTHER INFORMATION: hypothetical protein (yqiL)

<400> SEQUENCE: 42
atgaccataa cggaaagaat atatactgtt gaagggtgca tgttttatac aaagcagaga 60
aaaggaaaaa agaacgcaac gattattttt gaagcgggct acggtttttc ttcaacgact 120
tggcagccca ttttatccga tatagacgaa gatctcggct tgtttgcata cgaccgtgca 180
ggccttggca aaagcgggcc gagcaccagc aaacgaacag cggatcagat ggtgaaagaa 240
ctaaaagcgc tgcttgcagc agcagacgtc aaaccgccct acctgtttgt cgcccattcg 300
ttcggcgccg tcattgcaag gctgtttgca agccggtaca gcgatgaagt catcggcatg 360
gtgctgcttg atcccgcttg tgaagatcag gaggaaaaag tgctgccgct acttccggac 420
acattaaaag aagattatgt caaacagttt tcgatcgaag ggtcccatga ggactttaaa 480
caaagcctgg acatgctgaa gcaggaaaag aaacacctcg gttcggttcc tttgctcgtc 540
ctctcggcgg gaaaaaggac ggaggcggcg aagcaagctc atcaagaatg gctgaagctt 600
cacagcagac tgctgtctct atcgcatcaa agcggctgga ttcaggcgaa aaacagctcg 660
catttgatcc atcatgatga gccgcacatc gtccagcttg cgatctatga tgtgtggtat 720
gcggcacagc agcaaacata cgcctatcaa gccgccaatt aa 762

<210> SEQ ID NO 43
<211> LENGTH: 732
<212> TYPE: DNA
<213> ORGANISM: Bacillus licheniformis
<220> FEATURE:
<223> OTHER INFORMATION: putative lipoprotein (yqeF)

<400> SEQUENCE: 43
atgaaaaaaa gcttggtgat ggttctcgtt tttctgcttc tgctttcagg ctgcggagag 60
gacgatccca gaaaagtcgt agcatttgga gacagcaata cacgcggctc aaattggcaa 120
tttcgcgatt atccaaaagc ggaaaagtgg gtcaatttac ttcagacttc ccttcaaggg 180
cagtacaaaa taaataatgc aggaataggc ggagaaacga cggaagacgc caggtttcgg 240
ttcaggaagg atgtgctgga caagcagccg gcatatcttt ttatcatgtt cggaacaaat 300
gatgcagcaa ttcttacgaa agggctgccg cgcgtatcca aaaaaaggtt taaagaaaac 360
ctttattatt ttgttaaaga aagccgccgc cgcgggatag agccggtttt aatgacgtgc 420
ctgccgatcg tcgaaggaag cggggacaac atcttttatt atgcaagata ccgggcttct 480
tcgtttgaaa aatacggtgg agcgcgtaaa tggcacgatt cctataatga cgtcacaagg 540
gaaacggcgc gggaacttga tgttccgctt atcgacaact ggaaaaacat cgtgaaaaaa 600
gcgggcggag ctacagatga gaagctgatc cattcgaggt ttatcgaccc atcgggaaat 660
cacttaaccc caaaaggcgc gcgaattatt tttgaaggaa ttaacaaaag caaaatcata 720
aaaacgtctt ga 732

<210> SEQ ID NO 44
<211> LENGTH: 828
<212> TYPE: DNA
<213> ORGANISM: Bacillus licheniformis
<220> FEATURE:
<223> OTHER INFORMATION: putative lipolytic enzyme (unknown)

<400> SEQUENCE: 44
ttgagaggat tcatcaaatg ggcaggattg gcgattctgt gtattggctt gtttgcgtgt 60
acttctaaca ggaatgccga aaatgttcat tatgcaaaag acgacagaca aacattggat 120
atttatacac cgcagtcaaa cgagggcgaa aaacatcccg ttctcatcta ccttcacggc 180
ggaggatgga caagcggcga caaaagcagg gctgcttcga agccggcatt ttttacggat 240
aacggctatg tttttgtatc tgtcaactat cggcttcatc ccgatgttca gtatgatgaa 300
atggctgatg atgcggccaa ggccgtaaaa tgggtgatgg atcatgcgga cgagtatcaa 360
atcgatccgt caaaaatcaa cgtcatggga cattcggcag gggacactt ggccggatta 420 attgccgcag attcaacata tttaaatcgt gtcggcctca cgccggccgc actcaattcg 480
attgttgttt tagatggccc cttggatatg aaacgattca tcgaagcgat cccgtcttat 540
aaagaagtgt ttggcacaga cgaaaaggtg tggacaaaag catcgccgct ctcatacata 600
aacaactcaa aattgccgcc ggcctatctt gtgacccgct gggaagaccc tgccgtttac 660
aagttcgcgg aaaccgcaaa caaagcgaag gcaacggaat ttgtgtatca agtcaacagc 720
ttatctcaca gtgatttaaa caagatgttc ggctctccag atgcaccggc agaagcgcag 780
aatctgacaa aagcggttat ggcgttttta gagaaggaaa ataaatag 828

<210> SEQ ID NO 45
<211> LENGTH: 888
<212> TYPE: DNA
<213> ORGANISM: Bacillus licheniformis
<220> FEATURE:
<223> OTHER INFORMATION: putative hydrolase (ytaP)

<400> SEQUENCE: 45
atgcgcagtc aacttttcaa actgctcggc gatttgccgg ggaaaaaaag cattgatgcg 60
agcactctta aaatcgaaga aaagtcatct tttattctcg aaacgctttt gcttgattta 120
aacggaattg aagcggtgcc ggcctatttt gcaaaaccga aacagatgaa cggcaagcgg 180
ccggccgtgc tttactgtca ttcacacgga gggcgctacg aaaggggaaa ggaggagctg 240
gttgaaggag cggagtactt gcaagcgccg ccgttcgccg aggaattgac ggctttggga 300
ttctccgtgc ttgcgattga tcattgggct ttcggagaca ggcggggcaa aacggagagt 360
gagatattta aagaaatgct ttggacaggg cgggtgatgt ggggaatgat ggttttcgac 420
agcatcagag ccatcgatta tctgaaaatg agggaggaca tagacgaaag ccgcatcgct 480
tcactcggca tgtcgatggg aggtctgatg gcctggtgga ccgctgcatt ggatgagcgg 540
gtcagcgtat gcgttgatat atgcgctcag gtggacagcg aaacattaat caagacgcag 600
aatttggacc gccacaatct ctattcttat gttccagggc tggtcaaaca cttttcaacc 660
gctcaaatcg aaagcttgat cgctccaagg cctcatttaa gcctggtcgg aaccgcagat 720
aaactgacgc cggttcaagg gattgacatt attgaagaaa agctgtccga tgtgtatata 780
gaaaaaggcg caggtgaacg ctatgaagtg tttcgttctc attcagggca cctcgagaca 840
gccggaatga ggcataaagc ggtcggtttc ttaaaaacat ggctgtaa 888

<210> SEQ ID NO 46
<211> LENGTH: 780
<212> TYPE: DNA
<213> ORGANISM: Bacillus licheniformis
<220> FEATURE:
<223> OTHER INFORMATION: phospholipase (ytpA)

<400> SEQUENCE: 46
atgtggtgca tggaagcgga aagacctgtt gctacaatcg tcgtcattca cggtgcatgt 60
gagcatcacg ggcggtataa atggctgtcc gaaatgtggc gttcatccgg ctttaatgtc 120
gtgatggggg atttgcccgg ccagggcact tcgacaagag aaagaggaca tatacgctct 180
tttcaagaat atattgatga agtggacaaa tgggtcgcca gggcgaaagc atttgaactg 240
cctgtgttta tgctcgggca cagcatgggc ggcctgattg cgatcgaatg gtttaagcag 300
cagcaaagcg gcattgccgg tctcatttta tcatcccctt gtctcgggct gcaattaaag 360
ccgaacaaat ttctggactt gatttccaag ggctcaacg ttttggcgcc gtctatgcgg 420
tttgaatccg ggatcacgcc tgataaagcg acgagaaaca aagaagtcat cgaaatggac 480
atcaacgatt cattatatat cacaaaagtt tctgtcagat ggtatcaaga aatgttaaaa 540
gcgttgaaaa gcgcgatgga gccgacggac gcctttctca acatcccgct ctttgtcatg 600
caggcgggca ccgactggct tgtcgacaaa aaaatggtcg tcaagtggtt taaccagctt 660
gcttcccaca ataagacgta cagggaatgg gatggcttgt accacgaaat tttcaatgag 720
cctgaacggg aagacgtttt taaagcggcc agagcgtttg cggagcagta tataacataa 780

<210> SEQ ID NO 47
<211> LENGTH: 801

<212> TYPE: DNA
<213> ORGANISM: Bacillus licheniformis
<220> FEATURE:
<223> OTHER INFORMATION: putative dipeptidylpeptidase (ytmA)

<400> SEQUENCE: 47

```
atgtggatag aaaaaagaag gtttccatcg ccgaacaaag aggtgcgtct gttttccgtc     60
acatacottt cacaaggact caaggttaag ggcttttgg ccgaaccggc cgctcccgga    120
aattatgacg ggtttttgta tttgcgcggc ggaattaaaa acgtcgggat ggtcagaccg    180
ggccgaatcg tccagttcgc ttcacagggc tttgtcgttc ttgctccgtt ttacaggggc    240
aatcaaggag gagaaggcga tgaggatttt gcaggtaatg accgggaaga tgcttttgcc    300
gcttttcgtc ttcttcagaa gcacgaactg gtaaaggacg gacgcgttca catttttggc    360
ttttcccgcg gcggaatcat gggcatctta acggcaatcg aaatgaaagc agcggccgct    420
tcgtttgtgt cttggggcgg tgtcagcgac atggtcatga cctatcgcga acgaaaagat    480
ttgcggcgga tgatgaagcg ggtcatcggc gggacgcctg aaaaggttcc cgaagcgtat    540
gaatggagga cgccttttga cgagctggag aagattgaag cgcccgtgct tttgatccac    600
ggagcaaacg atgaaaatgt ctccatcgag catgcgcggc gtcttgagcg tgaacttctg    660
cgaaggaaca agtctgtgga tacgtggtat ttcagccaat atacccacta ttttcctccg    720
cgcgaaaaca ggcggattgt tagagaatta tcccaatgga tgaaaagccg tccttggaca    780
agttatggta aactaaagta a                                             801
```

<210> SEQ ID NO 48
<211> LENGTH: 822
<212> TYPE: DNA
<213> ORGANISM: Bacillus licheniformis
<220> FEATURE:
<223> OTHER INFORMATION: 2-succinyl-6-hydroxy-2, 4-cyclohexadiene-1-
      carboxylate synthase (ytxM)

<400> SEQUENCE: 48

```
gtggccgttt tgaaattgac actgaaagac ggcgtttcct ataaaattga agacaatggc     60
ctgtctgcag aaaaaacggc ggtgtttttg catggcttta caggaagcgc ggccacatgg    120
gacgggatag acggctattt tcaggggatg cgtctgatca agctgaatct gctcggacac    180
ggcggaaccg actcgccatc ggacagccgg cgctacacaa cagagaagca ggcagcggat    240
ctcatcgaaa tttttgatcg tttaaatgta aaacaggctt acctcatcgg ttattcaatg    300
ggcggccggc ttgccttatc cttggcgatg attcaccccg agcgtgtgtc cggtcttgtg    360
ctggagagca gttctccggg gcttgattcg cctgaagaaa gaaaagcgcg cagggagcag    420
gacagccggc tcagcaggcg gatacttgaa gaaggaatca agtctttcgt agattattgg    480
gaaggcattc cgctgtttgc atcccagctt tcaatggacc cttcaaaaag aaaaaaagtg    540
cgcgaagaac gtctgaacaa caatccgatc ggccttcgag gcagcttaat cggaatgggg    600
accggatcac agccgtcttg gtggaacaaa ctgagcggga tcaattatcc ggtgcttctc    660
atcgcgggaa gcctggatca gaaatttgtc gccatcaatg aaagcatggc aaagcggatt    720
ccagccgccc gcctcgagat tgttgaacat accggtcatg cggttcatgt ggaagagccc    780
gatttttttg gtagaatagt aagtgagttt attttaaagt ag                      822
```

<210> SEQ ID NO 49
<211> LENGTH: 822
<212> TYPE: DNA
<213> ORGANISM: Bacillus licheniformis
<220> FEATURE:
<223> OTHER INFORMATION: alpha/beta hydrolase (yugF)

<400> SEQUENCE: 49

```
atgctgttaa caaaaccttc tatcgagacc attcaagggg tcaatatata ttatgaacat     60
tacgagaatc caggcaagac atcgctcgtt ttaatacacg gttttctttc ttcctcgttt    120
tgctacagaa aaatcattcc tcttctgaag gatgagttta atttagtcgc cgttgacctg    180
cctcccttcg gccaatcaga aaaatccagc acctttgtgt atacctatca aaacatggcc    240
agggtggtca tcgaactgat cgaaaggctg aagattaaag acgccgtgct tgtcggtcat    300
tcgatgggcg gccagatttc actttatgcg ataaaggaaa ggcctgaact gttcaaaaaa    360
gtcgtcctgc tgtgcagctc aggctattta aagcgttcgc cccgctcgct tattttcggg    420
agccatattc cttattttta tttgtacatc aagcgctggc tgtcaaaaca gggcgtcctg    480
aaaaacctca tgaatgttgt ctacgacagc tccctgatcg atcaggaaat gatcaacggc    540
tacctgaaac cgtttctcga tgatcaaatt ttcagggcgc tcgcacgtct tatcagacac    600
cgggaaggcg atttatcacc ggatgatttg aagaaaatcg agacgccttc cctcttgatc    660
tggggcgaag aggaccgcgt cgtcccggta cagatcggaa aaaggcttca tcaggatctg    720
cccaattcca ttttctactc cctgcaagaa accggacacc tcgtccctga agaaaatccg    780
gattatgtat cagacaagat tgccaatttc attttgacat ga                       822
```

<210> SEQ ID NO 50
<211> LENGTH: 897
<212> TYPE: DNA
<213> ORGANISM: Bacillus licheniformis
<220> FEATURE:
<223> OTHER INFORMATION: dipeptidylpeptidase (unknown)

<400> SEQUENCE: 50

```
atgacgaatc atataaaaga aatcaactgg gagcaaaaca ccaactctta cattcagctc     60
ataccgaata ttgagtacac aaaagtggaa gacacttctt tgacattaca tttgctggtg    120
taccgcaatc caatggatgc gttatttaac aggaaaggca atcaggaaac atacccgctg    180
atcatttatt tgcaagggtg cggatggggc tggacaaaac aggatacatc cgcctttatc    240
ccccaactgg ttccatttgt cgagcaagga tatgtcgtgg caagcgttca atacagaggc    300
agcggagagg cggtgtttcc ggctcagctt catgatgtga aaacagcagt ccgcttttta    360
aaagcaaatg ccgcccgcta taacatcgat cctgatagag tcggagtctg gggggattct    420
tcaggcggcc atttggctct tttgcttgga ttgaccgaag gaattgaaga atttgaaggc    480
ccggacgaat accgtcatgt atcgagcaaa gtcgatgcgg ttgcggactg gttcggtccg    540
gtcgaccttc tgtccatgag caagtatccg tccatcttcg atcatgattc acccaattca    600
ccggaatcca agctgatcgg cggagctgtt caagaaaaca gagtacaggc gaaacaagcg    660
agtccgataa gctatgttca cagggaagcg cctcccattc tgattatgca cggggatcag    720
gacgatgtcg tcccttatca acaaagcgtc caattgtttg aagccttaat aaaagaaggc    780
catgatgccc ttatgtataa aataaacggg gccggacata acggttttac ccaggctcat    840
accctggaca tcgtcaaatc gttcttccgc aaacatttaa agcctggaaa agcctga       897
```

<210> SEQ ID NO 51
<211> LENGTH: 1962
<212> TYPE: DNA
<213> ORGANISM: Bacillus licheniformis
<220> FEATURE:

<223> OTHER INFORMATION: putative acylaminoacyl-peptidase (yuxL)

<400> SEQUENCE: 51
atgaagcagc tgataaccga aaaagacctc atcaagcttg tatccattac cgatccccag 60
tattcgcccg atggtgcaaa aatcgcctac gtccaaacaa aagtaaacga aaaacaggac 120
tcatatgatt cgcatatcat gatctacgac cgcgaaaaac aagcttcggt gcaatggacg 180
tttgggaaag gcagaaacca gcatccccgc tggtcgccgg acggcaaata ccttgcattt 240
acgtccaatc gcgaggaaac cgcacaaatt tacgtgataa gcgccgccgg gggagaagcg 300
agaaaagtga ccgatattcc ctatgatgta tcacagcctg aatggtcgcc ggacggcaag 360
tcattgcttt gttcagtgaa gctgacaaaa gaggaaagcg tcgacgatga gaagaaaacc 420
gagattgaag accacgaacc gctggaagtc gattctttgt catataaagc agacggccaa 480
gggtttaaaa ggggaaagta tacgcagctt gtcctcgttc aagtggaaac cggggaaatg 540
aaacagctga ccgatcttga acgcgaccat ttcagccatg cattttcacc gtgcggagat 600
cagattgcat tttgcgccaa tcaaacggat atgcgtgtga acgatgtcta cttgatgaac 660
ctttcgacag gtgatttgaa gcgcctcaca ggtcaaaacg gcattttttc ttcactatcg 720
ttttctcctg acggcaaaca ccttgcattt atcggaaacg agaaagaata tcaaaacgcc 780
acgctcgata aagcatggct gtatgatatt gaaacaggaa aactaacgtg tctgacggaa 840
atgcttgacg tccatctcag cgatgcggtg gcaggagaca gccttgtcgg aggcgttctt 900
ccgaaaccgg cctggaccaa agacggaaac ggcttttatg tcatcggatc tgaccagggt 960
tctacaggca tttactacat atcaatcgaa ggtcttgctt atccggtccg gttggaaaaa 1020
gagcatgtga acggattcag cctgcatccg gacgaaagtg gctttgcggc atccatagcc 1080
ctgcccgtcc ggccgagcga actttaccat ctccaattgg gtgaagaaaa agcggagcga 1140
ctaacagatg ccaaccaagc gtttacggaa gaacatatca tatcggaacc ggaggagctt 1200
caatttcagg cagcggacgg tctgacaatt cacggatggc tgataaagcc cgcccaatat 1260
gaaaaaggaa acacgtatcc gctcattctg gaagtgcacg gcggacctca cgccatgtat 1320
gcgaatgctt attttcatga atttcaagtg ctggccgcaa agggaagcgc cgtcgtatat 1380
gttaacccgc ggggaagcca cggctacgga caggattttg tcaaccgggt gaggggcgac 1440
tacggcggtg gagattttaa ggatgtaatg gcggctgttg accacgtgct tgaacattat 1500
gatttcgtcg atcaagaaag gctcggcatc accggaggaa gctacggggg ctttatgaca 1560
aactgggctg tcggccacac gaagcgcttc aaggccgcag tgacacagag gtccatttcc 1620
aactggatca gtttttacgg ggtaagcgac atcggctatt ttttcacaga ctggcagctc 1680
ggtgcagacc tttttgaaga tccaggcaaa ctgtgggagc attcgccgct caaatacgcg 1740
gacaaggtgg agacccctct tctcattctg catggcgaac gggacgacag gtgcccgatt 1800
gaacaggcgg aacagctgtt cacggcgctg aaaaaaatgg ggaaagaagt aaaactcgtc 1860
agatttccga acgcgtcaca cgatttatca agaagcgggc atccgaagca gcggatcagg 1920
cggcttgagt atattgcagg ctggtttgaa gcttatctat aa 1962

<210> SEQ ID NO 52
<211> LENGTH: 1440
<212> TYPE: DNA
<213> ORGANISM: Bacillus licheniformis
<220> FEATURE:
<223> OTHER INFORMATION: phage putative hydrolase protein (unknown)

<400> SEQUENCE: 52

```
ttgagtaaga agattaagaa gtccaatctt acggatgaga cttattatcg tataagccaa     60
cgttcttaca actacgatta tctcagaaaa aaattaaaaa acaaagagta catacggata    120
aattcatctg tttccggagc cacctactgg tatgttgata aaattaaaac agacgaagac    180
accgggttag atgcggccgt tctatcccag gccgaaaata aaaacggcaa gtgggtgaaa    240
tccgaccacc ccaaaaacgt cgttgtagct tttgcgggaa ctgatccggg gaaggacccg    300
ttaagtgacg tagagcaagc agacattaat catatcgtct taggaaacga tccgaaagat    360
aaaacacaat atgtcgtcaa gaaagatgcg aaagatatgt ctaagacgtt cggtagatat    420
attggttcga tggaacaaac tgccatgctt gagtccggag attataaatt aattacaaaa    480
acatcgcaaa tcgatcaagc cgatcaactt gtgcgggaag ttaaacaaaa gtataaaggc    540
acctcgacag ttatttcaac caccggacac tcgctcggcg gcgcagaggc tgaatacagc    600
gcggtcaaca atgatatcta tgccgtcgcg tttaatagcc cctcaatcgt tcacctgcat    660
tctgatgaaa aacagaaaga aattaataac ggagattata actcttatgt aaaatctatc    720
attaatccgg atgatatggt cggtgccggt tggtgggacg aattcgatcg ccacaatggg    780
actaccatct acacaaaaga cccttctatt gcaacggcta atcgcgaaga aagacttgac    840
ggcaataaac tccaacaggt tggaagaaac cttctgtatt tcgctaatac actaatcttt    900
caaaatccgg atacacatgg gataaataag tcgaatttct ctttcgacga aaacggcaac    960
gttcaaaata tagagggcga tgaactcgtt tatgacaaaa atttaaaagc gatgctccca   1020
ccggaagttg cctccggaag tggcgcaatt aaagtaacac ccgaagttgc caagcagctc   1080
gcgcaaaaag taaatgcgat catcgatgac ttgcggacga tgaaacggga agccgaaaac   1140
gcttatcagg aacacgacgc cgagatcaac gacctgaagc acgataccta ccgtcaggtc   1200
ggccacggtt tatacgacaa gctgacactc gaggatgtaa acaatacgct gaaaaacctg   1260
gcgcagtcgt ttgacaaaaa aggcaatccg ctattttacg atgttcatgc cgaaaaagcg   1320
tacatcgcct cattaaaaaa tacgatttca gatttagaag acatcagcgg gtacctggcg   1380
cagattgcaa aagattttaa atcgaaagat aaaatgctgg caaattggct taaactttag   1440
```

<210> SEQ ID NO 53
<211> LENGTH: 849
<212> TYPE: DNA
<213> ORGANISM: Bacillus licheniformis
<220> FEATURE:
<223> OTHER INFORMATION: trilactone hydrolase (besA)

<400> SEQUENCE: 53

```
atggctcaag aaaaacttca gcagtctgtc aatgctgctg aatgcatccc ggttgcgata     60
ccggggacag aacagcggtg catgcgttca ctggatggga gccgcacata tcggattttt    120
attgcgaaac catttgggga acagccgccc gcaggatatc ccgtgattta tctgcttgat    180
gccaattccg tgtttggaac gatggtggag gcgttgcgga tgcagtcgcg ccgtcccgat    240
aaaaccggtg tagggacggc tgttattgtc ggcatcggtt acgagaccga cgctcccttt    300
gaccgggggc ggtattatga ttttactctg ccggaatcgg gcgctgagct gcccatgagg    360
cccgatggag cagactggcc ggaaccaggc ggggcgaaag cttttctgtc cttcatcgaa    420
cagcagttaa agccggagat cgaacaggaa ttcacgattg atgtgaaaag gcaggcgatt    480
ttcggtcatt ccctaggcgg actttttgtc ctgcagaccc tgtttacaaa accggatcta    540
tttcagacat atatcgccgg cagtccgtcc atccattggc atccgtcatt ttttgataaa    600
```

-continued gagcatgact ttgtttcgaa gttgcaggaa gctgatggcg atgtaaaggt attgcttggg 660
gccggagaac tcgaaaagac gcataaaagc gggatgaacg acaatgcaaa aaggctggcc 720
gaccgcttgg ccgctttgga aagtcagggg gttcgcgcgg agtaccatga atttaaaggg 780
gaaggtcata tatcggttct gcctgtgtta atcagcagag cgctgcggtt tgccttcaag 840
cctgattga 849

<210> SEQ ID NO 54
<211> LENGTH: 663
<212> TYPE: DNA
<213> ORGANISM: Bacillus licheniformis
<220> FEATURE:
<223> OTHER INFORMATION: rhamnogalacturonan acetylesterase (unknown)

<400> SEQUENCE: 54
atgatgcgag acattcagtt gtttttggcc ggggactcaa cggtttgcga ttatgatgag 60
aatagggcgc cgcgtgcagg ctgggggcag aaaatcggcg agtttttaag cgcaggtgtt 120
ttgatccgca atgaagcggc atcaggaaga agctcaaaaa gctttattga agaaggcagg 180
ctgaagcgaa tcataacaca gatcaaaagc ggcgattatt tgtttgtcca gttcggtcat 240
aacgaccaaa aaccggatga tcgctataca gagccataca caacttacaa gcagcatttg 300
acccggtata tagatgaggc acggttaaag aaagccaatc ctgttctgat tacaccggtc 360
cagagaagat catttgcaag cgatggccgc tttaaaaata cccatggcga ctatcctgat 420
gcgatgatac agcttgcgga agagcttcgg gtgccgctta tcgatctcgc cttcaaaagc 480
cgtcaattgc ttgaatcgct aggaccggaa gcttccaaaa agctgtattt atggcttgaa 540
ccgggggaac accccaacta tccggacgga gccagggatg acacccactt ttgcgacttc 600
ggggcaaaag aaatcgctaa gcttgttgca caggaagcaa aagaagcggg aattccttta 660
taa 663

<210> SEQ ID NO 55
<211> LENGTH: 741
<212> TYPE: DNA
<213> ORGANISM: Bacillus licheniformis
<220> FEATURE:
<223> OTHER INFORMATION: lichenysin synthase (lchAD)

<400> SEQUENCE: 55
atgaacgaga tcattaagca gtttggagcg ccggcaagcg gtatgcagtt gatctgtttc 60
ccgtttgccg gggggatattc ggcatcattc agaccgcttc acgaacattt aaaaacagat 120
tttgatatgc tggcgatcga accgcctgga cacggcacaa atcgaatggc gcttgtcgac 180
aatttggaaa agctcgccga tttgtatata gcggcgctta agccgcggct ttcctctcaa 240
ttcgtgctgt tcggccacag tatgggcggc atggttgttt acaggctggc gcaaaagctt 300
gaacaagaag ggatctttcc ggcagccgct gtgatatcag cgatacagcc gccccatatt 360
cagcggcaaa aggtgtctca ccaaaaggat gacgcatttc tcgaccatct cattcagctt 420
ggcggaatac ccaaagaact ggcagagcac agggaaatga tgaacttttt cctgccttcg 480
ttcagagcgg actacagagc gcttgagacg ttctgccata ccgatcatac gccgcttaga 540
tcgcctgtgc atattctgaa cggagaccgc gatgagaaat gcatgaggga tgcgcttggc 600
tggaaaaagt gggcgaatac gatcgatttc cactatttca aaggcggaca tatgtatctt 660
ttatcagaaa cggaacaagt agccgccaag ttgaaaacga ttgccgcggc cagccgcagt 720
acggctgttc cgacaatgta a 741

<210> SEQ ID NO 56
<211> LENGTH: 816
<212> TYPE: DNA
<213> ORGANISM: Bacillus licheniformis
<220> FEATURE:
<223> OTHER INFORMATION: putative esterase (unknown)

<400> SEQUENCE: 56
atgatacttg tgcagaatgg agtaatgaac atgatagacg gaacattgat aaaagataca 60
tgcttcggga gggagctttt gatctatctt cctccttcat acgggagcgg tgaaaaccgc 120
tatcccgttc tatacgtcca tgacctggga gatttattcg atccggcata cagcaacagt 180
ctgcgctcaa tcgaaaagct gttttcgagt caggaagtgc cggaattgct gctggtcgga 240
gtggctccaa aagacaggga aagcgaatac acgccttttc ccaagcggca tttgctgccg 300
aataaacggg agtacggcgg gaagggcaac gaatatgccg ctttttggc caatcggctc 360 aagcctcata tcgaccggca ctaccgaaca aatccgagcc gtgaacaaac aggaatcatc 420
ggaaagtcgt tcggagggtt gatctcggtt tacacagctt ttctagcatc ggagaccttt 480
ggaaaaatcg gatctttgtc aggttctttc tggtttgaag gaataaccga gtttatgaag 540
aataaccgct ttgagaataa gcatctgcgc atttatatgg atgtcggaag cacggaaggg 600
acagacaggg ataatctgca gaaagagatg ataccgagga caaaggaagc cttcagcctg 660
ttaacagaaa gcgccgcctc cgaaaaagaa ctgaaatttg tcattgatga aggtggctca 720
catcggcttg agcggtttgc gaagcgtttt ccggaagccg ttaaatggct gtttggctcc 780
tgtcacaaca gcgcacggaa tggcaggagt ttctga 816

<210> SEQ ID NO 57
<211> LENGTH: 639
<212> TYPE: DNA
<213> ORGANISM: Bacillus licheniformis
<220> FEATURE:
<223> OTHER INFORMATION: spore germination lipase LipC (lipC)

<400> SEQUENCE: 57
atgacgcttc aatatacggc tctcggcgac tctttaaccg tcggggtcgg tgcaggtttg 60
tttgagccgg gatttgtaca gcgctataaa aggaaaatgg aagaggattt gaacgaagaa 120
gtttctttga ttgtatttgc gaaatccggt cttgagacgt cggaaatttt agcgatgctg 180
aacgagcctt tcatcatgga acaggtcaaa aaagcggacg tcatcacgat aacgggctgc 240
ggaaatgatc ttctgcaatc gctggagata tatgaaaaag aaaaggatga acacgtcttt 300
ttggaagctt cctcccactg tcagaaaaac tactcaggca tgcttgagaa gatcagagaa 360
ataaagggag aaaaagatac gcgttatctc gtccggcttc tcaatttata caacccattt 420
ccgtcaatcg aattagcgga caaatggatt tccggcttta acaggcactt aaagcagcta 480
gagtccgctc cgcaaatcaa ggtgatcgat acttatgctg tctttaaagg acgcgaaaaa 540
gaatatttgt caattgaccg tgtgcatcca agcagcagag ggtatgaagc gatgtcggaa 600
aagctgagag cggcgggcta cgggcggctg gagggctga 639

<210> SEQ ID NO 58
<211> LENGTH: 711
<212> TYPE: DNA
<213> ORGANISM: Bacillus licheniformis
<220> FEATURE:
<223> OTHER INFORMATION: putative esterase/lipase (unknown)

-continued

<400> SEQUENCE: 58

```
atgataggat gtttatgcat tcacggattt accggagcgc cgtatgaatt ggaaccgctg      60
gcttctcatt taaaacaaac ggcagattgg caagttgaaa tgatcacgct ccccgggcac     120
ggtgagatgc cggttttaaa aggcgtctgt tttcaggaat ggatcgcttg tgctgaagtg     180
gagctcatcc gcttgttgaa aacgtgtgat acggtatttt taatcggatt ttcaatgggc     240
gggatgattg ccggctattt agccggaaaa tatccggtca gccgccttgt cctgttgagt     300
gcggccgccc agtacatcag cccgggacag ctgatccagg atttgaagaa tgtgatcaaa     360
gattcactgc aaggcaagct agaggataat ctgctttaca aaaggtacaa acaaaagctg     420
acaagcactc cggtgtcttc tgcatttcag tttcgcaagc tcgtcaagat gacaaagcct     480
gcattgaaaa acctccggat ccctgtgctc attgttcagg gggagtgtga tgccatcgtg     540
ccggtgtcaa gcgcgtatta cttgtatgaa accattcctt ccgaagaaaa agagctgtgc     600
ctcttgccgg aatccaagca ccatgtctgc cttgaagaaa actcctctat cctatttcaa     660
accgttgagg cgttcctcaa aaaaacgccg attgaatcta taaaaaaata a              711
```

<210> SEQ ID NO 59
<211> LENGTH: 1881
<212> TYPE: DNA
<213> ORGANISM: Bacillus licheniformis
<220> FEATURE:
<223> OTHER INFORMATION: putative peptidoglycan O-acetyltransferase (yrhL)

<400> SEQUENCE: 59

```
atgcgagatc agacacaaca acaccgttac ataccggggt tagacggcct tcgggctttt      60
gccgttttgg cggttatcgc ttaccacctc aacatgagct gggccgacgg aggcttcatt     120
ggggttgata tctttttgt tttatcagga tatttgatta catcgattat cctgccggcg     180
tatggaaatg acatttccct cacattccgc gatttttggg tgcgccggat acggcggctg     240
cttccagcgg cgacgctcat gattttcgca accgtcatat gggtcgcttt gtttaacaga     300
gagctgatgc ataccgtacg gggagatgcg atctcctctc ttttgtatgt cagcaattgg     360
tggtttatct ttcacgacct gtcatatttt gatagtttcg gatcgccgtc tcctttaaaa     420
aacttgtggt cactggcgat tgaagaacag ttttatttta tctggccgat cattttgctg     480
ttgggcatct acatatttaa aaagcgggag aggtttgcag cggcggttgt gctgtgtgcg     540
ctttgttcag ccatatggat gagcatcctg tacgtcccgg gcggcgatcc gagccgtgta     600
tattacggga cggatacacg cgctttcgag ctgttgatcg gatgcgcatt agcccttgtg     660
tggccgatga aaaggctgtc tgggaacagg ctccccaaca gcctcaagca tgcattgcac     720
ggaactgagc ttgccgcttt cgcgctgctt atgatgtgca tttattttgt cgatgaattc     780
agcccgtttc tctatcacgg cggaatgctt ataatcagca taatcgcagc tattttgatt     840
gcatgcgtca gtcatccgag cagcttcctg ggctttgccc tttccgtgaa gccgctgcgc     900
tggatcggga aaaggtcgta cggcatttat ctttggcact atcccgttat cgtgctgagc     960
acgcctgttc aggagattgg aaatccggtg tactggcatg ttgcgatgaa ggtcgccgtt    1020
acatttattc tggcggaact ttcgtatcgc tttattgaga agccgatccg aaaagacggt    1080
tttaaaccgt ttgtcagccg ggtttttctg gataagatca cggaatggaa aacggcttcc    1140
gttccaagca aaatatcaat cggcctgatg tttgccgcgc tcctcgtttt tgcagggggt    1200
ctgtcgggat tggccgacga aaagaaacag ccgcagcagg cctattcaaa atcttatgag    1260
```

-continued

```
gaaacaagcg cctcagcgga tcagccggct gacaaaagtg aagaacggca ggacgataag   1320

aaagcacaaa ctgagagcgg aaatgagagt aaaaccggaa acggggagga atcgtcagat   1380

acgaaagatg agcagtctgc ggaaaaagag ccggatcgca tcgaaaaaga agtattggct   1440

gtcggggatt cggtcatgct ggacatcgct tcaagcctgc gccggaagat tccgggaatc   1500

acaatcgacg gacaggttgg aaggcaagtg agggaagcgc ttcaattgac atcaacctac   1560

gcctccttta atcatccgga caaagccgtc gtcattgaat tgggaacaaa cggctatttt   1620

acggacggcc aattggacgc tttgcttgat gctttctcaa aagcggatgt ctatctcgtg   1680

aatacgcgcg tcccccgaca atgggagagc aaggtgaatg aatcgcttcg gaagcatgcg   1740

gacagccgtc aaaatgtgac attggtcgat tggcacgctg aagcactgca acatcccgaa   1800

tatttcaccg ccgacggcgt ccacctgatg ccgaaaggtg ctgaagcctt ggcatcgctt   1860

atcgtcaaag cgatgaaata a                                               1881
```

<210> SEQ ID NO 60
<211> LENGTH: 912
<212> TYPE: DNA
<213> ORGANISM: Bacillus licheniformis
<220> FEATURE:
<223> OTHER INFORMATION: hypothetical protein (unknown)

<400> SEQUENCE: 60

```
gtgtggatcg gaattctgtt gatggtctct gggattggga tcagtatttt cgccgtcagt     60

ctgattgtca gctatttgtt tgttttgccg aaccggagca catatgaaga aactttttc     120

agcggactca aacacggcga gatcatcgat gacgtgtttg agtcccacga caaagaagag    180

ctgtttttga cagcagggga tggatgccgg ctgcatgcgc tgctatttcc cgttcaaaag    240

agcaggaaag ccgtcatcat ctcccacggc atcaagtggt cgctgtttgg cgggtataaa    300

tacgtcgagc tgtttcagtc catcggctac aatgtcctgc tttgcgacag caggtgccac    360

gggttgagcg gcggttcaca cgtttcctac gggttttacg aaaaggatga tttggcgagg    420

tgggctgacg agcttgagaa caggttcggc aaagatcttt ggatcggggt gcttggcgaa    480

tcgctcggag cggcggctgc catcgagctg atgaaacagg atcggagaat caagttttgt    540

attgccgatt cctgcttcag cgatttaaca gagctatgcc gctttcagct gaaagccgcc    600

gtcaaattgt ccgtgccgtt tctcatcccg ttggcaagcg ggctgatcaa gcggcgccac    660

ggctggagcc ttgctgatat atcgccggtc agcaaccttg agcagtcaga cacgccgctg    720

ttgatcatcc acggcacaaa ggatcagctt gttccgccgg aaatggccaa aagcctgtat    780

gagaggaaaa agggattcaa gaaactgtac tggattgaag gcgccggaca tgtcggcgga    840

tttcgccaca atcctgagga atacttaaat aaaatcaaag actttatctt gaaaatcgag    900

ccggccaatt ag                                                         912
```

<210> SEQ ID NO 61
<211> LENGTH: 32
<212> TYPE: DNA
<213> ORGANISM: Artificial Sequence
<220> FEATURE:
<223> OTHER INFORMATION: Oligonucleotide: PCR-amplification of pE194

<400> SEQUENCE: 61

```
tatatacagc tggattcaca aaaaataggc ac                                   32
```

<210> SEQ ID NO 62
<211> LENGTH: 33

<212> TYPE: DNA
<213> ORGANISM: Artificial Sequence
<220> FEATURE:
<223> OTHER INFORMATION: Oligonucleotide: PCR-amplification of pE194

<400> SEQUENCE: 62
tatatacagc tggattatgt cttttgcgca gtc 33

<210> SEQ ID NO 63
<211> LENGTH: 30
<212> TYPE: DNA
<213> ORGANISM: Artificial Sequence
<220> FEATURE:
<223> OTHER INFORMATION: Oligonucleotide: PCR-amplification of functional mRFP cassette

<400> SEQUENCE: 63
tatatggatc cgtaatcagg gtatcgaggc 30

<210> SEQ ID NO 64
<211> LENGTH: 31
<212> TYPE: DNA
<213> ORGANISM: Artificial Sequence
<220> FEATURE:
<223> OTHER INFORMATION: Oligonucleotide: PCR-amplification of functional mRFP cassette

<400> SEQUENCE: 64
tatatggatc cctcattagg cgggctacta a 31

<210> SEQ ID NO 65
<211> LENGTH: 1027
<212> TYPE: DNA
<213> ORGANISM: Artificial Sequence
<220> FEATURE:
<223> OTHER INFORMATION: Fusion of 5- and 3-prime regions of aprE gene with flanking BsaI sites (homology regions)

<400> SEQUENCE: 65
ggtctcgacc cgaagttctt ttttaacata taggtaaaac aatacgaaaa aaggcgccaa 60
gtattgaaga attgcagcag ccgcggcatt tcccttttcg attgaagcaa aaaacgtata 120
ttgaacagta agcattccaa aaatggaaaa tactaaaatc gaacaaatat ctgttttttt 180
cttccatatc tgacacacat gttgaaaacc gtttttcatt gaaacatata acaagagaat 240
gactcccgat gccagaagcc tgacagagac aagcgagccg gcttcaaccg ctcccctttc 300
aaatatgtac tgtgcagcgc ttcccgataa tccccacaat gaagcccctg caagcaccat 360
caatacgcct ttcacatgag ctgatttcat atctttcacc cgtttctgta tgcgatatat 420
tgcatatttt aatagatgat cgacaaggcc gcaacctcct tcggcaaaaa atgatctcat 480
aaaataaatg aatagtattt tcataaaatg agctcaataa catattctaa caaatagcat 540
atagaaaaag ctagtgtttt tagcactagc tttttcttca ttctgatgaa ggttgttcaa 600
tattttgaat ccgttccatg atcgtcggat ggccgtattt aaaaatcttg acgagaaacg 660
gcgggtttgc ctcgctcagc ccggcttttg agagctcttg aaacgtcgaa accgctgcat 720
cgctgttttg cgtcagttca atcgcatact ggtcagcagc tttttcctga tgcctcgaaa 780
ctgcgttcgt aaatggagac gacgcgaaag agatgacccc catcagcatc agaagaagcg 840
gaagtgcggc tagatcggat tttcctgcaa tatgaaggct tcttccatag cggccgatga 900
tccgcttgta cagcttgtcg atcacataaa agacagcaag ggataaaagc agatacccgc 960
caagtcctat gtaaacatgc ttcatcacat agtgccccat ttcgtgcgcc atgatgctca 1020

```
ggagacc                                                            1027


<210> SEQ ID NO 66
<211> LENGTH: 21
<212> TYPE: DNA
<213> ORGANISM: Artificial Sequence
<220> FEATURE:
<223> OTHER INFORMATION: Oligonucleotide: PCR-amplification of aprE
      genomic region

<400> SEQUENCE: 66

ccggttgtca ttgatccttt a                                              21


<210> SEQ ID NO 67
<211> LENGTH: 21
<212> TYPE: DNA
<213> ORGANISM: Artificial Sequence
<220> FEATURE:
<223> OTHER INFORMATION: Oligonucleotide: PCR-amplification of aprE
      genomic region

<400> SEQUENCE: 67

atcctcctgc aaaaaccgta t                                              21


<210> SEQ ID NO 68
<211> LENGTH: 1022
<212> TYPE: DNA
<213> ORGANISM: Artificial Sequence
<220> FEATURE:
<223> OTHER INFORMATION: Fusion of 5- and 3-prime regions of amyB gene
      with flanking BsaI sites (homology regions)

<400> SEQUENCE: 68

ggtctcgacc cacaaggctg tcaaacgaaa aagcgtatca ggagattaac gacacgcaag     60

aaatgatcga aaaaatcagc ggacacctgc ctgtacactt gcgtcctcca tacggcggga    120

tcaatgattc cgtccgctcg ctttccaatc tgaaggtttc attgtgggat gttgatccgg    180

aagattggaa gtacaaaaat aagcaaaaga ttgtcaatca tgtcatgagc catgcgggag    240

acggaaaaat cgtcttaatg cacgatattt atgcaacgtc cgcagatgct gctgaagaga    300

ttattaaaaa gctgaaagca aaaggctatc aattggtaac tgtatctcag cttgaagaag    360

tgaagaagca gagaggctat tgaataaatg agtagaaagc gccatatcgg cgcttttctt    420

ttggaagaaa atatagggaa aatggtattt gttaaaaatt cggaatattt atacaatatc    480

atatgtttca cattgaaagg ggaggagaat ctagaagagc agagaggacg gatttcctga    540

aggaaatccg ttttttttatt ttgcccgtct tataaatttc tttgattaca ttttataatt    600

aattttaaca aagtgtcatc agccctcagg aaggacttgc tgacagtttg aatcgcatag    660

gtaaggcggg gatgaaatgg caacgttatc tgatgtagca aagaaagcaa atgtgtcgaa    720

aatgacggta tcgcgggtga tcaatcatcc tgagactgtg acggatgaat tgaaaaagct    780

tgttcattcc gcaatgaagg agctcaatta tataccgaac tatgcagcaa gagcgctcgt    840

tcaaaacaga acacaggtcg tcaagctgct catactggaa gaaatggata caacagaacc    900

ttattatatg aatctgttaa cgggaatcag ccgcgagctg gaccgtcatc attatgcttt    960

gcagcttgtc acaaggaaat ctctcaatat cggccagtgc gacggcatta tctcaggaga   1020

cc                                                                 1022


<210> SEQ ID NO 69
<211> LENGTH: 22
```

<212> TYPE: DNA
<213> ORGANISM: Artificial Sequence
<220> FEATURE:
<223> OTHER INFORMATION: Oligonucleotide: PCR-amplification of amyB genomic region

<400> SEQUENCE: 69
agaagcatga agggcatgcg ac 22

<210> SEQ ID NO 70
<211> LENGTH: 21
<212> TYPE: DNA
<213> ORGANISM: Artificial Sequence
<220> FEATURE:
<223> OTHER INFORMATION: Oligonucleotide: PCR-amplification of amyB genomic region

<400> SEQUENCE: 70
caacaacagg ctgtctgacg g 21

<210> SEQ ID NO 71
<211> LENGTH: 1022
<212> TYPE: DNA
<213> ORGANISM: Artificial Sequence
<220> FEATURE:
<223> OTHER INFORMATION: Fusion of 5- and 3-prime regions of sigF gene with flanking BsaI sites (homology regions)

<400> SEQUENCE: 71
ggtctcgacc caaaatcatt cgccttgagc aatcagagca gcgtgcactt gaaacgttgg 60
gggtggcgtc atgaaaaatg aaatgaacat tcagtttaca gcgctcagcc aaaatgaatc 120
gtttgcacgg gtgacagtcg ctgcttttat cgctcagctt gacccgacga tggatgaact 180
gaccgaaatt aaaacggtcg tatccgaagc ggtcacaaac gcgatcattc acggttatga 240
aaactcaggg cagggaaacg tatatatttc cgtcactctc gaggaccata ttgtctattt 300
aacgatccgc gacgaaggag tcggcatccc tgatcttgaa gaagcgcgcc agcccctgtt 360
cacgacaaag cctgaactcg agcggtcggg aatgggcttt acgatcatgg aaaatttcat 420
ggatgatatt tcgatcgact cctcacctga gatgggaacc acaatacact taacaaagca 480
cttatcaaaa agcaaagcgc tttgcaatta atgaggctgc tcatgttgca ggcagcctcg 540
gatgtccgat gaaaaaccgg acgctcttgg gagcgttccg gtttttttg tgtggtaatt 600 tatggtcttt tgcgcctttc tgaatgataa atgggatgta cttcatacta caactataac 660
catcatatag gaagtgaccc agatggaacg tcaagttttt atcagactcc gccaccggct 720
tgaggcagat ccggatgaat tgattttgct cggccatatc gcacaggtag cgggtgaccg 780
cggatacaaa gaaaagcttg aacggctgcc tatttatcag gtcagcaaag cggatcaaag 840
catggtggtg ctggacgtga tgaaggtgat tgaagctgta cataaatcgt ttcctgacct 900
tgatgtccaa accgtcggcg gttctgaaac catcgtggag atccaatatc cgaaaagggg 960
tctgtcgccc gtgcttttca tcgccgtctg gctgctcttg ttcgtcggtg cctcaggaga 1020
cc 1022

<210> SEQ ID NO 72
<211> LENGTH: 19
<212> TYPE: DNA
<213> ORGANISM: Artificial Sequence
<220> FEATURE:
<223> OTHER INFORMATION: Oligonucleotide: PCR-amplification of sigF genomic region

<400> SEQUENCE: 72
agcagctcgg cggagaaat 19

<210> SEQ ID NO 73
<211> LENGTH: 21
<212> TYPE: DNA
<213> ORGANISM: Artificial Sequence
<220> FEATURE:
<223> OTHER INFORMATION: Oligonucleotide: PCR-amplification of sigF genomic region

<400> SEQUENCE: 73
accttgcccg tcaccatttc g 21

<210> SEQ ID NO 74
<211> LENGTH: 1363
<212> TYPE: DNA
<213> ORGANISM: Artificial Sequence
<220> FEATURE:
<223> OTHER INFORMATION: Fusion of 5- and 3-prime regions of pga genes with flanking BsaI sites (homology regions)

<400> SEQUENCE: 74
ggtctcgacc cgaacactga aattttagac cgggctggga tatcgagaca tatatagggg 60
cgtttaatgg cgaatacagt aacaatgaga atagtaagaa aaattaaaaa tgttaaagtt 120
tgatgaatta tcattgaaaa aaattaatgg ctttttaaat cctaggattt taacctaaaa 180
tctgaagaaa taaggtggat cgaacgactc acaaaatatt tggatttgtc aatgaatccc 240
gctttatgct aaaagagatt ttcatttttt gatagatggt ctgattgtca taggacggat 300
ttgttttgaa gagggaacat tggtgacttt ttaacctgtt cgaaaagagc gaaaatacta 360
aaagaaaaga gacatcccgg ctgacagccc atttaaaggg gattgcggcc gggggaaaaa 420
agagatcctg aatccatcct tcaacctttc atctgaaata gggagaaaag tacaaaaatc 480
ataatgtcga attttgaaag cgcatactta aaacgctgac aaaaatctga taggaattaa 540
gaactttcga tttccaaaaa tatcaataaa aagataggca ttaatgactc gggcgaggtg 600
atctttgtca cggaaaattt cgtcgtcttc tgttacataa tgccgattgt gatttcatag 660
tgaaccctga tcccggttat aaaagacctg tgaaaagcgg ccggtttgaa agggaaacac 720
gacaattttc ttaaccggtc agtgtataaa gttttataga aaatcaggag gatatataca 780
tggttttggg gttcatgttt attgtattct tttgaaggga ataaaaactg acaaatttcg 840
actgaagcaa aatttgaaaa tgcatcacct taccaattcg ggatgggaac cgcacctcat 900
gttcatgacc tctttagaat atttcccttc atctttttaa tccgcgctta ggtgaaaaag 960
ctgatcatgc tgtgctgagc gtttcttctc gctatgacgc tgctgtacat gcaaaaaaag 1020
tcctttaaat atcccagttg aatgacgatg aaagaggaaa gaagaggagg aacagatcaa 1080
ttgataaaaa aagcggcaaa caaaaagttg gttttgtttt gtggaattgc ggtgctttgg 1140
atgtctttat ttttaacgaa tcataatgat gtacgcgccg atacgatcgg cgagaaaata 1200
gcggaaactg ccagacagct tgagggtgcg aaatacagct acggcggaga gaagccgaaa 1260
acggggtttg actcgtcagg ctttgtgcaa tatgtgtttc aatcgctcga tattacgctt 1320
ccgagaacgg taaaggaaca atcgactctt ggctcaggag acc 1363

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide: PCR-amplification of pga genomic region

<400> SEQUENCE: 75
aaagccttct cctctctatt 20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide: PCR-amplification of pga genomic region

<400> SEQUENCE: 76
ttcttgaaaa agacaaggtc 20

<210> SEQ ID NO 77
<211> LENGTH: 37
<212> TYPE: DNA
<213> ORGANISM: Artificial Sequence
<220> FEATURE:
<223> OTHER INFORMATION: Oligonucleotide: PCR-amplification of yitV 5-prime homologous region

<400> SEQUENCE: 77
agagaaggtc tcaacccttc aaaccggaga atgtgcc 37

<210> SEQ ID NO 78
<211> LENGTH: 33
<212> TYPE: DNA
<213> ORGANISM: Artificial Sequence
<220> FEATURE:
<223> OTHER INFORMATION: Oligonucleotide: PCR-amplification of yitV 5-prime homologous region

<400> SEQUENCE: 78
ttctctggtc tcggtttgac gcgcacttgt aag 33

<210> SEQ ID NO 79
<211> LENGTH: 42
<212> TYPE: DNA
<213> ORGANISM: Artificial Sequence
<220> FEATURE:
<223> OTHER INFORMATION: Oligonucleotide: PCR-amplification of yitV 3-prime homologous region

<400> SEQUENCE: 79
agagaaggtc tcaaaaccca tcatcataag tttaacatgt ag 42

<210> SEQ ID NO 80
<211> LENGTH: 38
<212> TYPE: DNA
<213> ORGANISM: Artificial Sequence
<220> FEATURE:
<223> OTHER INFORMATION: Oligonucleotide: PCR-amplification of yitV 3-prime homologous region

<400> SEQUENCE: 80
cctctctggt ctcatgagct gcccatcgta aagacatc 38

<210> SEQ ID NO 81
<211> LENGTH: 35
<212> TYPE: DNA
<213> ORGANISM: Artificial Sequence
<220> FEATURE:

-continued

```
<223> OTHER INFORMATION: Oligonucleotide: PCR-amplification of ypmR
      5-prime homologous region

<400> SEQUENCE: 81

agagaaggtc tcaaccccgt ttttaagcgg catct                              35


<210> SEQ ID NO 82
<211> LENGTH: 32
<212> TYPE: DNA
<213> ORGANISM: Artificial Sequence
<220> FEATURE:
<223> OTHER INFORMATION: Oligonucleotide: PCR-amplification of ypmR
      5-prime homologous region

<400> SEQUENCE: 82

ttctctggtc tcgaaacgaa gacctcccag ca                                 32


<210> SEQ ID NO 83
<211> LENGTH: 41
<212> TYPE: DNA
<213> ORGANISM: Artificial Sequence
<220> FEATURE:
<223> OTHER INFORMATION: Oligonucleotide: PCR-amplification of ypmR
      3-prime homologous region

<400> SEQUENCE: 83

agagaaggtc tcagtttgtg taccatgttt tgattctttt g                       41


<210> SEQ ID NO 84
<211> LENGTH: 40
<212> TYPE: DNA
<213> ORGANISM: Artificial Sequence
<220> FEATURE:
<223> OTHER INFORMATION: Oligonucleotide: PCR-amplification of ypmR
      3-prime homologous region

<400> SEQUENCE: 84

cctctctggt ctcatgaggg tggctgactt tatatttacg                         40
```

BACILLUS CELL WITH REDUCED LIPASE AND/OR ESTERASE SIDE ACTIVITIES

CROSS-REFERENCE TO RELATED APPLICATIONS

This is the U.S. national phase of International Application No. PCT/EP2021/077561, filed Oct. 6, 2021, which claims the benefit of European Patent Application Nos. 20200558.3, filed Oct. 7, 2020 and 21184275.2, filed Jul. 7, 2021.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "202696_Sequencelisting", which was created on Dec. 19, 2022 and is 118 kilobytes in size. The subject matter of the Sequence Listing is incorporated herein in its entirety by reference.

FIELD OF THE INVENTION

The present invention provides a modified *Bacillus* cell for the production of a compound of interest, wherein the *Bacillus* cell comprises a genetic modification that lead to decreased production of enzymes with lipase and/or esterase activity. The use of compounds of interest produced with said improved *Bacillus* host cells reduces the formation of malodour and/or off-flavour when used for applications such as washing or cleaning or as feed or food additives.

BACKGROUND OF THE INVENTION

Microorganisms of the *Bacillus* genus are widely applied as industrial workhorses for the production of valuable compounds, such as chemicals, polymers and proteins, in particular proteins like washing- and/or cleaning-active enzymes or enzymes used for feed and food applications. The biotechnological production of these useful substances is conducted via fermentation of such *Bacillus* species and subsequent purification of the product.

Often for the final use of these fermentation-derived substances, in particular enzymes, laborious removal of side products from the fermentation process is necessary. Depending on the processes complete removal of side products is difficult and economically not feasible. These side product of the fermentation process can be toxic and are often the cause for malodour formation or off-flavour (i.e., bad flavour) formation in the product formulation and its application. For some applications complete removal of side products is necessary, for instance, due to regulatory constraints.

WO2006000343 describes the construction of genetically modified *Bacillus* cells with decreased capability of production of malodorous or toxic compounds during fermentation of such *Bacillus* cells by targeting genes for inactivation that encode enzymes belonging to five metabolic pathways for the formation of odorous substances like isolvalerian acid, 2-methylbutyric acid, propyl acid, cadaverine and/or putrescine.

Also, lipases can be the cause of odour and flavour formation, a property that is used for the generation of an intense odour in cheese products (cf., e.g., U.S. Pat. No. 4,595,594). However, if these intense flavours or odours are not desired the addition of lipase might be prohibitive as well as in most alternative applications, like washing or cleaning, these intense odours are unwanted and need to be avoided.

WO9807817 describes an approach to reduce lipase-induced malodour in detergents by the addition of an antibody against a specific lipase to detergent compositions.

However, the addition of antibodies against lipases to the final product is very cost-intensive and not very effective. The interaction between antibody and lipase needs specific conditions especially with respect to salt concentration and pH, which are often not fulfilled in the applications to which the antibodies are added. Moreover, the generation of antibodies is laborious and specific to the epitope of the individual lipase used for antibody generation. Furthermore, the relevant lipase side activities produced by *Bacillus* cells are largely unknown. Various different lipases can be present as side products of *Bacillus* fermentation, which contribute to malodour and/or off-flavour formation. Not all of these lipases are captured by the specific antibody used. Hence, there is still a need for an improved way of reducing unwanted lipase side activities in product preparations obtained by fermentation of *Bacillus* cells.

US20030158070 mentions the YitV protein of *Bacillus subtilis* and classifies YitV as putative serine protease. However, the present inventors revealed that YitV comprises lipase/esterase activity.

BRIEF SUMMARY OF THE INVENTION

The present inventors identified the YitV and/or YpmR protein to be the major contributors to *Bacillus* derived lipase side activities and provided a recombinant *Bacillus* cell comprising a non-native reduction of the YitV and/or YpmR protein expression as a solution for reducing malodour and off-flavour formation in *Bacillus* derived fermentation products.

Thus, the present invention is directed to a recombinant *Bacillus* cell comprising a non-native reduction of the YitV and/or YpmR protein expression.

The present invention is also directed to a method for producing a compound of interest, preferably a protein of interest, comprising the fermentation of a *Bacillus* cell according to the present invention capable of producing the compound of interest, optionally comprising the step of purifying the compound of interest from the fermentation broth.

Moreover, the present invention is directed to a composition comprising the purified or partially purified compound of interest, preferably a protein of interest, obtained by the methods of the present invention and thereby comprising a reduced amount of lipase and/or esterase activity.

Furthermore, the present invention is directed to a method for reducing the formation of malodour or off-flavour in a composition comprising a compound of interest obtained by fermentation of a *Bacillus* cell comprising the fermentation of a *Bacillus* cell according to present invention capable of producing a compound of interest, purifying the compound of interest from the fermentation broth and providing a composition comprising the purified compound of interest.

DETAILED DESCRIPTION OF THE INVENTION

The present invention may be understood more readily by reference to the following detailed description of the embodiments of the invention and the examples included herein.

DEFINITIONS

Unless otherwise noted, the terms used herein are to be understood according to conventional usage by those of ordinary skill in the relevant art.

Before describing in detail exemplary embodiments of the present invention, definitions important for understanding the present invention are given. Unless stated otherwise or apparent from the nature of the definition, the definitions apply to all methods and uses described herein.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

Throughout this application, various publications are referenced. The disclosures of all of these publications and those references cited within those publications in their entireties are hereby incorporated by reference into this application in order to more fully describe the state of the art to which this invention pertains.

It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only.

"Parent" sequence (e.g., "parent enzyme" or "parent protein") is the starting sequences for introduction of changes (e.g. by introducing one or more amino acid substitutions) of the sequence resulting in "variants" of the parent sequences. Thus, the term "enzyme variant" or "sequence variant" or "protein variant" are used in reference to parent enzymes that are the origin for the respective variant enzymes. Therefore, parent enzymes include wild type enzymes and variants of wild-type enzymes which are used for development of further variants. Variant enzymes differ from parent enzymes in their amino acid sequence to a certain extent; however, variants at least maintain the enzyme properties of the respective parent enzyme. In one embodiment, enzyme properties are improved in variant enzymes when compared to the respective parent enzyme. In one embodiment, variant enzymes have at least the same enzymatic activity when compared to the respective parent enzyme or variant enzymes have increased enzymatic activity when compared to the respective parent enzyme.

In describing the protein variants, the abbreviations for single amino acids used according to the accepted IUPAC single letter or three letter amino acid abbreviation is used.

"Substitutions" are described by providing the original amino acid followed by the number of the position within the amino acid sequence, followed by the substituted amino acid. For example, the substitution of histidine at position 120 with alanine is designated as "His120Ala" or "H120A".

"Deletions" are described by providing the original amino acid followed by the number of the position within the amino acid sequence, followed by *. Accordingly, the deletion of glycine at position 150 is designated as "Gly150*" or G150*". Alternatively, deletions are indicated by e.g. "deletion of D183 and G184".

"Insertions" are described by providing the original amino acid followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

In cases where a substitution and an insertion occur at the same position, this may be indicated as S99SD+S99A or in short S99AD. In cases where an amino acid residue identical to the existing amino acid residue is inserted, it is clear that degeneracy in the nomenclature arises. If for example a glycine is inserted after the glycine in the above example this would be indicated by G180GG. Variants comprising multiple alterations are separated by "+", e.g., "Arg170Tyr+Gly195Glu" or "R170Y+G195E" representing a substitution of arginine and glycine at positions 170 and 195 with tyrosine and glutamic acid, respectively. Alternatively, multiple alterations may be separated by space or a comma e.g. R170Y G195E or R170Y, G195E respectively. Where different alterations can be introduced at a position, the different alterations are separated by a comma, e.g. "Arg170Tyr, Glu" and R170T, E, respectively, represents a substitution of arginine at position 170 with tyrosine or glutamic acid. Alternatively, different alterations or optional substitutions may be indicated in brackets, e.g., Arg170[Tyr, Gly] or Arg170{Tyr, Gly} or in short R170 [Y, G] or R170 {Y, G}.

Variants of the parent enzyme molecules may have an amino acid sequence which is at least n percent identical to the amino acid sequence of the respective parent enzyme having enzymatic activity with n being an integer between 50 and 100, preferably 50, 55, 60, 65, 70, 75, 80, 85, 90, 91, 92, 93, 94, 95, 96, 97, 98 or 99 compared to the full length polypeptide sequence. Variant enzymes described herein which are n percent identical when compared to a parent enzyme, have enzymatic activity.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

After aligning the two sequences, in a second step, an identity value shall be determined from the alignment. Therefore, according to the present invention the following calculation of percent-identity applies:

%-identity=(identical residues/length of the alignment region which is showing the respective sequence of this invention over its complete length)*100. Thus sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity".

For calculating the percent identity of two DNA sequences the same applies as for the calculation of percent identity of two amino acid sequences with some specifications. For DNA sequences encoding for a protein the pairwise alignment shall be made over the complete length of the coding region from start to stop codon excluding introns. For non-protein-coding DNA sequences the pairwise alignment shall be made over the complete length of the sequence of this invention, so the complete sequence of this invention is compared to another sequence, or regions out of another sequence. Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

Enzyme variants may be defined by their sequence similarity when compared to a parent enzyme. Sequence similarity usually is provided as "% sequence similarity" or "%-similarity". For calculating sequence similarity in a first step a sequence alignment has to be generated as described above. In a second step, the percent-similarity has to be calculated, whereas percent sequence similarity takes into account that defined sets of amino acids share similar properties, e.g., by their size, by their hydrophobicity, by their charge, or by other characteristics. Herein, the exchange of one amino acid with a similar amino acid is referred to as "conservative mutation". Enzyme variants comprising conservative mutations appear to have a minimal effect on protein folding resulting in certain enzyme properties being substantially maintained when compared to the enzyme properties of the parent enzyme.

For determination of %-similarity according to this invention the following applies, which is also in accordance with the BLOSUM62 matrix, which is one of the most used amino acids similarity matrix for database searching and sequence alignments Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W.

Conservative amino acid substitutions may occur over the full length of the sequence of a polypeptide sequence of a functional protein such as an enzyme. In one embodiment, such mutations are not pertaining the functional domains of an enzyme. In another embodiment conservative mutations are not pertaining the catalytic centers of an enzyme.

Therefore, according to the present invention the following calculation of percent-similarity applies:

%-similarity=[(identical residues+similar residues)/length of the alignment region which is showing the respective sequence of this invention over its complete length]*100. Thus sequence similarity in relation to comparison of two amino acid sequences herein is calculated by dividing the number of identical residues plus the number of similar residues by the length of the alignment region which is showing the respective sequence of this invention over its complete length. This value is multiplied with 100 to give "%-similarity".

Especially, variant enzymes comprising conservative mutations which are at least m percent similar to the respective parent sequences with m being an integer between 50 and 100, preferably 50, 55, 60, 65, 70, 75, 80, 85, 90, 91, 92, 93, 94, 95, 96, 97, 98 or 99 compared to the full length polypeptide sequence, are expected to have essentially unchanged enzyme properties. Variant enzymes described herein with m percent-similarity when compared to a parent enzyme, have enzymatic activity.

The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, sepharose beads or any other resin. The hybridisation process can furthermore occur with one of the complementary nucleic acids immobilised to a solid support such as a nitro-cellulose or nylon membrane or immobilised by e.g. photolithography to a carrier, including, but not limited to a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

This formation or melting of hybrids is dependent on various parameters, including but not limited thereto the temperature. An increase in temperature favours melting, while a decrease in temperature favours hybridisation. However, this hybrid forming process is not following an applied change in temperature in a linear fashion: the hybridisation process is dynamic, and already formed nucleotide pairs are supporting the pairing of adjacent nucleotides as well. So, with good approximation, hybridisation is a yes-or-no process, and there is a temperature, which basically defines the border between hybridisation and no hybridisation. This temperature is the melting temperature (Tm). Tm is the temperature in degrees Celsius, at which 50% of all molecules of a given nucleotide sequence are hybridised into a double strand, and 50% are present as single strands.

The melting temperature (Tm) is dependent from the physical properties of the analysed nucleic acid sequence and hence can indicate the relationship between two distinct sequences. However, the melting temperature (Tm) is also influenced by various other parameters, which are not directly related with the sequences, and the applied conditions of the hybridization experiment must be taken into account. For example, an increase of salts (e.g. monovalent cations) is resulting in a higher Tm.

Tm for a given hybridisation condition can be determined by doing a physical hybridisation experiment, but Tm can also be estimated in silico for a given pair of DNA sequences. In this embodiment, the equation of Meinkoth and Wahl (Anal. Biochem., 138:267-284, 1984) is used for stretches having a length of 50 or more bases: Tm=81.5° C.+16.6 (log M)+0.41 (% GC)–0.61 (% form)–500/L.

M is the molarity of monovalent cations, % GC is the percentage of guanosine and cytosine nucleotides in the DNA stretch, % form is the percentage of formamide in the hybridisation solution, and L is the length of the hybrid in base pairs. The equation is for salt ranges of 0.01 to 0.4 M and % GC in ranges of 30% to 75%.

While above Tm is the temperature for a perfectly matched probe, Tm is reduced by about 1° C. for each 1% of mismatching (Bonner et al., J. Mol. Biol. 81: 123-135, 1973): Tm=[81.5° C.+16.6(log M)+0.41 (% GC)–0.61 (% formamide)–500/L]–% non-identity.

This equation is useful for probes having 35 or more nucleotides and is widely referenced in scientific method literature (e.g. in: "Recombinant DNA Principles and Methodologies", James Greene, Chapter "Biochemistry of Nucleic acids", Paul S. Miller, page 55; 1998, CRC Press), in many patent applications (e.g. in: U.S. Pat. No. 7,026,149), and also in data sheets of commercial companies (e.g. "Equations for Calculating Tm" from www.genomics.agilent.com).

Other formulas for Tm calculations, which are less preferred in this embodiment, might be only used for the indicated cases:

For DNA-RNA hybrids (Casey, J. and Davidson, N. (1977) Nucleic Acids Res., 4:1539):

$$Tm = 79.8^\circ\text{ C.} + 18.5(\log M) + 0.58(\%\ GC) + 11.8(\%\ GC * \%\ GC) - 0.5(\%\ \text{form}) - 820/L.$$

For RNA-RNA hybrids (Bodkin, D. K. and Knudson, D. L. (1985) J. Virol. Methods, 10: 45):

$$Tm = 79.8^\circ\text{ C.} + 18.5(\log M) + 0.58(\%\ GC) + 11.8(\%\ GC * \%\ GC) - 0.35(\%\ \text{form}) - 820/L.$$

For oligonucleotide probes of less than 20 bases (Wallace, R. B., et al. (1979) Nucleic Acid Res. 6: 3535): Tm=2×n(A+T)+4×n(G+C), with n being the number of respective bases in the probe forming a hybrid.

For oligonucleotide probes of 20-35 nucleotides, a modified Wallace calculation could be applied: Tm=22+1.46 n(A+T)+2.92 n(G+C), with n being the number of respective bases in the probe forming a hybrid.

For other oligonucleotides, the nearest-neighbour model for melting temperature calculation should be used, together with appropriate thermodynamic data:

$$Tm = \left(\sum(\Delta Hd) + \Delta Hi\right)/\left(\sum(\Delta Sd) + \Delta Si + \Delta Sself + R \times \ln(cT/b)\right) + 16.6\log[\text{Na}+] - 273.15$$

(Breslauer, K. J., Frank, R., Blöcker, H., Marky, L. A. 1986 Predicting DNA duplex stability from the base sequence. Proc. Natl Acad. Sci. USA 833746-3750; Alejandro Panjkovich, Francisco Melo, 2005. Comparison of different melting temperature calculation methods for short DNA sequences. Bioinformatics, 21 (6): 711-722)

where:

Tm is the melting temperature in degrees Celsius;

ΣZ(ΔHd) and Σ(ΔSd) are sums of enthalpy and entropy (correspondingly), calculated over all internal nearest-neighbor doublets;

ΔSself is the entropic penalty for self-complementary sequences;

ΔHi and ΔSi are the sums of initiation enthalpies and entropies, respectively;

R is the gas constant (fixed at 1.987 cal/K-mol);

cT is the total strand concentration in molar units;

constant b adopts the value of 4 for non-self-complementary sequences or equal to 1 for duplexes of self-complementary strands or for duplexes when one of the strands is in significant excess.

The thermodynamic calculations assume that the annealing occurs in a buffered solution at pH near 7.0 and that a two-state transition occurs.

Thermodynamic values for the calculation can be obtained from Table 1 in (Alejandro Panjkovich, Francisco Melo, 2005. Comparison of different melting temperature calculation methods for short DNA sequences. Bioinformatics, 21 (6): 711-722), or from the original research papers (Breslauer, K. J., Frank, R., B16cker, H., Marky, L. A. 1986 Predicting DNA duplex stability from the base sequence. Proc. Natl Acad. Sci. USA 833746-3750; SantaLucia, J., Jr, Allawi, H. T., Seneviratne, P. A. 1996 Improved nearest-neighbor parameters for predicting DNA duplex stability. Biochemistry 353555-3562; Sugimoto, N., Nakano, S., Yoneyama, M., Honda, K. 1996 Improved thermodynamic parameters and helix initiation factor to predict stability of DNA duplexes. Nucleic Acids Res. 244501-4505).

For an in silico estimation of Tm according to this embodiment, first a set of bioinformatic sequence alignments between the two sequences are generated. Such alignments can be generated by various tools known to a person skilled in the art, like programs "Blast" (NCBI), "Water" (EMBOSS) or "Matcher" (EMBOSS), which are producing local alignments, or "Needle" (EMBOSS), which is producing global alignments. Those tools should be applied with their default parameter setting, but also with some parameter variations. For example, program "MATCHER" can be applied with various parameter for gapopen/gapextend (like 14/4; 14/2; 14/5; 14/8; 14/10; 20/2; 20/5; 20/8; 20/10; 30/2; 30/5; 30/8; 30/10; 40/2; 40/5; 40/8; 40/10; 10/2; 10/5; 10/8; 10/10; 8/2; 8/5; 8/8; 8/10; 6/2; 6/5; 6/8; 6/10) and program "WATER" can be applied with various parameter for gapopen/gapextend (like 10/0.5; 10/1; 10/2; 10/3; 10/4; 10/6; 15/1; 15/2; 15/3; 15/4; 15/6; 20/1; 20/2; 20/3; 20/4; 20/6; 30/1; 30/2; 30/3; 30/4; 30/6; 45/1; 45/2; 45/3; 45/4; 45/6; 60/1; 60/2; 60/3; 60/4; 60/6), and also these programs shall be applied by using both nucleotide sequences as given, but also with one of the sequences in its reverse complement form. For example, BlastN (NCBI) can be applied with an increased e-value cut-off (e.g. e+1 or even e+10) to also identify very short alignments, especially in data bases of small sizes.

Important is that local alignments are considered, since hybridisation may not necessarily occur over the complete length of the two sequences, but may be best at distinct regions, which then are determining the actual melting temperature. Therefore, from all created alignments, the alignment length, the alignment % GC content (in a more accurate manner, the % GC content of the bases which are matching within the alignment), and the alignment identity has to be determined. Then the predicted melting temperature (Tm) for each alignment has to be calculated. The highest calculated Tm is used to predict the actual melting temperature.

The term "hybridisation over the complete sequence of the invention" as defined herein means that for sequences longer than 300 bases when the sequence of the invention is fragmented into pieces of about 300 to 500 bases length, every fragment must hybridise. For example, a DNA can be fragmented into pieces by using one or a combination of restriction enzymes. A bioinformatic in silico calculation of Tm is then performed by the same procedure as described above, just done for every fragment. The physical hybridisation of individual fragments can be analysed by standard Southern analysis, or comparable methods, which are known to a person skilled in the art.

The term "stringency" as defined herein is describing the ease by which hybrid formation between two nucleotide sequences can take place. Conditions of a "higher stringency" require more bases of one sequence to be paired with the other sequence (the melting temperature Tm is lowered in conditions of "higher stringency"), conditions of "lower stringency" allow some more bases to be unpaired. Hence the degree of relationship between two sequences can be estimated by the actual stringency conditions at which they are still able to form hybrids. An increase in stringency can be achieved by keeping the experimental hybridisation temperature constant and lowering the salts concentrations, or by keeping the salts constant and increasing the experimental hybridisation temperature, or a combination of these parameter. Also an increase of formamide will increase the stringency. The skilled artisan is aware of additional parameters which may be altered during hybridisation and which will either maintain or change the stringency conditions (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical hybridisation experiment is done by an initial hybridisation step, which is followed by one to several washing steps. The solutions used for these steps may contain additional components, which are preventing the degradation of the analyzed sequences and/or prevent unspecific background binding of the probe, like EDTA, SDS, fragmented sperm DNA or similar reagents, which are known to a person skilled in the art (Sambrook et al. (2001) Molecular Cloning: a laboratory manual, 3$^{rd}$ Edition, Cold Spring Harbor Laboratory Press, CSH, New York or to Current Protocols in Molecular Biology, John Wiley & Sons, N.Y. (1989 and yearly updates).

A typical probe for a hybridisation experiment is generated by the random-primed-labelling method, which was initially developed by Feinberg and Vogelstein (Anal. Biochem., 132 (1), 6-13 (1983); Anal. Biochem., 137 (1), 266-7 (1984) and is based on the hybridisation of a mixture of all possible hexanucleotides to the DNA to be labelled. The labelled probe product will actually be a collection of fragments of variable length, typically ranging in sizes of 100-1000 nucleotides in length, with the highest fragment concentration typically around 200 to 400 bp. The actual size range of the probe fragments, which are finally used as probes for the hybridisation experiment, can also be influenced by the used labelling method parameter, subsequent purification of the generated probe (e.g. agarose gel), and the size of the used template DNA which is used for labelling (large templates can e.g. be restriction digested using a 4 bp cutter, e.g. HaeIII, prior labeling).

For the present invention, the sequence described herein is analysed by a hybridisation experiment, in which the probe is generated from the other sequence, and this probe is generated by a standard random-primed-labelling method. For the present invention, the probe is consisting of a set of labelled oligonucleotides having sizes of about 200-400 nucleotides. A hybridisation between the sequence of this invention and the other sequence means, that hybridisation of the probe occurs over the complete sequence of this invention, as defined above. The hybridisation experiment is done by achieving the highest stringency by the stringency of the final wash step. The final wash step has stringency conditions comparable to the stringency conditions of at least Wash condition 1: 1.06×SSC, 0.1% SDS, 0% formamide at 50° C., in another embodiment of at least Wash condition 2: 1.06×SSC, 0.1% SDS, 0% formamide at 55° C., in another embodiment of at least Wash condition 3: 1.06×SSC, 0.1% SDS, 0% formamide at 60° C., in another embodiment of at least Wash condition 4: 1.06×SSC, 0.1% SDS, 0% formamide at 65° C., in another embodiment of at least Wash condition 5: 0.52×SSC, 0.1% SDS, 0% formamide at 65° C., in another embodiment of at least Wash condition 6: 0.25×SSC, 0.1% SDS, 0% formamide at 65° C., in another embodiment of at least Wash condition 7: 0.12×SSC, 0.1% SDS, 0% formamide at 65° C., in another embodiment of at least Wash condition 8: 0.07×SSC, 0.1% SDS, 0% formamide at 65° C.

A "low stringent wash" has stringency conditions comparable to the stringency conditions of at least Wash condition 1, but not more stringent than Wash condition 3, wherein the wash conditions are as described above.

A "high stringent wash" has stringency conditions comparable to the stringency conditions of at least Wash condition 4, in another embodiment of at least Wash condition 5, in another embodiment of at least Wash condition 6, in another embodiment of at least Wash condition 7, in another embodiment of at least Wash condition 8, wherein the wash conditions are as described above.

The term "heterologous" (or exogenous or foreign or recombinant or non-native) polypeptide is defined herein as a polypeptide that is not native to the host cell, a polypeptide native to the host cell in which structural modifications, e.g., deletions, substitutions, and/or insertions, have been made by recombinant DNA techniques to alter the native polypeptide, or a polypeptide native to the host cell whose expression is quantitatively altered or whose expression is directed from a genomic location different from the native host cell as a result of manipulation of the DNA of the host cell by recombinant DNA techniques, e.g., a stronger promoter. Similarly, the term "heterologous" (or exogenous or foreign or recombinant or non-native) polynucleotide refers to a polynucleotide that is not native to the host cell, a polynucleotide native to the host cell in which structural modifications, e.g., deletions, substitutions, and/or insertions, have been made by recombinant DNA techniques to alter the native polynucleotide, or a polynucleotide native to the host cell whose expression is quantitatively altered as a result of manipulation of the regulatory elements of the polynucleotide by recombinant DNA techniques, e.g., a stronger promoter, or a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterized that the two or more polynucleotide sequences or two or more amino acid sequences are naturally not occurring in the specific combination with each other.

For the purposes of the invention, "recombinant" (or transgenic) with regard to a cell or an organism means that the cell or organism contains a heterologous polynucleotide which is introduced by man by gene technology and with regard to a polynucleotide includes all those constructions brought about by man by gene technology/recombinant DNA techniques in which either (a) the sequence of the polynucleotide or a part thereof, or
(b) one or more genetic control sequences which are operably linked with the polynucleotide, including but not limited thereto a promoter, or
(c) both a) and b)

are not located in their wildtype genetic environment or have been modified.

The term "native" (or wildtype or endogenous) cell or organism and "native" (or wildtype or endogenous) polynucleotide or polypeptide refers to the cell or organism as found in nature and to the polynucleotide or polypeptide in question as found in a cell in its natural form and genetic environment, respectively (i.e., without there being any human intervention).

As used herein the term "coding region" (or ORF—open reading frame) when used in reference to a structural gene refers to the nucleotide sequences which encode the amino acids found in the nascent polypeptide as a result of translation of a mRNA molecule. The coding region is bounded on the 5-side by the nucleotide triplet "ATG" which encodes the initiator methionine and on the 3'-side by one of the three triplets which specify stop codons (i.e., TAA, TAG, TGA). Alternatively, the nucleotide triplet can be "GTG" or "TTG" and is recognized as the start nucleotide triplet as 5' to said nucleotide triplet the ribosome binding site (Shine Dalgarno) is located in a distance of 4 nucleotides to 12 nucleotides. Genomic forms of a gene may also include sequences located on both the 5'- and 3'-end of the sequences which are present on the RNA transcript, i.e. these sequences are located 5' or 3' to the non-translated sequences present on the mRNA transcript. Furthermore the 5' and 3' sequences also referred to as 'flanking' sequences or regions may further contain regulatory sequences such as within the 5' sequence promoters and enhancers which control or influence the transcription of the gene and the ribosome binding site (Shine Dalgarno) which controls or influences translation of the mRNA and within the 3' sequence contain sequences which direct the termination of transcription and posttranscriptional cleavage.

Herein, "complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

The term "gene expression" means the transcription of a specific gene or specific genes or specific nucleic acid construct. The term "gene expression" in particular means the transcription of a gene or genes or genetic construct into structural RNA (e.g., rRNA, tRNA) or mRNA with or without subsequent translation of the latter into a protein. The process includes transcription of DNA and processing of the resulting mRNA product. The term "expression of a protein" specifically means the transcription of a gene or genes or genetic construct into mRNA with subsequent translation of the latter into a protein.

The term "reduction of expression of a protein" shall mean a reduced amount of the protein being produced by the cell, for instance, by a reduced transcription or reduced translation.

The term "non-native reduction of expression of a protein" shall mean a reduced amount of the protein being produced by the cell achieved by any kind genetic modification by human intervention, in particular recombinant DNA techniques, applied to the cell compared to the cell not subject to the genetic modification, i.e., the respective parent host cell.

The term "non-native complete or partial deletion of a gene" shall mean any kind genetic modification by human intervention, in particular recombinant DNA techniques, applied to the cell compared to the cell not subject to the genetic modification resulting in a complete for partial removal of the gene, i.e., the respective parent host cell.

The term "inactivation" (also called herein "functional inactivation") in connection with a gene means that the functionality of said gene has been reduced compared to the functionality of the gene in the parent host cell, so that the gene produces no active protein or a reduced amount of active protein, preferably the inactivated gene produces no active protein. A parent host cell is a host cell, which differs from the host cell of the present invention only in that the gene has not been inactivated, i.e., a corresponding host cell with a functional gene. The functionality of the gene can be inactivated by various means known to the person skilled in the art. In a preferred embodiment, the yitV gene of the parent host cell is inactivated so that the host cell does not produce active YitV protein. In a preferred embodiment, the ypmR gene of the parent host cell is inactivated so that the host cell does not produce active YpmR protein. In a particularly preferred embodiment, the yitV and the ypmR gene of the parent host cell are inactivated so that the host cell does not produce active YitV protein and no active YpmR protein.

The terms "genome" or "genomic DNA" is referring to the heritable genetic information of a host organism. In eukaryotes said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus. In prokaryotes said genomic DNA comprises the chromosomal DNA within the bacterial cell.

As used herein, a "flanking" sequence or region refers to any sequence that is either 5' also referred to as "upstream' or 3' also referred to as "downstream" of the sequence being discussed (e.g. for sequences A-B-C, sequence B is flanked by the A and C sequences)

The terms "polynucleotide", "nucleic acid sequence", "nucleotide sequence", "nucleic acid", "nucleic acid molecule" are used interchangeably herein and refer to nucleotides, either ribonucleotides or deoxyribonucleotides or a combination of both, in a polymeric unbranched form of any length. "Polynucleotides" are composed of monomers, which are "nucleotides" made of three components: a pentose sugar, a phosphate group, and a nitrogenous base.

The term "selectable marker" (or marker) comprises genes encoding for polypeptides when being expressed in a bacterial host cell under conditions that effectively express said marker polypeptide allow growth or increased growth compared to a control host cell. Such positive selection by, e.g. antibiotic resistance markers such as ampicillin, kanamycin, erythromycin, chloramphenicol or tetracycline and auxotrophic resistance markers have been used to e.g. retain plasmids within a cell, or to select on host cells with successful gene integration.

Likewise, "counterselection markers" are understood as genes encoding for polynucleotides when being expressed in a bacterial host cells under conditions that effectively express said counterselection polypeptide, optionally in the presence of an effective amount of counterselection agent for the counterselection polypeptide (if required) are toxic to the host cell and/or result in decreased growth compared to a control host cell. Counterselection markers are known in the art and have been used for plasmid removal, selection marker removal or removal of integrated plasmid from the host cell chromosome.

The term "foreign" (or exogenous, or non-native) refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term "nucleic acid construct" is synonymous with the term "expression cassette" when the nucleic acid construct contains the control sequences required for expression of a polynucleotide.

The term "control sequence" is defined herein to include all sequences affecting the expression of a polynucleotide, including but not limited thereto, the expression of a polynucleotide encoding a polypeptide. Each control sequence may be native or foreign to the polynucleotide or native or foreign to each other. Such control sequences include, but are not limited to, promoter sequence, 5'-UTR (also called leader sequence), ribosomal binding site (RBS, shine dalgarno sequence), 3'-UTR, and transcription start and stop sites.

The term "functional linkage" or "operably linked" with respect to regulatory elements, is to be understood as meaning the sequential arrangement of a regulatory element (including but not limited thereto a promoter) with a nucleic acid sequence to be expressed and, if appropriate, further regulatory elements (including but not limited thereto a terminator) in such a way that each of the regulatory elements can fulfil its intended function to allow, modify, facilitate or otherwise influence expression of said nucleic acid sequence. For example, a control sequence is placed at an appropriate position relative to the coding sequence of the polynucleotide sequence such that the control sequence directs the expression of the coding sequence of a polypeptide. Preferred arrangements are those in which the nucleic acid sequence to be expressed recombinantly is positioned behind the sequence acting as promoter, so that the two sequences are linked covalently to each other. In one embodiment, the nucleic acid sequence to be transcribed is located behind the promoter in such a way that the transcription start is identical with the desired beginning of the RNA. Functional linkage, and an expression construct, can be generated by means of customary recombination and cloning techniques as described (e.g., Sambrook, J. and Russell, D. W. Molecular cloning. A laboratory manual, 3rd ed, Cold Spring Harbor Laboratory Press, Cold Spring Harbor, N Y. 2001.); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands; Plant Molecular Biology Labfax (1993) by R. D. D. Croy, published by BIOS Scientific Publications Ltd (UK) and Blackwell Scientific Publications (UK)). However, further sequences, including but not limited thereto a sequence, which acts as a linker with specific cleavage sites for restriction enzymes, or as a signal peptide, may also be positioned between the two sequences. The insertion of sequences may also lead to the expression of fusion proteins.

A "promoter" or "promoter sequence" is a nucleotide sequence located upstream of a gene on the same strand as the gene that enables that gene's transcription. Promoter is followed by the transcription start site of the gene. Promoter is recognized by RNA polymerase (together with any required transcription factors), which initiates transcription. A functional fragment or functional variant of a promoter is a nucleotide sequence which is recognizable by RNA polymerase, and capable of initiating transcription.

An "active promoter fragment", "active promoter variant", "functional promoter fragment" or "functional promoter variant" describes a fragment or variant of the nucleotide sequences of a promoter, which still has promoter activity.

The term "transcription start site" or "transcriptional start site" shall be understood as the location where the transcription starts at the 5' end of a gene sequence. In prokaryotes the first nucleotide, referred to as +1 is in general an adenosine (A) or guanosine (G) nucleotide. In this context, the terms "sites" and "signal" can be used interchangeably herein.

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG, CTG or TTG and ends with a stop codon such as TAA, TAG, or TGA. The coding sequence may be a DNA, cDNA, synthetic, or recombinant nucleotide sequence. The start codon can also be named herein as "translational start signal" or "translational start site". The stop codon can also be named herein as "translational stop signal" or "translational stop site".

The term "expression vector" is defined herein as a linear or circular DNA molecule that comprises a polynucleotide that is operably linked to one or more control sequences that provides for the expression of the polynucleotide.

The term "host cell", as used herein, includes any cell type that is susceptible to transformation, transfection, transduction, conjugation, and the like with a nucleic acid construct or expression vector.

The term "introduction" and variations thereof are defined herein as the transfer of a DNA into a host cell. The introduction of a DNA into a host cell can be accomplished by any method known in the art, including, the not limited to, transformation, transfection, transduction, conjugation, or DNA uptake mechanisms (e.g. competency, or induced competency) well known for *Bacillus* (WO08079895). Likewise, the term "incoming" DNA is referred to as the DNA transferred into a bacterial host cell.

The term "donor cell" is defined herein as a cell that is the source of DNA introduced by any means to another cell.

The term "recipient cell" is defined herein as a cell into which DNA is introduced.

The term "fermentation in industrial scale" (also called large-scale fermentation) refers to fermentation processes with fermenter volumes of greater than or equal to 20 liters.

The term "operon" is understood herein as a unit of genomic DNA, containing a single promoter, and one or more genes, all of which are transcribed from that single promoter. The genes in the operon may overlap, or may have untranslated regions (UTRs) between each other. These UTRs may optionally have additional control elements, affecting translational efficiency.

As used herein, the term "vector" refers to an extrachromosomal circular DNA. A vector may be capable of autonomously replicating in the host cell, or not. The term "plasmid" refers to an extrachromosomal circular DNA, i.e. a vector that is autonomously replicating in the host cell. Thus, a plasmid is understood as extrachromosomal vector (and shall not be stably integrated in the bacterial chromosome).

Herein, an "enzyme having esterase activity is a hydrolase enzyme that splits esters into an acid and an alcohol in a chemical reaction with water called hydrolysis.

The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively.

DETAILED DESCRIPTION

Enzymes Having Lipase and/or Esterase Activity

The present invention is directed to a *Bacillus* cell comprising a reduced expression of one or more proteins having lipase and/or esterase activity. Preferably, the recombinant *Bacillus* cell comprising a non-native reduction of the YitV and/or YpmR protein expression. Most preferably, the recombinant *Bacillus* cell comprising a non-native reduction of the YitV and YpmR protein expression.

Preferably, the YitV protein, which expression is reduced, is selected from the group consisting of:

(a) a YitV protein having at least 70%, at least 75%, at least 80%, at least 85%, at least 90%, at least 92%, at least 95%, at least 96%, at least 97%, at least 98%, at least 99%, or even 100% identity with SEQ ID NO: 2;

(b) a YitV protein encoded by a polynucleotide having at least 70%%, at least 75%, at least 80%, at least 85%, at least 90%, at least 92%, at least 95%, at least 96%, at least 97%, at least 98%, at least 99%, or even 100% identity with SEQ ID NO: 32;

(c) a YitV protein encoded by a polynucleotide that hybridizes under high stringency conditions with (i) a polynucleotide comprising SEQ ID NO: 32 or (ii) the full-length complement of (i);

(d) a variant of the YitV protein of SEQ ID NO: 2 comprising a substitution, deletion, and/or insertion at one or more positions and having lipase and/or esterase activity;

(e) a YitV protein encoded by a polynucleotide that differs from SEQ ID NO: 32 due to the degeneracy of the genetic code.

Preferably, the YitV protein, which expression is reduced, is a YitV protein having at least 80%, at least 85%, at least 90%, at least 92%, at least 95%, at least 96%, at least 97%, at least 98%, at least 99%, or even 100% identity with SEQ ID NO: 2.

Preferably, the YpmR protein, which expression is reduced, is selected from the group consisting of:

(a) a YpmR protein having at least 70%, at least 75%, at least 80%, at least 85%, at least 90%, at least 92%, at least 95%, at least 96%, at least 97%, at least 98%, at least 99%, or even 100% identity with SEQ ID NO: 10;

(b) a YpmR protein encoded by a polynucleotide having at least 70%, at least 75%, at least 80%, at least 85%, at least 90%, at least 92%, at least 95%, at least 96%, at least 97%, at least 98%, at least 99%, or even 100% identity with SEQ ID NO: 40;

(c) a YpmR protein encoded by a polynucleotide that hybridizes under high stringency conditions with (i) a polynucleotide comprising SEQ ID NO: 40 or (ii) the full-length complement of (i);

(d) a variant of the YpmR protein of SEQ ID NO: 10 comprising a substitution, deletion, and/or insertion at one or more positions and having lipase and/or esterase activity;

(e) a YpmR protein encoded by a polynucleotide that differs from SEQ ID NO: 40 due to the degeneracy of the genetic code.

Preferably, the YpmR protein, which expression is reduced, is a YpmR protein having at least 80%, at least 85%, at least 90%, at least 92%, at least 95%, at least 96%, at least 97%, at least 98%, at least 99%, or even 100% identity with SEQ ID NO: 10.

Preferably, the recombinant *Bacillus* cell comprising a non-native reduction of the expression of a protein having lipase and/or esterase activity, wherein the protein comprises an amino acid sequence having at least 70%, at least 75%, at least 80%, at least 85%, at least 90%, at least 92%, at least 95%, at least 96%, at least 97%, at least 98%, at least 99%, or even 100% to SEQ ID NO: 2 or 10.

In one embodiment, the present invention refers to a recombinant *Bacillus* cell, preferably a *Bacillus licheniformis* cell, comprising an inactivation of the yitV and ypmR gene.

Preferably the yitV gene encodes a YitV protein that is selected from the group consisting of:

(a) a YitV protein having at least 70% identity with SEQ ID NO: 2;

(b) a YitV protein encoded by a polynucleotide having at least 70% identity with SEQ ID NO: 32;

(c) a YitV protein encoded by a polynucleotide that hybridizes under high stringency conditions with (i) a polynucleotide comprising SEQ ID NO: 32 or (ii) the full-length complement of (i);

(d) a variant of the YitV protein of SEQ ID NO: 2 comprising a substitution, deletion, and/or insertion at one or more positions and having lipase and/or esterase activity;

(e) a YitV protein encoded by a polynucleotide that differs from SEQ ID NO: 32 due to the degeneracy of the genetic code.

Preferably, the ypmR gene encodes a YpmR protein that is selected from the group consisting of:

(a) a YpmR protein having at least 70% identity with SEQ ID NO: 10;

(b) a YpmR protein encoded by a polynucleotide having at least 70% identity with SEQ ID NO: 40;

(c) a YpmR protein encoded by a polynucleotide that hybridizes under high stringency conditions with (i) a polynucleotide comprising SEQ ID NO: 40 or (ii) the full-length complement of (i);

(d) a variant of the YpmR protein of SEQ ID NO: 10 comprising a substitution, deletion, and/or insertion at one or more positions and having lipase and/or esterase activity;

(e) a YpmR protein encoded by a polynucleotide that differs from SEQ ID NO: 40 due to the degeneracy of the genetic code.

However, also other proteins having lipase and/or esterase activity can be reduced in their expression level in the *Bacillus* cell. Preferably one or more of the following proteins having lipase and/or esterase activity or variants or homologues thereof is reduced in the expression in the *Bacillus* cell as shown in Table 1:

| Gene name | Function | PRT | DNA | Accession |
|---|---|---|---|---|
| yhfR | putative phosphatase | SEQ ID 1 | SEQ ID 31 | PF14606.7 |
| yitV | putative peptidase | SEQ ID 2 | SEQ ID 32 | PF02230.17 |
| yesT | rhamnogalacturonan acety-lesterase | SEQ ID 3 | SEQ ID 33 | PF13472.7 |
| yesT | rhamnogalacturonan acety-lesterase | SEQ ID 3 | SEQ ID 33 | PF00657.23 |
| unknown | putative carbohydrate esterase | SEQ ID 4 | SEQ ID 34 | PF13472.7 |
| unknown | putative carbohydrate esterase | SEQ ID 4 | SEQ ID 34 | PF00657.23 |
| yesY | putative rhamnogalac-turonan acetylesterase | SEQ ID 5 | SEQ ID 35 | PF13472.7 |
| yes Y | putative rhamnogalac-turonan acetylesterase | SEQ ID 5 | SEQ ID 35 | PF00657.23 |
| unknown | hypothetical protein | SEQ ID 6 | SEQ ID 36 | PF01764.26 |
| fliG | flagellar motor switch protein | SEQ ID 7 | SEQ ID 37 | PF03280.15 |
| yisY | AB hydrolase superfamily protein | SEQ ID 8 | SEQ ID 38 | PF01764.26 |
| yisY | AB hydrolase superfamily protein | SEQ ID 8 | SEQ ID 38 | PF03583.15 |
| yisY | AB hydrolase superfamily protein | SEQ ID 8 | SEQ ID 38 | PF02230.17 |
| mhqD | putative hydrolase | SEQ ID 9 | SEQ ID 39 | PF02230.17 |
| ypmR | putative esterase | SEQ ID 10 | SEQ ID 40 | PF13472.7 |
| ypmR | putative esterase | SEQ ID 10 | SEQ ID 40 | PF00657.23 |
| ypmR | putative esterase | SEQ ID 10 | SEQ ID 40 | PF14606.7 |
| lip | putative lipase | SEQ ID 11 | SEQ ID 41 | PF01674.19 |
| yqiL | hypothetical protein | SEQ ID 12 | SEQ ID 42 | PF01764.26 |
| yqeF | putative lipoprotein | SEQ ID 13 | SEQ ID 43 | PF13472.7 |
| yqeF | putative lipoprotein | SEQ ID 13 | SEQ ID 43 | PF00657.23 |
| unknown | putative lipolytic enzyme | SEQ ID 14 | SEQ ID 44 | PF01764.26 |
| unknown | putative lipolytic enzyme | SEQ ID 14 | SEQ ID 44 | PF02230.17 |
| ytaP | putative hydrolase | SEQ ID 15 | SEQ ID 45 | PF03583.15 |
| ytpA | phospholipase | SEQ ID 16 | SEQ ID 46 | PF02230.17 |
| ytmA | putative dipeptidylpeptidase | SEQ ID 17 | SEQ ID 47 | PF02230.17 |
| ytmA | putative dipeptidylpeptidase | SEQ ID 17 | SEQ ID 47 | PF03583.15 |
| ytxM | 2-succinyl-6-hydroxy-2, 4-cyclohexadiene-1-carbox-ylate synthase | SEQ ID 18 | SEQ ID 48 | PF02230.17 |
| yugF | alpha/beta hydrolase | SEQ ID 19 | SEQ ID 49 | PF02230.17 |
| yugF | alpha/beta hydrolase | SEQ ID 19 | SEQ ID 49 | PF01764.26 |
| unknown | dipeptidylpeptidase | SEQ ID 20 | SEQ ID 50 | PF03583.15 |
| unknown | dipeptidylpeptidase | SEQ ID 20 | SEQ ID 50 | PF02230.17 |
| yuxL | putative acylaminoacyl-pep-tidase | SEQ ID 21 | SEQ ID 51 | PF02230.17 |
| unknown | phage putative hydrolase protein | SEQ ID 22 | SEQ ID 52 | PF01764.26 |
| besA | trilactone hydrolase | SEQ ID 23 | SEQ ID 53 | PF02230.17 |
| unknown | rhamnogalacturonan acety-lesterase | SEQ ID 24 | SEQ ID 54 | PF13472.7 |
| IchAD | lichenysin synthase | SEQ ID 25 | SEQ ID 55 | PF02230.17 |
| unknown | putative esterase | SEQ ID 26 | SEQ ID 56 | PF02230.17 |
| lipC | spore germination lipase LipC | SEQ ID 27 | SEQ ID 57 | PF13472.7 |
| lipC | spore germination lipase LipC | SEQ ID 27 | SEQ ID 57 | PF00657.23 |
| unknown | putative esterase/lipase | SEQ ID 28 | SEQ ID 58 | PF02230.17 |
| unknown | putative esterase/lipase | SEQ ID 28 | SEQ ID 58 | PF03583.15 |

-continued

| Gene name | Function | PRT | DNA | Accession |
|---|---|---|---|---|
| yrhL | putative peptidoglycan O-acetyltransferase | SEQ ID 29 | SEQ ID 59 | PF13472.7 |
| yrhL | putative peptidoglycan O-acetyltransferase | SEQ ID 29 | SEQ ID 59 | PF00657.23 |
| unknown | hypothetical protein | SEQ ID 30 | SEQ ID 60 | PF02230.17 |

Thus, the recombinant *Bacillus* cell may comprise a non-native reduction of the expression of one or more proteins having lipase and/or esterase activity, wherein the one or more proteins having lipase and/or esterase activity is selected from the group of proteins comprising an amino acid sequence having at least 70%, at least 75%, at least 80%, at least 85%, at least 90%, at least 92%, at least 95%, at least 96%, at least 97%, at least 98%, at least 99%, or even 100% to an amino acid sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In one embodiment, the recombinant *Bacillus* cell comprises an inactivation of the yitV gene and/or YpmR gene and in addition an inactivation of one or more of the other genes listed in the Table 1.

Thus, in one embodiment the recombinant *Bacillus* cell comprises a non-native reduction of the expression of one or more proteins having lipase and/or esterase activity, wherein the one or more proteins having lipase and/or esterase activity is selected from the group of proteins comprising an amino acid sequence having at least 70%, at least 75%, at least 80%, at least 85%, at least 90%, at least 92%, at least 95%, at least 96%, at least 97%, at least 98%, at least 99%, or even 100% to an amino acid sequence selected from the group consisting of SEQ ID NO: 2 and/or 10, and comprises a non-native reduction of the expression of one or more proteins having lipase and/or esterase activity, wherein the one or more proteins having lipase and/or esterase activity is selected from the group of proteins comprising an amino acid sequence having at least 70%, at least 75%, at least 80%, at least 85%, at least 90%, at least 92%, at least 95%, at least 96%, at least 97%, at least 98%, at least 99%, or even 100% to an amino acid sequence selected from the group consisting of SEQ ID NO: 1, 3, 4, 5, 6, 7, 8, 9, 11, 12, 13, 14, 15, 16, 17, 18, 19, 20, 21, 22, 23, 24, 25, 26, 27, 28, 29, or 30.

Host Cells

Various host cells can be used for the production of compounds of interest as described herein. Host cells comprising the genetic constructs described herein can be obtained by one of the methods described herein for introducing the polynucleotides into such host cells. In the methods of the present invention, the bacterial host cell is a *Bacillus* cell.

The *Bacillus* cell of the present invention has been modified to have a reduced expression of the endogenous YitV and/or YpmR protein.

The reduction of the expression of the YitV and/or YpmR protein can be achieved by various means known to the skilled person in the art. The reduction of the expression of the YitV and/or YpmR protein can be achieved by a non-native reduced transcription or non-native reduced translation.

In one embodiment, the reduction of expression of the YitV and/or YpmR protein is achieved by inactivation of the gene coding for the YitV and/or YpmR protein. Preferably, the reduction of the expression of the YitV and/or YpmR protein is achieved by a complete or partial deletion of the yitV and/or ypmR gene. Alternatively, the reduction of the expression of the YitV and/or YpmR protein is achieved by a partial deletion of the promoter region of the gene coding for the YitV and/or YpmR protein.

The inactivation of a gene as referred to herein may be achieved by any method deemed appropriate, i.e. that a gene encoding region and/or control sequence of a gene is entirely or partially modified by means such as deletion, insertion, substitution of one or more nucleotides or applied mutagenesis by chemical agents (e.g. NTG, EMS) or UV radiation followed by screening and selection resulting in functional inactivation, i.e. absence or decrease in expression and/or absence or decrease of enzyme activity of the encoded polypeptide. In simple terms, a “deletion” is defined as a change in either nucleotide or amino acid sequence in which one or more nucleotides or amino acid residues, respectively, have been removed (i.e., are absent). Thus, a deletion host cell has fewer nucleotides or amino acids than the respective parent host cell. The absence or decrease of enzymatic activity can be detected by measuring the absence or decreased specific enzyme activity of the corresponding polypeptide having enzyme activity (e.g. at least 25% decrease, at least 50% decrease, at least 75% decrease, at least 85% decrease, at least 95% decrease, or preferable 100% decrease). The inactivation can also be measured by the absence or decrease of corresponding mRNA of the host cell (e.g. at least 25% decrease, at least 50% decrease, at least 75% decrease, at least 85% decrease, at least 95% decrease, or preferable 100% decrease) with techniques known in the art. Inactivation of a particular gene of interest, or genomic region of interest can be generated by methods known in the art, for example, deletion/insertion/substitution by homologous recombination, gene silencing or applied mutagenesis Gene silencing can be achieved by introducing into the bacterial host cell antisense expression constructs that result in antisense RNAs complementary to the mRNA of the gene or genes targeted for inactivation respectively, thereby inhibiting expression of said genes. Gene silencing might also be achieved by introducing into the bacterial host cell siRNA expression constructs. Alternatively, the expression of said genes can be inhibited by blocking transcriptional initiation or transcriptional elongation through the mechanism of CRISPR-inhibition (e.g., as described in WO18009520).

Gene inactivation can be achieved by homologous recombination, i.e. an incoming DNA molecule comprises sequences that are homologous to the 5' and 3' flanking sequences of the target sequence on the chromosome of the host cell (e.g. *Bacillus*) to be inactivated. Subsequently the sequence between said flanking sequences is replaced by the homologous sequences of the incoming DNA molecule in the process of homologous recombination, i.e. the sequence is deleted from the chromosome. Likewise “gene integration", i.e. a DNA sequence such as a gene expression cassette with or without a selectable marker, can be integrated into the chromosome of the bacterial host cell by homologous recombination. Hence. The DNA sequence to be integrated is flanked by DNA sequences that are homologous to the 5' and 3' flanking sequences on the chromosome. It is understood in terms of the invention that gene integration can also combine gene integration and gene deletion in one step, i.e. a DNA sequence on the chromosome is replaced by the incoming DNA sequence for gene integration.

Homologous recombination can be achieved by two different methods known in the art: By two consecutive rounds of homologous recombination (Campbell recombination) with circular plasmid DNA, e.g. based on the well-known temperature sensitive plasmid pE194 (Nahrstedt et al., Strain development in *Bacillus licheniformis*: construction of biologically contained mutants deficient in sporulation and DNA repair. J Biotechnol. 2005 Sep. 29; 119(3):245-54).

The integration of the deletion plasmid containing an incoming DNA molecule comprising sequences that are homologous to the 5' and 3' flanking sequences of the target sequence on the chromosome is achieved by a first homologous recombination (Campbell recombination) with the first homologous region under selective conditions for the selectable marker and cultivation at the non-permissive temperature, i.e. that blocks plasmid replication. The second homologous recombination with the second homologous region is achieved by removal of selective pressure and cultivation at the permissive temperature, i.e. plasmid replication takes place, resulting in excision of the plasmid from the chromosome.

Alternatively, a non-replicative 'suicide' plasmid can be used forcing the integration by selection on the selectable marker. Only cells that have integrated the plasmid into the genome by homologous recombination are able to grow under the selective conditions. Plasmid removal/excision from the chromosome is achieved with a second homologous recombination which is forced by the activation of a counterselection marker present on the plasmid.

The second method of homologous recombination refers to two homologous recombination events simultaneously taking place, also known as 'double crossing over' or 'double homologous recombination. The incoming DNA sequence is linear and can be obtained by PCR, linearization of plasmid DNA or preparation of chromosomal DNA which inevitable results in fragmented linear DNA. WO0308125 uses linear DNA constructs (either linearized plasmids or PCR fragments) comprising a selectable marker flanked by the 5' and 3' homologous regions which are used for genomic integration via double crossing over homologous recombination. It is well understood that next to the selectable marker additional DNA, such as gene expression cassettes, when flanked by said homologous region are integrated into the chromosome of the bacterial host cell.

Homologous recombination requires DNA sequences homologous to the 5' and 3' flanking sequences of the target sequence on the chromosome of the host cell of sufficient size, hence should contain a sufficient number of nucleic acid such as 100 to 1,500 base pairs, preferably 400 to 1,500 base pairs, and most preferably 800 to 1,500 base pairs, which have a high degree of identity to the corresponding target sequence to enhance the probability of homologous recombination (Dubnau, 1993, Genetic exchange and homologous recombination. In *Bacillus subtilis* and Other Gram-positive Bacteria, p. 555-584. Edited by A. I. Sonenshein, J. A. Hoch & R. Losick, Washington DC, American Society for Microbiology; Michel and Ehrlich, 1984, The EMBO Journal, vol. 3, pp. 2879-2884).

Gene inactivation by deletion/insertion/substitution can also be achieved by CRISPR/Cas9 genome editing technologies where the CRISPR cutting properties could be used to disrupt genes in almost any organism's genome with unprecedented ease (Mali P, et al (2013) Science. 339(6121):819-823; Cong L, et al (2013) Science 339(6121)). Recently it became clear that providing a template for repair, e.g. homologous regions, allowed for editing the genome with nearly any desired sequence at nearly any site, transforming CRISPR into a powerful gene editing tool (WO/2014/150624, WO/2014/204728).

CRISPR-based expression systems for application in gram positive organisms such as *Bacillus* species based on the single-plasmid system approach, i.e. comprising the Cas9 endonuclease, the gRNA (e.g. sgRNA or crRNA/tracrRNA), repair homology sequences (donor DNA) on one single *E. coli-Bacillus* shuttle vector have been successfully applied (Altenbuchner, (2016): Applied and environmental microbiology 82 (17), 5421-5427; Zhou, et al. (2019): International journal of biological macromolecules 122, 329-337).

Alternatively to "directed" methods of inactivation it is understood in the scope of the invention that whole-cell mutagenesis by applying mutagenizing conditions such as exposure of the cells to UV radiation, or chemical mutagenizing chemicals such as NTG (N-methyl-N'-nitro-N-nitrosoguanidine), EMS (ethyl-methane-sulfonate), in combination with screening and/—or selection of the desired property, e.g. reduced lipase/esterase activity is a well-known approach to achieve functional inactivation.

The introduction of DNA into a host cell, in one embodiment a *Bacillus* cell, may, for instance, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278). Specific transformation protocols are known in the art for various types of host cells (see, e.g., for *E. coli* protoplast transformation see Hanahan, 1983, J. Mol. Biol. 166: 557-580).

In a preferred embodiment, the *Bacillus* cell comprises a non-native complete or partial deletion of the gene coding for the YitV and/or YpmR protein or the *Bacillus* cell comprises a non-native complete or partial deletion of the promoter region of the gene coding for the YitV and/or YpmR protein resulting in the non-native reduction of the YitV and/or YpmR protein expression. Preferably, the *Bacillus* cell comprises a non-native complete deletion of the gene coding for the YitV and/or YpmR protein or the *Bacillus* cell comprises a non-native complete deletion of the promoter region of the gene coding for the YitV and/or YpmR protein resulting in the non-native reduction of the YitV and/or YpmR protein expression.

Preferably the *Bacillus* cell comprises a full or partial deletion of or one or more point mutations in the yitV and/or ypmR gene resulting in a reduced expression of the YitV and/or YpmR protein. Preferably, the inactivated yitV gene comprises a nucleotide sequence having at least 70%, at least 75%, at least 80%, at least 85%, at least 90%, at least 92%, at least 95%, at least 96%, at least 97%, at least 98%, at least 99%, or even 100% identity with SEQ ID NO: 32.

Preferably, the inactivated ypmR gene comprises a nucleotide sequence having at least 70%, at least 75%, at least 80%, at least 85%, at least 90%, at least 92%, at least 95%, at least 96%, at least 97%, at least 98%, at least 99%, or even 100% identity with SEQ ID NO: 40.

Preferably, the expression of the YitV protein is reduced by an inactivation of the yitV gene, wherein the yitV gene comprises a nucleotide sequence having at least 80%, at least 85%, at least 90%, at least 92%, at least 95%, at least 96%, at least 97%, at least 98%, at least 99%, or even 100% identity with SEQ ID NO: 32.

Preferably, the expression of the YpmR protein is reduced by an inactivation of the ypmR gene, wherein the ypmR gene comprises a nucleotide sequence having at least 80%, at least 85%, at least 90%, at least 92%, at least 95%, at least 96%, at least 97%, at least 98%, at least 99%, or even 100% identity with SEQ ID NO: 40.

However, also other genes coding for enzymes with lipase and/or esterase activity could be reduced in their expression in the *Bacillus* cell, preferably in addition to the yitV and/or ypmR gene. For instance, one or more of the proteins shown in Table 1 can be reduced in its expression, preferably by full or partial deletion of or by point mutations in one or more genes comprising a polynucleotide having at least 70%%, at least 75%, at least 80%, at least 85%, at least 90%, at least 92%, at least 95%, at least 96%, at least 97%, at least 98%, at least 99%, or even 100% identity with SEQ ID NO: 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60.

*Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus Bacillus paralicheniformis, Bacillus subtilis*, and *Bacillus thuringiensis* cells. In one embodiment, the bacterial host cell is a *Bacillus amyloliquefaciens, Bacillus lentus, Bacillus licheniformis, Bacillus pumilus, Bacillus stearothermophilus* or *Bacillus subtilis* cell. In another embodiment, the bacterial host cell is a *Bacillus licheniformis* cell or a *Bacillus subtilis* cell, in a specifically preferred embodiment a *Bacillus licheniformis* cell. In one embodiment, the *Bacillus* cell is not a *Bacillus subtilis* cell.

For industrial fermentation processes, the bacterial host cell may be genetically modified to meet the needs of highest product purity and regulatory requirements. It is therefore in scope of the invention to use *Bacillus* production hosts that may additionally contain modifications, e.g., deletions or disruptions, of other genes that may be detrimental to the production, recovery or application of a polypeptide of interest. In one embodiment, a bacterial host cell is a protease-deficient cell. The bacterial host cell, e.g., *Bacillus* cell, preferably comprises a disruption or deletion of extracellular protease genes including but not limited to aprE, mpr, vpr, bpr, and/or epr. Further preferably the bacterial host cell does not produce spores. Further preferably the bacterial host cell, e.g., a *Bacillus* cell, comprises a disruption or deletion of spol/AC, sigE, and/or sigG. Further, preferably the bacterial host cell, e.g., *Bacillus* cell, comprises a disruption or deletion of one of the genes involved in the biosynthesis of surfactin, e.g., srfA, srfB, srfC, and/or srfD, see, for example, U.S. Pat. No. 5,958,728. It is also preferred that the bacterial host cell comprises a disruption or deletion of one of the genes involved in the biosynthesis of polyglutamic acid. Other genes, including but not limited to the amyE gene, which are detrimental to the production, recovery or application of a polypeptide of interest may also be disrupted or deleted.

In one embodiment, the *Bacillus* cell comprises a selectable marker. The selectable marker can be antibiotic resistance markers such as ampicillin, kanamycin, erythromycin, chloramphenicol or tetracycline, or an auxotrophic resistance marker.

Optionally the *Bacillus* cell might comprise a counterselection markers as described herein. In a preferred embodiment, the counterselection polypeptide is a polypeptide which involved in the pyrimidine metabolism. Thus, the counterselection polypeptide, such as oroP, pyrE, pyrF, upp, uses flourated analogons of intermediates in the pyrmidine metabolism, such as, 5-fluoro-orotate or 5-fluoro-uridine. Alternatively, toxins of toxin-anti-toxin systems (TA) such as the mazEF, ccdAB could be used as functional counterselection polypeptides in *Bacillus* (see Dong, H., Zhang, D. Current development in genetic engineering strategies of *Bacillus* species. Microb Cell Fact 13, 63 (2014)). In an even more preferred embodiment, the couterselection polypeptide is a cytosine deaminase, such as provided by the codBA system (Kostner D, Rachinger M, Liebl W, Ehrenreich A. Markerless deletion of putative alanine dehydrogenase genes in *Bacillus licheniformis* using a codBA-based counterselection technique. Microbiology. 2017; 163(11):1532-1539). Preferably, the counterselection agent is 5-fluorocytosine.

The *Bacillus* cell of the present invention preferably produces a compound of interest, preferably a protein, as described herein. Preferably, the *Bacillus* cell comprises a gene encoding for a protein of interest, preferably a heterologous protein of interest. Preferably the *Bacillus* cell is a *Bacillus licheniformis* cell.

Methods of the Invention

The present invention is also directed to various methods using the improved *Bacillus* cell of the present invention as described herein.

Production of a Compound of Interest

The recombinant *Bacillus* cells created by the methods described herein are particularly useful as host cells for the production of a compound of interest. Therefore, the present invention is also directed to a method of cultivating a recombinant *Bacillus* cells obtained by any of the methods described herein. In a particular embodiment, the present invention is further directed to methods of producing a compound of interest comprising: (a) cultivating the recombinant cell under conditions conducive for production of the compound of interest; and (b) optionally recovering the compound of interest from the fermentation broth.

The compound of interest may or may not be further purified from the fermentation broth. Thus, in one embodiment, the present invention refers to a fermentation broth comprising a compound of interest obtained by a fermentation process as described herein.

In one embodiment, the present invention is directed to a method of producing a compound of interest comprising the steps of a) cultivating a *Bacillus* cell in the fermentation medium described herein for a time and under conditions suitable for the *Bacillus* cell to produce the compound of interest; and
b) optionally, purifying the compound of interest from the fermentation broth.

The compound of interest can be produced by a *Bacillus* cell expressing one or more polynucleotides native or heterologous to the cell. Preferably the one or more polynucleotides native or heterologous to the cell codes for a protein of interest.

Thus, preferred is a method for producing a compound of interest, preferably a polypeptide of interest, comprising the steps of a) providing a modified *Bacillus* host cell comprising an inactivation of the yitV and/or ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Particularly preferred is a method for producing a compound of interest, preferably a polypeptide of interest, preferably an enzyme, comprising the steps of a) providing a modified *Bacillus* host cell comprising an inactivation of the yitV and ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

In a particular embodiment, the present invention is further directed to methods of producing a native or foreign polypeptide comprising: (a) cultivating the recombinant cell under conditions conducive for production of the polypeptide; and (b) optionally recovering the polypeptide.

Thus, preferred is a method for producing a polypeptide of interest, preferably an enzyme, comprising the steps of a) providing a modified *Bacillus* host cell comprising an inactivation of the yitV and/or ypmR gene, preferably an inactivation of the yitV and the ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Thus, the present invention is also directed to a method for producing a heterologous protein of interest in a bacterial cell comprising the step of cultivating the bacterial host cell obtained by any of the methods described herein for a time and under conditions sufficient to produce the heterologous protein. The bacterial host cells are cultivated in a nutrient medium suitable for production of a polypeptide of interest using methods known in the art. For example, the cell may be cultivated by shake flask cultivation, small-scale or largescale fermentation (including continuous, batch, fed-batch, or solid state fermentations) in laboratory or industrial fermenters performed in a suitable medium and under conditions allowing the polypeptide of interest to be expressed and/or isolated. In one embodiment, the cultivation of the bacterial host cell is by fermentation in industrial scale, e.g. WO2020169563A1 The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The protein of interest can accumulate in the cell or can be secreted outside of the cell. The secreted polypeptide of interest can be recovered directly from the medium. The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), Enzyme Handbook, Springer-Verlag, New York, 1990).

The resulting protein of interest may be isolated by methods known in the art. For example, a protein of interest may be isolated from the fermentation broth by conventional procedures including, but not limited to, centrifugation, filtration, extraction, spray-drying, evaporation, or precipitation. Depending on the expression construct used, the protein of interest can be secreted into the fermentation broth or can remain inside the host cell. In case of the latter, the protein of interest can be recovered from the fermentation broth by applying a step where the cells are lysed. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). The purified polypeptide may then be concentrated by procedures known in the art including, but not limited to, ultrafiltration and evaporation, in particular, thin film evaporation. In another embodiment, the protein of interest is not purified from the fermentation broth. In a specific embodiment, the protein of interest is not secreted in the fermentation broth and not recovered from the fermentation broth.

Compound of Interest, Preferably Protein of Interest

The host cell of the present invention shall further comprise an expression cassette for the production of a compound of interest, preferably a protein of interest.

Compounds of interest maybe polymers, preferably hyaluronic acidy, preferably as described in (WO2005098016), or polyglutamic acid, preferably as described in EP2196534, or maybe vitamins, preferably vitamin B5, preferably as described in WO2010018169, or riboflavin, preferably as described in WO2017036903, or may be polypeptides, preferably enzymes.

Preferably, the compound of interest, preferably protein of interest, may be secreted by the *Bacillus* host cell or may be produced intracellularly.

In one embodiment, the compound of interest is a protein of interest. Preferably, the protein of interest is encoded by a gene introduced into the *Bacillus* cell by means of recombinant DNA technology. Preferably, the protein of interest is heterologous to the *Bacillus* cell. Preferably, the protein of interest is an enzyme. The enzyme may be, but is not limited to, a detergent enzyme and an enzyme suitable for human and/or animal nutrition. In one preferred embodiment, the enzyme is an enzyme suitable for the use in human nutrition. In one embodiment, the enzyme is classified as an oxidoreductase (EC 1), a transferase (EC 2), a hydrolase (EC 3), a lyase (EC 4), an isomerase (EC 5), or a Ligase (EC 6) (EC-numbering according to Enzyme Nomenclature, Recommendations (1992) of the Nomenclature Committee of the International Union of Biochemistry and Molecular Biology including its supplements published 1993-1999). In one embodiment, the protein of interest is a protein conferring resistance to antibiotics to a host cell.

In another embodiment, the enzyme is a hydrolase (EC 3), in one embodiment a glycosidase (EC 3.2) or a peptidase (EC 3.4). In one embodiment, enzymes selected from the group consisting of an amylase (in particular an alpha-amylase (EC 3.2.1.1)), a cellulase (EC 3.2.1.4), a lactase (EC 3.2.1.108), a mannanase (EC 3.2.1.25), a lipase (EC3.1.1.3), a phytase (EC 3.1.3.8), a nuclease (EC 3.1.11 to EC 3.1.31), and a protease. In one embodiment, the enzyme is selected from the group consisting of oxidoreductase, transferase, hydrolase, lyase, isomerase, ligase, aminopeptidase, amylase, asparaginase, carbohydrase, carboxypeptidase, catalase, cellulase, chitinase, cutinase, cyclodextrin glycosyltransferase, deoxyribonuclease, esterase, alpha-galactosidase, betagalactosidase, glucoamylase, alpha-glucosidase, beta-glucosidase, hyaluronic acid synthase, invertase, laccase, lipase, mannosidase, mutanase, oxidase, a pectinolytic enzyme, peroxidase, phytase, polyphenoloxidase, protease, ribonuclease, transglutaminase, and orxylanase. In particular an enzyme selected from the group consisting of amylase, protease, mannanase, lactase, and cellulase, preferably protease, amylase, lactase and mannanse, in a specific embodiment amylase or protease, in one embodiment, a serine protease (EC 3.4.21). In another embodiment the enzyme is a subtilisin protease.

For producing a protein of interest, the *Bacillus* cell can comprise an expression construct comprising one or more control sequences required for expression of the polynucleotide. Such control sequences include, but are not limited to, promoter sequence, 5'-UTR (also called leader sequence), ribosomal binding site (RBS, shine dalgarno sequence), 3'-UTR, and transcription start and stop sites. In one embodiment, the control sequences may be provided with linkers for the purpose of introducing specific restriction sites facilitating ligation of the control sequences with the polynucleotide to be expressed. The expression of the protein of interest maybe plasmid-based expression or the gene coding for the protein of interest may be integrated into the genome of the *Bacillus* cell.

The nucleic acid construct comprises a suitable transcription start and terminator sequence. Any transcription start or terminator that is functional in the host cell of choice may be used in the present invention.

In one embodiment the nucleic acid construct comprises a suitable UTR (untranslated region) sequence. In one embodiment, the nucleic acid construct described herein comprises a 5'UTR and/or a 3'UTR sequence. In one embodiment, the one or more control sequence of the nucleic acid construct comprises a 5'UTR, also referred to as leader sequence. In another one embodiment, the one or more control sequence of the nucleic acid construct comprises a 5'UTR sequence comprising a ribosome-binding site also referred to as a shine-dalgarno sequence. Any leader sequence that is functional in the host cell of choice may be used in the present invention. The UTR can be natural or artificial.

In a preferred embodiment, the replication of a plasmid shall be independent of the replication of the chromosome of the bacterial host cell. For autonomous replication, the expression vector may further comprise an origin of replication enabling the vector to replicate autonomously in the host cell in question. Bacterial origins of replication include but are not limited to the origins of replication of plasmids pBR322, pUC19, pSC101, pACYC177, and pACYC184 permitting replication in *E. coli* (Sambrook, J. and Russell, D. W. Molecular cloning. A laboratory manual, 3rd ed, Cold Spring Harbor Laboratory Press, Cold Spring Harbor, N Y. 2001; Cohen, S. N., Chang, A. C. Y., Boyer, H. W., & Helling, R. B. (1973). Construction of Biologically Functional Bacterial Plasmids In Vitro. Proceedings of the National Academy of Sciences of the United States of America, 70(11), 3240-3244), and pUB110, pC194, pE194, pTB19, pAMβ1, and pTA1060 permitting replication in *Bacillus* (Janniere, L., Bruand, C., and Ehrlich, S. D. (1990). Structurally stable *Bacillus subtilis* cloning vectors. Gene 87, 53-6; Ehrlich, S. D., Bruand, C., Sozhamannan, S., Dabert, P., Gros, M. F., Janniere, L., and Gruss, A. (1991). Plasmid replication and structural stability in *Bacillus subtilis*. Res. Microbiol. 142, 869-873), and pE194 (Dempsey, L. A. and Dubnau, D. A. (1989). Localization of the replication origin of plasmid pE194. J. Bacteriol. 171, 2866-2869). The origin of replication may be one having a mutation to make its function temperature-sensitive in the host cell (see, e.g., Ehrlich, 1978, Proceedings of the National Academy of Sciences USA 75:1433-1436).

The copy number of a plasmid is defined as the average number of plasmids per bacterial cell or per chromosome under normal growth conditions. Moreover, there are different types of replication origins that result in different copy numbers in the bacterial host. The plasmid replicon pBS72 (accession number AY102630.1) and the plasmids pTB19 and derivatives pTB51, pTB52 confer low copy number with 6 copies and 1 to 8 copies, respectively, within *Bacillus* cells whereas plasmids pE194 (accession number V01278.1) and pUB110 (accession number M19465.1)/pBC16 (accession number U32369.1) confer low-medium copy number with 14-20 and medium copy number with 30-50 copies per cell, respectively. Plasmid pE194 was analyzed in more detail (Villafane, et al (1987): J. Bacteriol. 169(10), 4822-4829) and several pE194—cop mutants described having high copy numbers within *Bacillus* ranging from 85 copies to 202 copies. Moreover, plasmid pE194 is temperature sensitive with stable copy number up to 37° C., however abolished replication above 43° C. In addition, it exists a pE194 variant referred to as pE194ts with two point mutations within the cop-repF region (nt 1235 ad nt 1431) leading to a more drastic temperature sensitivity—stable copy number up to 32° C., however only 1 to 2 copies per cell at 37° C.

In one embodiment, the vectors contain one or more selectable markers that permit easy selection of transformed cells. A selectable marker is a gene encoding a product, which provides for biocide resistance, resistance to heavy metals, prototrophy to auxotrophs, and the like. Bacterial selectable markers include but are not limited to the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO91/09129, where the selectable marker is on a separate vector.

A promoter for expressing the protein of interest or the selectable marker can be an "inducer-dependent promoter" or an "inducer-independent promoter" comprising constitutive promoters or promoters which are under the control of other cellular regulating factors.

The person skilled in the art is capable to select suitable promoters for expressing the third alanine racemase and the polypeptide of interest. For example, the polynucleotide encoding the polypeptide of interest is, preferably, operably linked to an "inducer-dependent promoter" or an "inducer-independent promoter". Further, the polynucleotide encoding the third alanine racemase is, preferably, operably linked to an "inducer-independent promoter", such as a constitutive promoter.

An "inducer dependent promoter" is understood herein as a promoter that is increased in its activity to enable transcription of the gene to which the promoter is operably linked upon addition of an "inducer molecule" to the fermentation medium. Thus, for an inducer-dependent promoter, the presence of the inducer molecule triggers via signal transduction an increase in expression of the gene operably linked to the promoter. The gene expression prior activation by the presence of the inducer molecule does not need to be absent, but can also be present at a low level of basal gene expression that is increased after addition of the inducer molecule. The "inducer molecule" is a molecule which presence in the fermentation medium is capable of affecting an increase in expression of a gene by increasing the activity of an inducer-dependent promoter operably linked to the gene. Preferably, the inducer molecule is a carbohydrate or an analog thereof. In one embodiment, the inducer molecule is a secondary carbon source of the *Bacillus* cell. In the presence of a mixture of carbohydrates cells selectively take up the carbon source that provide them with the most energy and growth advantage (primary carbon source). Simultaneously, they repress the various functions involved in the catabolism and uptake of the less preferred carbon sources (secondary carbon source). Typically, a primary carbon source for *Bacillus* is glucose and various other sugars and sugar derivates being used by *Bacillus* as secondary carbon sources. Secondary carbon sources include e.g. mannose or lactose without being restricted to these.

Examples of inducer dependent promoters are given in the table below by reference to the respective operon:

| Operon | Regulator a) | Type b) | Inducer | Organism |
|---|---|---|---|---|
| sacPA | SacT | AT | sucrose | *B. subtilis* |
| sacB | SacY | AT | sucrose | *B. subtilis* |
| bgl PH | LicT | AT | β-glucosides | *B. subtilis* |
| licBCAH | LicR | A | oligo-β-glucosides | *B. subtilis* |
| levDEFG sacL | LevR | A | fructose | *B. subtilis* |
| mtlAD | MtlR | A | mannitol | *B. subtilis* |
| manPA-yjdF | ManR | A | mannose | *B. subtilis* |
| manR | ManR | A | mannose | *B. subtilis* |
| bglFB bglG | BglG | AT | β-glucosides | *E. coli* |
| lacTEGF | LacT | AT | lactose | *L. casei* |
| lacZYA | lacl | R | Allolactose; IPTG (Isopropyl β-D-1-thiogalactopyranoside) | *E. coli* |
| araBAD | araC | AR | L-arabinose | *E. coli* |
| xylAB | XylR | R | Xylose | *B. subtilis* |

a: transcriptional regulator protein
b: A: activator
AT: antiterminator
R: repressor
AR: activator/repressor In contrast thereto, the activity of promoters that do not depend on the presence of an inducer molecule (herein called 'inducer-independent promoters') are either constitutively active or can be increased regardless of the presence of an inducer molecule that is added to the fermentation medium.

Constitutive promoters are independent of other cellular regulating factors and transcription initiation is dependent on sigma factor A (sigA). The sigA-dependent promoters comprise the sigma factor A specific recognition sites '-35'-region and '-10'-region.

Preferably, the 'inducer-independent promoter' sequence is selected from the group consisting of constitutive promoters not limited to promoters Pveg, PlepA, PserA, PymdA, Pfba and derivatives thereof with different strength of gene expression (Guiziou et al, (2016): Nucleic Acids Res. 44(15), 7495-7508), the aprE promoter, the bacteriophage SPO1 promoters P4, P5, P15 (WO15118126), the cryIIIA promoter from *Bacillus thuringiensis* (WO9425612), the amyQ promoter from *Bacillus amyloliquefaciens*, the amyL promoter and promoter variants from *Bacillus licheniformis* (U.S. Pat. No. 5,698,415) and combinations thereof, or active fragments or variants thereof, preferably an aprE promoter sequence.

Further optionally the expression construct comprises a 5'UTR. This is a transcribed but not translated region downstream of the −1 promoter position. Such untranslated region for example should contain a ribosome binding site to facilitate translation in those cases where the target gene codes for a peptide or polypeptide.

With respect to the 5'UTR the invention in particular teaches to combine the promoter of the present invention with a 5UTR comprising one or more stabilising elements. This way the mRNAs synthesized from the promoter region may be processed to generate mRNA transcript with a stabilizer sequence at the 5' end of the transcript. Preferably such a stabilizer sequence at the Send of the mRNA transcripts increases their half-life as described by Hue et al, 1995, Journal of Bacteriology 177: 3465-3471. Suitable mRNA stabilizing elements are those described in WO08148575, preferably SEQ ID NO. 1 to 5 of WO08140615, or fragments of these sequences which maintain the mRNA stabilizing function, and in WO08140615, preferably *Bacillus thuringiensis* CryIIIA mRNA stabilising sequence or bacteriophage SP82 mRNA stabilising sequence, more preferably a mRNA stabilising sequence according to SEQ ID NO. 4 or 5 of WO08140615, more preferably a modified mRNA stabilising sequence according to SEQ ID NO. 6 of WO08140615, or fragments of these sequences which maintain the mRNA stabilizing function.

Preferred mRNA stabilizing elements are selected from the group consisting of aprE, grpE, cotG, SP82, RSBgsiB, CryIIIA mRNA stabilizing elements, or according to fragments of these sequences which maintain the mRNA stabilizing function. A preferred mRNA stabilizing element is the grpE mRNA stabilizing element (corresponding to SEQ ID NO. 2 of WO08148575).

The 5UTR also preferably comprises a modified rib leader sequence located downstream of the promoter and upstream of an ribosome binding site (RBS). In the context of the present invention a rib leader is herewith defined as the leader sequence upstream of the riboflavin biosynthetic genes (rib operon) in a *Bacillus* cell, more preferably in a *Bacillus subtilis* cell. In *Bacillus subtilis*, the rib operon, comprising the genes involved in riboflavin biosynthesis, include ribG (ribD), ribB (ribE), ribA, and ribH genes. Transcription of the riboflavin operon from the rib promoter (Prib) in *B. subtilis* is controlled by a riboswitch involving an untranslated regulatory leader region (the rib leader) of almost 300 nucleotides located in the 5-region of the rib operon between the transcription start and the translation start codon of the first gene in the operon, ribG. Suitable rib leader sequences are described in WO2015/1181296, in particular pages 23-25, incorporated herein by reference.

In a preferred embodiment, the present invention is directed to a method of producing a protein of interest comprising the steps of a) cultivating a *Bacillus licheniformis* cell comprising a reduced expression of the YitV and/or YpmR protein in the fermentation medium described herein for a time and under conditions suitable for the *Bacillus* cell to produce the protein of interest; and
b) optionally, purifying the protein of interest from the fermentation broth.

In a preferred embodiment, the present invention is directed to a method of producing a protein of interest comprising the steps of
a) cultivating a *Bacillus licheniformis* cell comprising a deletion of the yitV and/or ypmR gene in the fermentation medium described herein for a time and under conditions suitable for the *Bacillus* cell to produce the protein of interest; and
b) optionally, purifying the protein of interest from the fermentation broth.

In a particularly preferred embodiment, the present invention is directed to a method of producing an enzyme comprising the steps of
a) cultivating a *Bacillus licheniformis* cell comprising a deletion of the yitV and of the ypmR gene in the fermentation medium described herein for a time and under conditions suitable for the *Bacillus* cell to produce the enzyme; and
b) optionally, purifying the enzyme from the fermentation broth.

Method for Reducing the Formation of Malodour or Off-Flavour

In another embodiment, the present invention is directed to a method for reducing the formation of malodour or off-flavour in a composition comprising a compound of interest obtained by fermentation of a *Bacillus* cell comprising the fermentation of a *Bacillus* cell as described herein capable of producing a compound of interest, purifying the compound of interest from the fermentation broth and providing a composition comprising the purified compound of interest.

In a preferred embodiment, the present invention is directed to a method for reducing the formation of malodour or off-flavour in a composition comprising a compound of interest obtained by fermentation of a *Bacillus* cell comprising the steps of
a) cultivating a *Bacillus* cell comprising reduced expression of the YitV and/or YpmR protein in a fermentation medium described herein for a time and under conditions suitable for the *Bacillus* cell to produce the protein of interest; and
b) purifying the protein of interest from the fermentation broth;
c) providing a composition comprising the protein of interest of step (b).

In a preferred embodiment, the present invention is directed to a method for reducing the formation of malodour or off-flavour in a composition comprising a compound of interest obtained by fermentation of a *Bacillus licheniformis* cell comprising the steps of
a) cultivating a *Bacillus licheniformis* cell comprising reduced expression of the YitV and/or YpmR protein in a fermentation medium described herein for a time and under conditions suitable for the *Bacillus* cell to produce the protein of interest; and
b) purifying the protein of interest from the fermentation broth;
c) providing a composition comprising the protein of interest of step (b).

A further embodiment of the invention is a method for reducing the lipase and/or esterase activity in a *Bacillus* cell comprising the inactivation of the yitV and/or ypmR gene in the *Bacillus* cell, preferably the inactivation of the yitV and ypmR gene in the *Bacillus* cell, preferably in a *Bacillus licheniformis* cell.

An additional embodiment of the present invention is a method for reducing the lipase and/or esterase activity of a compound of interest, preferably a protein of interest, preferably an enzyme, produced by a *Bacillus* cell comprising the steps of
a) providing a modified *Bacillus* host cell comprising an inactivation of the yitV and/or ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

An further embodiment of the present invention is a method for reducing the formation of malodour or off-flavor in a composition comprising a compound of interest, preferably a polypeptide of interest, preferably an enzyme, produced by a *Bacillus* cell, preferably a *Bacillus licheniformis* cell, comprising the steps of
a) providing a modified *Bacillus* host cell comprising an inactivation of the yitV and/or ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Preferred is a method for reducing the formation of malodour or off-flavor in a composition comprising a compound of interest, preferably a polypeptide of interest, preferably an enzyme, produced by a *Bacillus* cell, preferably *Bacillus licheniformis* cell, comprising the steps of
a) providing a modified *Bacillus* host cell comprising an inactivation of the yitV and ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Composition Comprising the Compound of Interest

In another embodiment, the present invention is directed to a composition comprising the purified compound of interest, preferably a protein of interest, obtained from a fermentation broth of the *Bacillus* cells comprising a reduced expression no of the YitV and/or YpmR protein. Compared to a composition obtained with a compound of interest obtained from a fermentation broth of *Bacillus* cells not according to the invention, the composition comprises a reduced level of YitV and/or YpmR protein, preferably a reduced level of YitV and YpmR protein.

In a preferred embodiment, the composition comprising the compound of interest obtained is obtained by a method comprising the steps of
a) cultivating a *Bacillus* cell comprising reduced expression of the YitV and/or YpmR protein as described herein in a fermentation medium for a time and under conditions suitable for the *Bacillus* cell to produce the protein of interest; and
b) purifying the protein of interest from the fermentation broth;
c) providing a composition comprising the protein of interest of step (b).

In a preferred embodiment, the composition comprising the compound of interest obtained is obtained by a method comprising the steps of
a) cultivating a *Bacillus licheniformis* cell comprising reduced expression of the YitV and/or YpmR protein as described herein in a fermentation medium for a time and under conditions suitable for the *Bacillus* cell to produce the protein of interest; and
b) purifying the protein of interest from the fermentation broth;
c) providing a composition comprising the protein of interest of step (b).

Preferred is a composition comprising a compound of interest, preferably a protein of interest, preferably an enzyme, with reduced contamination with lipase and/or esterase activity obtained by a method comprising the steps of
a) providing a modified *Bacillus* host cell comprising an inactivation of the yitV and/or ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Particularly preferred is a composition comprising a compound of interest, preferably a protein of interest, with reduced contamination with lipase and/or esterase activity obtained by a method comprising the steps of
a) providing a modified *Bacillus* host cell comprising an inactivation of the yitV and ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Further preferred is a composition comprising a compound of interest, preferably a protein of interest, with reduced contamination with YitV and/or YpmR protein obtained by a method comprising the steps of
a) providing a modified *Bacillus* host cell comprising an inactivation of the yitV and/or ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Further preferred is a composition comprising a compound of interest, preferably a protein of interest, with reduced contamination with YitV and YpmR protein obtained by a method comprising the steps of
a) providing a modified *Bacillus* host cell comprising an inactivation of the yitV and ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

Particularly preferred is a composition comprising a protein of interest, preferably an enzyme, with reduced contamination with YitV and YpmR protein obtained by a method comprising the steps of
a) providing a modified *Bacillus* host cell, preferably a *Bacillus licheniformis* host cell, comprising an inactivation of the yitV and ypmR gene,
b) introducing into said modified *Bacillus* host cell an expression cassette for a compound of interest, preferably a polypeptide of interest,
c) cultivating the host cell under conditions which allow for the expression of the compound of interest, and
d) optionally isolating the compound of interest from the cultivation medium.

In one embodiment, the composition comprising the compound of interest is for laundry detergents, dish washing detergents, and cleaning products for homes, industry, vehicle care, baking, human or animal feed, pulp and paper processing, starch processing, and ethanol production. In a preferred embodiment the comprising the compound of interest is a detergent composition comprising one or more detergents. In a further preferred embodiment, the composition comprising the compound of interest is a food or feed composition, preferably a dairy composition.

EXAMPLES

The following examples only serve to illustrate the invention. The numerous possible variations that are obvious to a person skilled in the art also fall within the scope of the invention.

Unless otherwise stated the following experiments have been performed by applying standard equipment, methods, chemicals, and biochemicals as used in genetic engineering and fermentative production of chemical compounds by cultivation of microorganisms. See also Sambrook et al. (Sambrook, J. and Russell, D. W. Molecular cloning. A laboratory manual, 3rd ed, Cold Spring Harbor Laboratory Press, Cold Spring Harbor, N Y. 2001) and Chmiel et al. (Bioprocesstechnik 1. Einführung in die Bioverfahrenstechnik, Gustav Fischer Verlag, Stuttgart, 1991).

Electrocompetent *Bacillus licheniformis* Cells and Electroporation

Transformation of DNA into a *Bacillus licheniformis* strain as described in U.S. Pat. No. 5,352,604 is performed via electroporation. Preparation of electrocompetent *Bacillus licheniformis* cells and transformation of DNA is performed as essentially described by Brigidi et al (Brigidi, P., Mateuzzi, D. (1991). Biotechnol. Techniques 5, 5) with the following modification: Upon transformation of DNA, cells are recovered in 1 ml LBSPG buffer and incubated for 60 min at 37° C. (Vehmaanpers J., 1989, FEMS Microbio. Lett., 61: 165-170) following plating on selective LB-agar plates.

In order to overcome the *Bacillus licheniformis* specific restriction modification system of *Bacillus licheniformis* strains, plasmid DNA is isolated from Ec #098 cells as described below.

Plasmid Isolation

Plasmid DNA was isolated from *Bacillus* and *E. coli* cells by standard molecular biology methods described in (Sambrook, J. and Russell, D. W. Molecular cloning. A laboratory manual, 3rd ed, Cold Spring Harbor Laboratory Press, Cold Spring Harbor, N Y. 2001) or the alkaline lysis method (Birnboim, H. C., Doly, J. (1979). Nucleic Acids Res 7(6): 1513-1523). *Bacillus* cells were in comparison to *E. coli* treated with 10 mg/ml lysozyme for 30 min at 37 C prior to cell lysis.

Molecular Biology Methods and Techniques

Standard methods in molecular biology not limited to cultivation of *Bacillus* and *E. coli* microorganisms, electroporation of DNA, isolation of genomic and plasmid DNA, PCR reactions, cloning technologies were performed as essentially described by Sambrook and Russell. (Sambrook, J. and Russell, D. W. Molecular cloning. A laboratory manual, 3rd ed, Cold Spring Harbor Laboratory Press, Cold Spring Harbor, N Y. 2001.)

Strains

*E. coli* Strain Ec #098

*E. coli* strain Ec #098 is an *E. coli* INV110 strain (Life technologies) carrying the DNA-methyltransferase encoding expression plasmid pMDS003 WO2019016051.

Generation of *Bacillus licheniformis* Gene k.o Strains

For gene deletion in a *Bacillus licheniformis* strain as described in U.S. Pat. No. 5,352,604 and derivatives thereof deletion plasmids were transformed into *E. coli* strain Ec #098 made competent according to the method of Chung (Chung, C. T., Niemela, S. L., and Miller, R. H. (1989). One-step preparation of competent *Escherichia coli*: transformation and storage of bacterial cells in the same solution. Proc. Natl. Acad. Sci. U.S.A 86, 2172-2175), following selection on LB-agar plates containing 100 μg/ml ampicillin and 30 μg/ml chloramphenicol at 37° C. Plasmid DNA was isolated from individual clones and analyzed for correctness by PCR analysis. The isolated plasmid DNA carries the DNA methylation pattern of *Bacillus licheniformis* as described in WO2019016051 and is protected from degradation upon transfer into *Bacillus licheniformis.* aprE Gene Deletion Strain Bli #002

Electrocompetent *Bacillus licheniformis* cells as described in U.S. Pat. No. 5,352,604 were prepared as described above and transformed with 1 μg of pDe1003 aprE gene deletion plasmid isolated from *E. coli* Ec #098 following plating on LB-agar plates containing 5 μg/ml erythromycin at 30° C.

The gene deletion procedure was performed as described in the following: Plasmid carrying *Bacillus licheniformis* cells were grown on LB-agar plates with 5 μg/ml erythromycin at 45° C. forcing integration of the deletion plasmid via Campbell recombination into the chromosome with one of the homology regions of pDe1003 homologous to the sequences 5' or 3' of the aprE gene. Clones were picked and cultivated in LB-media without selection pressure at 45° C. for 6 hours, following plating on LB-agar plates with 5 μg/ml erythromycin at 30° C. Individual clones were picked and analyzed by colony-PCR with oligonucleotides SEQ ID 066 and SEQ ID 067 for successful deletion of the aprE gene. Putative deletion positive individual clones were picked and taken through two consecutive overnight incubation in LB media without antibiotics at 45° C. to cure the plasmid and plated on LB-agar plates for overnight incubation at 30° C. Single clones were again restreaked on LB-agar plates with 5 μg/ml erythromycin and analyzed by colony PCR for successful deletion of the aprE gene. A single erythromycin-sensitive clone with the correct deleted aprE gene was isolated and designated Bli #002 amyB Gene Deletion Strain Bli #003

Electrocompetent *Bacillus licheniformis* Bli #002 cells were prepared as described above and transformed with 1 μg of pDe1004 amyB gene deletion plasmid isolated from *E. coli* Ec #098 following plating on LB-agar plates containing 5 μg/ml erythromycin at 30° C.

The gene deletion procedure was performed as described for the aprE gene.

The deletion of the amyB gene was analyzed by PCR with oligonucleotides SEQ ID 069 and SEQ ID 070. The resulting *Bacillus licheniformis* strain with a deleted aprE and deleted amyB gene is designated Bli #003.

sigF Gene Deletion Strain Bli #004

Electrocompetent *Bacillus licheniformis* Bli #003 cells were prepared as described above and transformed with 1 μg of pDel005 sigF gene deletion plasmid isolated from *E. coli* Ec #098 following plating on LB-agar plates containing 5 μg/ml erythromycin at 30° C.

The gene deletion procedure was performed as described for the aprE gene.

The deletion of the sigF gene was analyzed by PCR with oligonucleotides SEQ ID 071 and SEQ ID 072 The resulting *Bacillus licheniformis* strain with a deleted aprE, a deleted amyB gene and a deleted sigF gene is designated Bli #004. *Bacillus licheniformis* strain Bli #004 is no longer able to sporulate as described (Fleming et al., Appl Environ Microbiol. 1995 November; 61(11):3775-80).

Poly-Gamma Glutamate Synthesis Genes Deletion Strain Bli #008

Electrocompetent *Bacillus licheniformis* Bli #004 cells were prepared as described above and transformed with 1 μg of pDel007 pga gene deletion plasmid isolated from *E. coli* Ec #098 following plating on LB-agar plates containing 5 μg/ml erythromycin at 30° C.

The gene deletion procedure was performed as described for the deletion of the aprE gene.

The deletion of the pga genes was analyzed by PCR with oligonucleotides SEQ ID 075 and SEQ ID 076 The resulting *Bacillus licheniformis* strain with a deleted aprE, a deleted amyB gene, a deleted sigF gene and a deleted pga gene cluster is designated Bli #008.

Plasmids pEC194RS—*Bacillus* Temperature Sensitive Deletion Plasmid.

The plasmid pE194 (Villafane, et al (1987): J. Bacteriol. 169(10), 4822-4829) is PCR-amplified with oligonucleotides SEQ ID 061 and SEQ ID 062 with flanking PvuII sites, digested with restriction endonuclease PvuII and ligated into vector pCE1 digested with restriction enzyme SmaI. pCE1 is a pUC18 derivative, where the BsaI site within the ampicillin resistance gene has been removed by a silent mutation. The ligation mixture was transformed into *E. coli* DH10B cells (Life technologies). Transformants were spread and incubated overnight at 37 C on LB-agar plates containing 100 μg/ml ampicillin. Plasmid DNA was isolated from individual clones and analyzed for correctness by restriction digest. The resulting plasmid is named pEC194S.

The type-II-assembly mRFP cassette is PCR-amplified from plasmid pBSd141R (accession number: KY995200) (Radeck, J., Meyer, D., Lautenschlager, N., and Mascher, T. 2017. *Bacillus* SEVA siblings: A Golden Gate-based toolbox to create personalized integrative vectors for *Bacillus subtilis*. Sci. Rep. 7:14134) with oligonucleotides SEQ ID 063 and SEQ ID 064, comprising additional nucleotides for the restriction site BamHI. The PCR fragment and pEC194S were restricted with restriction enzyme BamHI following ligation and transformation into *E. coli* DH10B cells (Life technologies). Transformants were spread and incubated overnight at 37 C on LB-agar plates containing 100 μg/ml ampicillin. Plasmid DNA was isolated from individual clones and analyzed for correctness by restriction digest. The resulting plasmid pEC194RS carries the mRFP cassette with the open reading frame opposite to the reading frame of the erythromycin resistance gene.

pDel003—aprE Gene Deletion Plasmid

The gene deletion plasmid for the aprE gene of *Bacillus licheniformis* was constructed with plasmid pEC194RS and the gene synthesis construct SEQ ID 065 comprising the genomic regions 5' and 3' of the aprE gene flanked by BsaI sites compatible to pEC194RS. The type-II-assembly with restriction endonuclease BsaI was performed as described (Radeck et al., 2017) and the reaction mixture subsequently transformed into *E. coli* DH10B cells (Life technologies). Transformants were spread and incubated overnight at 37 C on LB-agar plates containing 100 μg/ml ampicillin. Plasmid DNA was isolated from individual clones and analyzed for correctness by restriction digest. The resulting aprE deletion plasmid is named pDel003.

pDel004—amyB Gene Deletion Plasmid

The gene deletion plasmid for the amyB gene of *Bacillus licheniformis* was constructed as described for pDel003, however the gene synthesis construct SEQ ID 068 comprising the genomic regions 5' and 3' of the amyB gene flanked by BsaI sites compatible to pEC194RS was used. The resulting amyB deletion plasmid is named pDel004.

pDel005—sigF Gene Deletion Plasmid

The gene deletion plasmid for the sigF gene (spoIIAC gene) of *Bacillus licheniformis* was constructed as described for pDel003, however the gene synthesis construct SEQ ID 070 comprising the genomic regions 5' and 3' of the sigF gene flanked by BsaI sites compatible to pEC194RS was used. The resulting sigF deletion plasmid is named pDel005.

pDel007—Poly-Gamma-Glutamate Synthesis Genes Deletion Plasmid

The deletion plasmid for deletion of the genes involved in poly-gamma-glutamate (pga) production, namely ywsC (pgsB), ywtA (pgsC), ywtB (pgsA), ywtC (pgsE) of *Bacillus licheniformis* was constructed as described for pDel003, however the gene synthesis construct SEQ ID 074 comprising the genomic regions 5' and 3' flanking the ywsC, ywtA (pgsC), ywtB (pgsA), ywtC (pgsE) genes flanked by BsaI sites compatible to pEC194RS was used. The resulting pga deletion plasmid is named pDel007.

Example 1: Sequence Based Identification of Genes Belonging to Enzymes with Putative Lipase/Esterase Activity Putative lipases/esterases were identified using hidden markov models (HMMs) from the Pfam database (version 33.1, https:dpfam.xfam.org/; Sara El-Gebali, Robert D Finn; The Pfam protein families database in 2019, Nucleic Acids Research, Volume 47, Issue D1, 8 Jan. 2019, Pages 0427-0432). The following HMMs were searched in the proteome of *Bacillus licheniformis* DSM13: PF00657.23, PF01674.19, PF01764.26, PF02230.17, PF03280.15, PF03583.15 PF13472.7, PF14606.7 using HMMER 3.1 (http://hmmer.org/) (J. Mistry, M. Punta; Challenges in Homology Search: HMMER3 and Convergent Evolution of Coiled-Coil Regions, Nucleic Acids Research, 41:el21, 2013). Specifically, hmmsearch was run with default parameters and all resulting hits considered.

The identified proteins and their corresponding genes with gene name annotation and function are listed in Table 1.

TABLE 1

| Gene name | Function | PRT | DNA | Accession |
|---|---|---|---|---|
| yhfR | putative phosphatase | SEQ ID 1 | SEQ ID 31 | PF14606.7 |
| yitV | putative peptidase | SEQ ID 2 | SEQ ID 32 | PF02230.17 |
| yesT | rhamnogalacturonan acetylesterase | SEQ ID 3 | SEQ ID 33 | PF13472.7 |
| yesT | rhamnogalacturonan acetylesterase | SEQ ID 3 | SEQ ID 33 | PF00657.23 |
| unknown | putative carbohydrate esterase | SEQ ID 4 | SEQ ID 34 | PF13472.7 |
| unknown | putative carbohydrate esterase | SEQ ID 4 | SEQ ID 34 | PF00657.23 |
| yesY | putative rhamnogalacturonan acetylesterase | SEQ ID 5 | SEQ ID 35 | PF13472.7 |
| yesY | putative rhamnogalacturonan acetylesterase | SEQ ID 5 | SEQ ID 35 | PF00657.23 |
| unknown | hypothetical protein | SEQ ID 6 | SEQ ID 36 | PF01764.26 |
| fliG | flagellar motor switch protein | SEQ ID 7 | SEQ ID 37 | PF03280.15 |
| yisY | AB hydrolase superfamily protein | SEQ ID 8 | SEQ ID 38 | PF01764.26 |
| yisY | AB hydrolase superfamily protein | SEQ ID 8 | SEQ ID 38 | PF03583.15 |
| yisY | AB hydrolase superfamily protein | SEQ ID 8 | SEQ ID 38 | PF02230.17 |
| mhqD | putative hydrolase | SEQ ID 9 | SEQ ID 39 | PF02230.17 |
| ypmR | putative esterase | SEQ ID 10 | SEQ ID 40 | PF13472.7 |
| ypmR | putative esterase | SEQ ID 10 | SEQ ID 40 | PF00657.23 |
| ypmR | putative esterase | SEQ ID 10 | SEQ ID 40 | PF14606.7 |
| lip | putative lipase | SEQ ID 11 | SEQ ID 41 | PF01674.19 |
| yqiL | hypothetical protein | SEQ ID 12 | SEQ ID 42 | PF01764.26 |
| yqeF | putative lipoprotein | SEQ ID 13 | SEQ ID 43 | PF13472.7 |
| yqeF | putative lipoprotein | SEQ ID 13 | SEQ ID 43 | PF00657.23 |
| unknown | putative lipolytic enzyme | SEQ ID 14 | SEQ ID 44 | PF01764.26 |
| unknown | putative lipolytic enzyme | SEQ ID 14 | SEQ ID 44 | PF02230.17 |
| ytaP | putative hydrolase | SEQ ID 15 | SEQ ID 45 | PF03583.15 |
| ytpA | phospholipase | SEQ ID 16 | SEQ ID 46 | PF02230.17 |
| ytmA | putative dipeptidylpeptidase | SEQ ID 17 | SEQ ID 47 | PF02230.17 |
| ytmA | putative dipeptidylpeptidase | SEQ ID 17 | SEQ ID 47 | PF03583.15 |
| ytxM | 2-succinyl-6-hydroxy-2, 4-cyclo-hexadiene-1-carboxylate synthase | SEQ ID 18 | SEQ ID 48 | PF02230.17 |
| yugF | alpha/beta hydrolase | SEQ ID 19 | SEQ ID 49 | PF02230.17 |
| yugF | alpha/beta hydrolase | SEQ ID 19 | SEQ ID 49 | PF01764.26 |
| unknown | dipeptidylpeptidase | SEQ ID 20 | SEQ ID 50 | PF03583.15 |

TABLE 1-continued

| Gene name | Function | PRT | DNA | Accession |
|---|---|---|---|---|
| unknown | dipeptidylpeptidase | SEQ ID 20 | SEQ ID 50 | PF02230.17 |
| yuxL | putative acylaminoacyl-peptidase | SEQ ID 21 | SEQ ID 51 | PF02230.17 |
| unknown | phage putative hydrolase protein | SEQ ID 22 | SEQ ID 52 | PF01764.26 |
| besA | trilactone hydrolase | SEQ ID 23 | SEQ ID 53 | PF02230.17 |
| unknown | rhamnogalacturonan acetylesterase | SEQ ID 24 | SEQ ID 54 | PF13472.7 |
| IchAD | lichenysin synthase | SEQ ID 25 | SEQ ID 55 | PF02230.17 |
| unknown | putative esterase | SEQ ID 26 | SEQ ID 56 | PF02230.17 |
| lipC | spore germination lipase LipC | SEQ ID 27 | SEQ ID 57 | PF13472.7 |
| lipC | spore germination lipase LipC | SEQ ID 27 | SEQ ID 57 | PF00657.23 |
| unknown | putative esterase/lipase | SEQ ID 28 | SEQ ID 58 | PF02230.17 |
| unknown | putative esterase/lipase | SEQ ID 28 | SEQ ID 58 | PF03583.15 |
| yrhL | putative peptidoglycan O-acetyltransferase | SEQ ID 29 | SEQ ID 59 | PF13472.7 |
| yrhL | putative peptidoglycan O-acetyltransferase | SEQ ID 29 | SEQ ID 59 | PF00657.23 |
| unknown | hypothetical protein | SEQ ID 30 | SEQ ID 60 | PF02230.17 |

Example 2: Identification of Lipase/Esterase Activity by Fractionation of *Bacillus Licheniformis* Fermentation Supernatant In order to characterize the esterase or lipase activity present in *Bacillus licheniformis* cultivations a *Bacillus licheniformis* (DaprE DamyB DsigF Dpga) was cultivated in a fed-batch fermentation as described in WO2020169563A1. The biomass was separated using a dead-end filtration and pretreatment of the fermentation broth with flocculant. The fermentation broth was pretreated using pDADMAC flocculation solution before the filtration step: 40 g Magnafloc® LT7996 (~20% w/v pDADMAC content) per 1 L of fermentation broth was diluted to the respective volume using deionized water to make up the flocculation solution. This solution was subsequently mixed 1:1 with the fermentation broth under constant stirring. After 15 min the pretreated broth was subjected to a three-step dead-end filtration: In a first step the biomass was separated using a dead-end filtration pressure nutsche unit on 200 mL scale using a high porosity perlite filter aid and a diatomite precoat: Body feed: 40 g/kg Harbolite 900; Precoat: 0.05 g/cm2 Dicalite BF. Subsequent filtration steps using depth filters K250 and EKS (Pall) yielded clear supernatant for subsequent chromatographic purification to isolate the lipolytic activity.

For anion exchange chromatography 10 mL sterile filtrated material was adjusted to 5 mS using 20 mM MOPS pH7.0 and loaded on a 6 mL Resource Q column (GE Healthcare). The column was washed with buffer A (20 mM MOPS, pH 7 supplemented with 5 mM MgCl2) until the baseline was achieved. Elution of bound material was performed using a linear gradient to buffer B (20 mM MOPS, pH 7 supplemented with 1 M NaCl and 5 mM MgCl2) over 40 column volumes with fractions being collected overtime. Esterase/Lipase activity was determined using pNP-butyrate as substrate. Herefore, the different fractions were mixed in a 1:1 ratio with 2 mM pNP-butyrate (in 10% DMSO, 100 mM MOPS buffer pH7, 100 mM NaCl, 0.045% Brij L23). The esterase/lipase activity was measured by following the absorbance increase over time at 405 nm. Using the activity data the lipase/esterase containing fractions identified and are used for LC-MS/MS analysis. The derived sample is called S1_IEX.

Orthogonally a hydrophobic interaction chromatography was performed using a HiPrep Butyl FF column (GE Healthcare). For chromatography 30 mL sterile filtrated material was adjusted to 25% saturation of ammonium sulfate and pH 7.0 using 20 mM MOPS. The material was loaded on a 20 mL HiPrep Butyl FF column (GE Healthcare). After loading the column, buffer A (20 mM MOPS, pH 7 supplemented with 5 mM MgCl2 and 25% saturation of Ammonium sulfate) was loaded until the baseline was achieved. Elution of bound material was performed using a linear gradient to buffer B (20 mM MOPS, pH 7 supplemented with 5 mM MgCl2) over 20 column volumes with fractions being collected over time. Esterase/Lipase activity was determined using pNP-butyrate as substrate. Herefore, the different fractions were mixed in a 1:1 ratio with 2 mM pNP-butyrate (in 10% DMSO, 100 mM MOPS buffer pH7, 100 mM NaCl, 0.045% Brij L23). The esterase/lipase activity was measured by following the absorbance increase over time at 405 nm. Using the activity data the lipase/esterase containing fractions are identified and are used for LCMS/MS analysis. The derived sample is called S2_HIC.

For LC-MS/MS the second sample set was processed with a S-Trap micro approach to desalt and digest the samples with trypsin. The generated peptides were analyzed via nanoLC-HRMS/MS. The acquired data was searched with the software MaxQuant against the *Bacillus licheniformis* proteome of DSM13 (strain ATCC 14580/DSM 13/JCM 2505/NBRC 12200/NCIMB 9375/NRRL NRS-1264/Gibson 46) with carbamidomethylation of cysteine as fixed and methionine oxidation and acetylated N-Term as variable modifications.

For the identification of the proteins only unique peptides were used and to reduce the number of false positive assigned spectra with an FDR cut-off of 0.01 was used. The protein list for the S1_IEX and S2_HIC samples was filtered for proteins that were identified by more than one peptide.

The protein list for the each of the samples was filtered for proteins that were identified by more than two peptides and an *andromeda* score better than 10. As evaluation the tables resulting from LC-MS/MS were compared to the table derived from example 1 in order to identify proteins being present in both analysis. In table 2 two proteins from the putative lipases/esterases (see Table 1) are depicted present in the fractions enriched for lipolytic activity using both purifications (ion exchange chromatography derived sample S1_IEX and hydrophobic interaction chromatography S2_HIC).

TABLE 2

| Name | Peptides | Sequence coverage [%] | Mol. weight [kDa] | gene | SEQ ID |
|---|---|---|---|---|---|
| YitV | 23 | 66.3 | 29.778 | yitV | 2 |
| YpmR | 6 | 29.6 | 28.469 | ypmR | 10 |

Example 3: Gene Knockout of Genes Encoding for Lipases/Esterases in *Bacillus licheniformis*

The genes yitV (SEQ ID 032) and ypmR (SEQ ID040) were deleted the in *Bacillus licheniformis* strain Bli #008.

Therefore, the yitV gene deletion plasmid was constructed as described above by cloning of the 5' and 3' flanking homologous regions into the *Bacillus/E. coli* shuttle plasmid pEC194RS. The 5' homologous region and the 3' homologous region were PCR-amplified with oligonucleotides SEQ ID 077 and SEQ ID 078, and oligonucleotides SEQ ID 079 and SEQ ID 080 respectively. The outermost oligonucleotides were flanked by BsaI sites compatible to pEC194RS. The type-II-assembly with restriction endonuclease BsaI was performed as described (Radeck et al., 2017; Sci. Rep. 7: 14134) and the reaction mixture was subsequently transformed into *E. coli* DH10B cells (Life technologies). Transformants were spread and incubated overnight at 37 C on LB-agar plates containing 100 μg/ml ampicillin. Plasmid DNA was isolated from individual clones and was analyzed for correctness by restriction digest. The resulting yitV gene deletion plasmid is named pDe1043 and was used for subsequent deletion in *Bacillus licheniformis* Bli #008.

The ypmR gene deletion plasmid was constructed as described for the yitV gene deletion plasmid, but the 5' homologous region and the 3' homologous region were PCR-amplified with oligonucleotides SEQ ID 081 and SEQ ID 082, and oligonucleotides SEQ ID 083 and SEQ ID 084 respectively.

The resulting ypmR gene deletion plasmid was used for subsequent deletion in *Bacillus licheniformis* Bli #008.

yitV Gene Deletion Strain Bli #080

Electrocompetent *Bacillus licheniformis* Bli #008 cells were prepared as described above and transformed with 1 μg of pDe1043 yitV gene deletion plasmid isolated from *E. coli* Ec #098 followed by plating on LB-agar plates containing 5 μg/ml erythromycin and incubation at 30° C.

The gene deletion procedure was performed as described for the aprE gene and successful gene deletion was monitored by colony-PCR.

ypmR Gene Deletion Strain Bli #081

Electrocompetent *Bacillus licheniformis* Bli #008 cells were prepared as described above and transformed with 1 μg of pDe1044 ypmR gene deletion plasmid isolated from *E. coli* Ec #098 followed by plating on LB-agar plates containing 5 μg/ml erythromycin and incubation at 30° C.

The gene deletion procedure was performed as described for the aprE gene and successful gene deletion was monitored by colony-PCR.

The combinatorial knockout strain comprising inactivated genes yitV (SEQ ID 032) and ypmR (SEQ ID 040) was constructed as described in the following.

yitV and ypmR Gene Deletion Strain Bli #082

Electrocompetent *Bacillus licheniformis* Bli #081 cells with deleted yitV gene were prepared as described above and transformed with 1 μg of pDe1044 ypmR gene deletion plasmid isolated from *E. coli* Ec #098 followed by plating on LB-agar plates containing 5 μg/ml erythromycin and incubation at 30° C.

The gene deletion procedure was performed as described for the aprE gene and successful gene deletion was monitored by colony-PCR.

Example 4 Lipase Activity of Strains Having the Lipases Deleted

In order to characterize the strains according the invention cultivations of *Bacillus licheniformis* strains Bli #008 (DaprE DamyB DsigF Dpga), Bli #080 (DaprE DamyB DsigF Dpga, DyitV), Bli #081 (DaprE DamyB DsigF Dpga, DypmR), and Bli #082 (DaprE DamyB DsigF Dpga, DyitV, DypmR) were tested and compared to the *Bacillus licheniformis* strain Bli #008 lacking the deletion(s) of yitV and/or ypmR. Herefore, the strains were cultivated as described in Example 2. After harvesting the fermenter, the broth was treated and chromatographic fractionation was performed as described in Example 2.

The esterase/lipase activity in the YitV and YpmR containing fractions of the reference strain Bli #008 and the corresponding fractions of the deletion strains Bli #080, Bli #081, and Bli #082 were determined using pNP-butyrate as substrate. Herefore, the different samples were mixed in a 1:1 ratio with 2 mM pNP-butyrate (in 10% DMSO, 100 mM MOPS buffer pH7, 100 mM NaCl, 0.045% Brij L23). The esterase/lipase activity was measured by following the absorbance increase over time at 405 nm. See below the activity for the respective strains (one unit is defined as the release of 1 μmol pNP in 1 min:

| Strain | Genotype | Lipase activity rel. to control strain |
|---|---|---|
| Bli#008 (control strain) | DaprE DamyB DsigF Dpga | 100% |
| Bli#082 | DaprE DamyB DsigF Dpga DyitV DypmR | <4% |
| Bli#080 | DaprE DamyB DsigF Dpga DyitV | 22% |
| Bli#081 | DaprE DamyB DsigF Dpga DypmR | 36% |

It can be seen that the deletion of YitV and/or YpmR reduces the lipolytic activity compared to the wildtype.

The invention claimed is:

1. A recombinant *Bacillus* cell comprising inactivated yitV and ypmR genes, wherein the recombinant *Bacillus* cell does not produce active YitV protein and does not produce active YpmR protein.

2. The recombinant *Bacillus* cell of claim 1, wherein the *Bacillus* cell produces a protein of interest.

3. The recombinant *Bacillus* cell of claim 1, comprising a gene encoding for the protein of interest.

4. The recombinant *Bacillus* of claim 1, wherein the *Bacillus* cell is selected from the group including consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus, Bacillus paralicheniformis, Bacillus subtilis*, and *Bacillus thuringiensis* cells.

5. The recombinant *Bacillus* cell of claim 1, wherein the yitV gene encodes a YitV protein that is selected from the group consisting of:

(a) a YitV protein having at least 70% identity with SEQ ID NO: 2;

(b) a YitV protein encoded by a polynucleotide having at least 70% identity with SEQ ID NO: 32;

(c) a YitV protein encoded by a polynucleotide that hybridizes under high stringency conditions with (i) a polynucleotide comprising SEQ ID NO: 32 or (ii) the full-length complement of (i), wherein the high stringency conditions comprise a wash of 1.06×SSC, 0.1% SDS, 0% formamide at 65° C.;

(d) a variant of the YitV protein of SEQ ID NO: 2 comprising a substitution, deletion, and/or insertion at one or more positions and having lipase and/or esterase activity;

(e) a YitV protein encoded by a polynucleotide that differs from SEQ ID NO: 32 due to the degeneracy of the genetic code.

6. The recombinant *Bacillus* cell of claim 1, wherein the ypmR gene encodes a YpmR protein that is selected from the group consisting of:

(a) a YpmR protein having at least 70% identity with SEQ ID NO: 10;

(b) a YpmR protein encoded by a polynucleotide having at least 70% identity with SEQ ID NO: 40;

(c) a YpmR protein encoded by a polynucleotide that hybridizes under high stringency conditions with (i) a polynucleotide comprising SEQ ID NO: 40 or (ii) the full-length complement of (i), wherein the high stringency conditions comprise a wash of 1.06×SSC, 0.1% SDS, 0% formamide at 65° C.;

(d) a variant of the YpmR protein of SEQ ID NO: 10 comprising a substitution, deletion, and/or insertion at one or more positions and having lipase and/or esterase activity;

(e) a YpmR protein encoded by a polynucleotide that differs from SEQ ID NO: 40 due to the degeneracy of the genetic code.

7. The recombinant *Bacillus* cell of claim 2, wherein the protein of interest is an enzyme.

8. A method for producing a compound of interest, comprising the steps of a) providing the recombinant *Bacillus* cell of claim 1, b) introducing an expression cassette encoding the compound of interest into said recombinant *Bacillus* cell an expression cassette for a compound of interest, c) cultivating said recombinant *Bacillus* cell under conditions which allow for the expression of the compound of interest, and d) optionally, isolating the compound of interest.

9. A method for reducing the lipase and/or esterase activity in a *Bacillus* cell comprising inactivating the yitV and/or ypmR gene in the *Bacillus* cell.

10. A method for reducing the lipase and/or esterase activity of a compound of interest produced by a *Bacillus* cell comprising the steps of a) providing the recombinant *Bacillus* cell of claim 1, b) introducing an expression cassette encoding the compound of interest into said recombinant *Bacillus* cell, c) cultivating said recombinant *Bacillus* cell under conditions which allow for the expression of the compound of interest, and d) optionally, isolating the compound of interest, thereby, reducing the lipase and/or esterase activity of the compound of interest.

11. A method for reducing the formation of malodour or off-flavor in a composition comprising a compound of interest produced by a *Bacillus* cell comprising the steps of a) providing the recombinant *Bacillus* cell of claim 1, b) introducing an expression cassette encoding the compound of interest into said recombinant *Bacillus* cell, c) cultivating said recombinant *Bacillus* cell under conditions which allow for the expression of the compound of interest, and d) optionally, isolating the compound of interest thereby, reducing the formation of malodour or off-flavor in the composition comprising the compound of interest.

12. The recombinant *Bacillus* cell of claim 7, wherein the protein of interest is an enzyme selected from the group consisting of amylase, alpha-amylase, glucoamylase, pullulanase, protease, lipase, cutinase, acyl transferase, cellulase, endoglucanase, glucosidase, cellubiohydrolase, lactase, xylanase, xyloglucantransferase, xylosidase, mannanase, phytase, phosphatase, xylose isomerase, glucoase isomerase, acetolactate decarboxylase, pectinase, pectin methylesterase, polygalacturonidase, lyase, pectate lyase, arabinase, arabinofuranosidase, galactanase, laccase, peroxidase and an asparaginase.

13. The recombinant *Bacillus* cell of claim 1, wherein the recombinant *Bacillus* cell comprises a complete or partial deletion of the yitV gene and a complete or partial deletion of the ypmR gene.

* * * * *